US009187553B2

(12) United States Patent
Chen

(10) Patent No.: US 9,187,553 B2
(45) Date of Patent: Nov. 17, 2015

(54) DISPLAYING NATIVE HUMAN IGE NEUTRALIZING FCEPSILONRIA-CONTACTING IGE B-CELL EPITOPES BY CONSTRAINING SUPER BETA(B)-STRANDS AND CYSTINE KNOTS ON THERMOSTABLE PROTEIN SCAFFOLD

(71) Applicant: Swy-Shen Chen, San Diego, CA (US)

(72) Inventor: Swy-Shen Chen, San Diego, CA (US)

(73) Assignee: Swey-Shen Chen, San Diego, CA (US)

( * ) Notice: Subject to any disclaimer, the term of this patent is extended or adjusted under 35 U.S.C. 154(b) by 61 days.

(21) Appl. No.: 13/815,042

(22) Filed: Jan. 25, 2013

(65) Prior Publication Data

US 2014/0039162 A1    Feb. 6, 2014

Related U.S. Application Data

(60) Provisional application No. 61/590,778, filed on Jan. 25, 2012.

(51) Int. Cl.
*A61K 39/00* (2006.01)
*C07K 16/00* (2006.01)
*C07K 16/42* (2006.01)

(52) U.S. Cl.
CPC ............. *C07K 16/00* (2013.01); *A61K 39/00* (2013.01); *C07K 16/4291* (2013.01); *A61K 2039/6056* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 5,653,980 A * | 8/1997 | Hellman | ............... | 424/184.1 |
| 6,811,782 B1 * | 11/2004 | Wang et al. | ............... | 424/185.1 |
| 6,913,749 B2 * | 7/2005 | Hellman | ............... | 424/185.1 |
| 6,974,572 B2 * | 12/2005 | Morsey et al. | ............... | 424/133.1 |
| 7,232,898 B2 * | 6/2007 | Lundgren et al. | ............... | 536/23.1 |
| 8,298,547 B2 * | 10/2012 | Brown et al. | ............... | 424/185.1 |

FOREIGN PATENT DOCUMENTS

| | | | |
|---|---|---|---|
| EP | 1195161 A2 * | 4/2002 | |
| WO | WO 9305810 A1 * | 4/1993 | |
| WO | WO 9526365 A1 * | 10/1995 | |

\* cited by examiner

*Primary Examiner* — Michael Szperka
(74) *Attorney, Agent, or Firm* — Swey-Shen Chen

(57) ABSTRACT

Vaccine displaying native antigenic loops of immunoglobulin E is critical for eliciting neutralizing anti-IgE antibodies. The embodiment of the invention enables the display of native antigenic IgE receptor-contacting loops as IgE B-cell vaccines via three steps of constraining methods. The loops of multiple antigenic B-cell epitopes can be molecularly grafted in, and conformationally constrained by the energy favorable flanking beta (b)-stands, i.e., the super b-strands identified in this invention. The constrained loops can be further stabilized in replacing a selective loop within the cystine knot peptide. These dual constrained antigenic loops are then integrated onto thermostable protein scaffolds, folded in the oxidative milieu that provides further conformational constraint and high yield.

20 Claims, 23 Drawing Sheets

Figure 1. The primary sequence and secondary structures of human IgE CHe2 to CHe4 domain Figure 2. Expression of mini- and micro-IgE-GFPuv fusion proteins.

FIG. 6

Figure 6. Detection of swapped native human C2-3, BC, and DE core loop sequences in super-b-strand of truncated FG microdomain on GFP

A

123 KDa →

B

35 → KDa

Panel A: native gel, western with pAb(NAE)
Ln 1: GFP+FG full length (ln 1); Ln 2: GFP+FG (-5) Ln 3: GFP+FG (-10); Ln 4: GFP (-5) delete HLPR; Ln5: GFP+FG(-5)+RNGT; Ln 6: GFP+FG(-10)+NPRGVS; Ln7: GFP+FG(-10)+DLAP; Ln8: IgE (BED)
Panel B: denatured, western with anti-GFP; Lane order: same as Panel A

FIG. 7A

Figure 7 A. Native IgE epitope expression:
Comparison native expression of swapped C2-3, BC, DE loop B-cell epitope in super b-strands of FG-N5 versus FG-N10 FG microdomain onto GFP scaffold 1) IgE (BED)
2) GFPuv
3) GFPuv + DE (full length)
4) GFPuv + BC (full length)
5) GFPuv + FG del 10AA N term DLAP swap
6) GFPuv + FG del 5AA N term DLAP swap
7) GFPuv + FG del 10AA N term NPRGVS swap
8) GFPuv + FG del 5AA N term NPRGVS swap
9) GFPuv + FG del 10AA N term RNGT swap
10) GFPuv + FG del 5AA N term RNGT swap
11) GFPuv + FG del 10AA N term minus HLPR
12) GFPuv + FG del 5AA N term minus HLPR
13) GFPuv + FG del 10AA N term
14) GFPuv + FG del 5AA N term

FIG. 7B

Figure 7 B. Denatured GFP epitope expression:
Comparison native expression of swapped C2-3, BC, DE loop B-cell epitope in super b-strands of FG-N5 versus FG-N10 FG microdomain onto GFP scaffold 1) GFPuv + FG del 5AA N term (200 ng)
2) GFPuv + FG del 10AA N term
3) GFPuv + FG del 5AA N term minus HLPR
4) GFPuv + FG del 10AA N term minus HLPR
5) GFPuv + FG del 5AA N term RNGT swap
6) GFPuv + FG del 10AA N term RNGT swap
7) GFPuv + FG del 5AA N term NPRGVS swap
8) GFPuv + FG del 10AA N term NPRGVS swap
9) GFPuv + FG del 5AA N term DLAP swap
10) GFPuv + FG del 10AA N term DLAP swap
11) GFPuv + BC (full length)
12) GFPuv + DE (full length)
13) GFPuv
14) IgE (BED)

FIG. 7C

Figure 7C. Denatured IgE epitope expression:
Comparison native expression of swapped C2-3, BC, DE loop B-cell epitope in super b-strands of FG-N5 versus FG-N10 FG microdomain onto GFP scaffold 1) IgE (BED)
2) GFPuv
3) GFPuv + DE (full length) (200 ng)
4) GFPuv + BC (full length)
5) GFPuv + FG del 10AA N term DLAP swap
6) GFPuv + FG del 5AA N term DLAP swap
7) GFPuv + FG del 10AA N term NPRGVS swap
8) GFPuv + FG del 5AA N term NPRGVS swap
9) GFPuv + FG del 10AA N term RNGT swap
10) GFPuv + FG del 5AA N term RNGT swap
11) GFPuv + FG del 10AA N term minus HLPR
12) GFPuv + FG del 5AA N term minus HLPR
13) GFPuv + FG del 10AA N term
14) GFPuv + FG del 5AA N term

FIG. 8

Figure 8. Rodent sequences for C2-3, BC, DE loop swapped surrogate vaccines

Human FG beta-strand minus 10AA N-term and deleted FG determinant HLPR in GFPuv:

```
                         TMITPSL      QCRVTHP(    )ALMRSTTKTSGPR VPVEK MSK
Substitute Mouse FG determinant:TMITPSL      QCRVTHP(NNAT)ALMRSTTKTSGPR VPVEK MSK
Substitute Mouse BC determinant:
                         TMITPSL      QCRVTHP(DLAE)ALMRSTTKTSGPR VPVEK MSK
Substitute Human BC determinant:

Substitute Mouse C2-3 determinant:
                         TMITPSL      QCRVTHP(EPRGVI)ALMRSTTKTSGPR VPVEK MSK
Substitute Human C2-3 determinant:
                         TMITPSL      QCRVTHP(NPRGVS)ALMRSTTKTSGPR VPVEK MSK
```

FIG. 9

Figure 9. anti-IgE elicited by FG-N-10-GFP blocking human IgE binding to recombinant human FceRIa A  Stanard BED binding to D2/D1

50 ng/ml sigan

B  Neutralizing BED binding to D2/D1 area under suppression anti-FG loop serum titration
+50 ng/ml BED

FIG. 14

Figure 14. Expression of loop B-cell epitopes of BC and DE swapped into loop 1, 2, 3, 5 of wild type EETI-II

VDLAPS: Amino Acid determinants of BC region of human IgE Heavy chain
QRNGTL: Amino Acid determinants of DE region of human IgE Heavy chain

```
              Cys      Loop 1       Cys     Loop 2      Cys   Loop 3
           GGGTGCCCGCGAATCCTAATGCGTTGCAAACAGGACTCCGACTGCCTGGCT
EETI-II:     G   C   P   R   I   L   M   R   C   K   Q   D   S   D   C   L   A
              CysLoop 4Cys         Loop 5      Cys
           GGCTGCGTTTGCGGGCCCAACGGTTTCTGCGGA
             G   C   V   C   G   P   N   G   F   C   G
```

L-1
EETI-II casette with Loop 1 deletion    GccKQDSDcLAGcVcGPNGFcG

Clone 1: Insert VDLAPS
              Clone 2: Insert QRNGTL            L-2
EETI-II casette with Loop 2 deletion    GcPRILMRccLAGcVcGPNGFcG Clone 3: Insert VDLAPS
              Clone 4: Insert QRNGTL            L-3
EETI-II casette with Loop 3 deletion    GcPRILMRcKQDSDccVcGPNGFcG Clone 5: Insert VDLAPS
              Clone 6: Insert QRNGTL                      L-5
EETI-II casette with Loop 5 deletion    GcPRILMRcKQDSDcLAGcVccG Clone 7: Insert VDLAPS
              Clone 8: Insert QRNGTL

GCPRILMRCKQDSDCLAGCVCGPNGFCG

FIG. 19

Figure 19. Enhanced reactivities of native truncated N-10 FG-Min-18-pMal (Min-23 series) with neutralizing anti-human IgE Legend:
1) pMal-min23+FG(full length)
2) pMal-min23+FG del 5 AA N-term
3) pMal-min23+FG del 15 AA N-term
4) pMal-min23+FG del 18 AA N-term
5) pMal-min23+FG del 3 AA C-term
6) pMal-min23+FG del 5AA C-term
7) pMal-min23+FG del 10AA C-term
8) pMal-min23 with Loop 5 deleted (neg. control)
9) Pure IgE (BED) 150 ng (positive control)

SEQUENCE LISTING

<160> NUMBER OF SEQ ID NOS: 280

<210> SEQ ID NO 1
<211> LENGTH: 1920
<212> TYPE: DNA
<213> ORGANISM: homo sapiens

<400> SEQUENCE: 1

```
ggatccctgc acggggtcc  ccagctcccc  catccaggcc  cccaggctg   atgggcgctg     60
gcctgaggct ggcactgact aggttctgtc ctcacagcct ccacacagag cccatccgtc    120
ttccccttga cccgctgctg caaaaacatt ccctccaatg ccacctccgt gactctgggc    180
tgcctggcca cgggctactt cccggagccg gtgatggtga cctgggacac aggctccctc    240
aacgggacaa ctatgacctt accagccacc accctcacgc tctctggtca ctatgccacc    300
atcagcttgc tgaccgtctc gggtgcgtgg gccaagcaga tgttcacctg ccgtgtggca    360
cacactccat cgtccacaga ctgggtcgac aacaaaacct tcagcggtaa gagagggcca    420
agctcagaga ccacagttcc caggagtgcc aggctgaggt ctggcagagt gggcaggggt    480
tgaggggtg  ggtgggctca aacgtgggaa cacccagcat gcctggggac ccgggccagg    540
acgtgggggc aagaggaggg cacacagagc tcagagaggc caacaaccct catgaccacc    600
agctctcccc cagtctgctc cagggacttc accccgccca ccgtgaagat cttacagtcg    660
tcctgcgacg gcggcgggca cttcccccccg accatccagc tcctgtgcct cgtctctggg    720
tacacccccag ggactatcaa catcacctgg ctggaggacg ggcaggtcat ggacgtggac    780
ttgtccaccg cctctaccac gcaggagggt gagctggcct ccacacaaag cgagctcacc    840
ctcagccaga agcactggct gtcagaccgc acctacacct gccaggtcac ctatcaaggt    900
cacacctttg aggacagcac caagaagtgt gcaggtacgt tcccacctgc cctggtggcc    960
gccacggagg ccagagaaga ggggcgggtg ggcctcacac agccctccgg tgtaccacag   1020
attccaaccc gagagggtg  agcgcctacc taagccggcc cagcccgttc gacctgttca   1080
tccgcaagtc gcccacgatc acctgtctgg tggtggacct ggcacccagc aaggggaccg   1140
tgaacctgac ctggtcccgg gccagtggga agcctgtgaa ccactccacc agaaaggagg   1200
agaagcagcg caatggcacg ttaaccgtca cgtccacccct gccggtgggc acccgagact   1260
ggatcgaggg ggagacctac cagtgcaggg tgacccaccc ccacctgccc agggccctca   1320
tgcggtccac gaccaagacc agcggtgagc catgggcagg ccggggtcgt ggggaaggg   1380
agggagcgag tgagcggggc ccgggctgac cccacgtctg gccacaggcc cgcgtgctgc   1440
cccggaagtc tatgcgtttg cgacgccgga gtggccgggg agccgggaca agcgcaccct   1500
cgcctgcctg atccagaact tcatgcctga ggacatctcg gtgcagtggc tgcacaacga   1560
```

-continued

```
ggtgcagctc ccggacgccc ggcacagcac gacgcagccc cgcaagacca agggctccgg   1620
cttcttcgtc ttcagccgcc tggaggtgac cagggccgaa tgggagcaga aagatgagtt   1680
catctgccgt gcagtccatg aggcagcgag cccctcacag accgtccagc gagcggtgtc   1740
tgtaaatccc ggtaaatgac gtactcctgc ctccctccct cccagggctc catccagctg   1800
tgcagtgggg aggactggcc agaccttctg tccactgttg caatgacccc aggaagctac   1860
ccccaataaa ctgtgcctgc tcagagcccc agtacaccca ttcttgggag cgggcagggc   1920
```

<210> SEQ ID NO 2
<211> LENGTH: 574
<212> TYPE: PRT
<213> ORGANISM: homo sapiens

<400> SEQUENCE: 2

Met Asp Trp Thr Trp Ile Leu Phe Leu Val Ala Ala Thr Arg Val
1               5                   10                  15

His Ser Gln Thr Gln Leu Val Gln Ser Gly Ala Glu Val Arg Lys Pro
                20                  25                  30

Gly Ala Ser Val Arg Val Ser Cys Lys Ala Ser Gly Tyr Thr Phe Ile
            35                  40                  45

Asp Ser Tyr Ile His Trp Ile Arg Gln Ala Pro Gly His Gly Leu Glu
        50                  55                  60

Trp Val Gly Trp Ile Asn Pro Asn Ser Gly Gly Thr Asn Tyr Ala Pro
65                  70                  75                  80

Arg Phe Gln Gly Arg Val Thr Met Thr Arg Asp Ala Ser Phe Ser Thr
                85                  90                  95

Ala Tyr Met Asp Leu Arg Ser Leu Arg Ser Asp Asp Ser Ala Val Phe
            100                 105                 110

Tyr Cys Ala Lys Ser Asp Pro Phe Trp Ser Asp Tyr Tyr Asn Phe Asp
        115                 120                 125

Tyr Ser Tyr Thr Leu Asp Val Trp Gly Gln Gly Thr Thr Val Thr Val
    130                 135                 140

Ser Ser Ala Ser Thr Gln Ser Pro Ser Val Phe Pro Leu Thr Arg Cys
145                 150                 155                 160

Cys Lys Asn Ile Pro Ser Asn Ala Thr Ser Val Thr Leu Gly Cys Leu
                165                 170                 175

Ala Thr Gly Tyr Phe Pro Glu Pro Val Met Val Thr Trp Asp Thr Gly
            180                 185                 190

Ser Leu Asn Gly Thr Thr Met Thr Leu Pro Ala Thr Thr Leu Thr Leu
        195                 200                 205

Ser Gly His Tyr Ala Thr Ile Ser Leu Leu Thr Val Ser Gly Ala Trp
    210                 215                 220

Ala Lys Gln Met Phe Thr Cys Arg Val Ala His Thr Pro Ser Ser Thr
225                 230                 235                 240

Asp Trp Val Asp Asn Lys Thr Phe Ser Val Cys Ser Arg Asp Phe Thr
                245                 250                 255

Pro Pro Thr Val Lys Ile Leu Gln Ser Ser Cys Asp Gly Gly His
            260                 265                 270

Phe Pro Pro Thr Ile Gln Leu Leu Cys Leu Val Ser Gly Tyr Thr Pro
        275                 280                 285

Gly Thr Ile Asn Ile Thr Trp Leu Glu Asp Gly Gln Val Met Asp Val
    290                 295                 300

Asp Leu Ser Thr Ala Ser Thr Thr Gln Glu Gly Glu Leu Ala Ser Thr

```
                305                 310                 315                 320
        Gln Ser Glu Leu Thr Leu Ser Gln Lys His Trp Leu Ser Asp Arg Thr
                        325                 330                 335
        Tyr Thr Cys Gln Val Thr Tyr Gln Gly His Thr Phe Glu Asp Ser Thr
                        340                 345                 350
        Lys Lys Cys Ala Asp Ser Asn Pro Arg Gly Val Ser Ala Tyr Leu Ser
                        355                 360                 365
        Arg Pro Ser Pro Phe Asp Leu Phe Ile Arg Lys Ser Pro Thr Ile Thr
                370                 375                 380
        Cys Leu Val Val Asp Leu Ala Pro Ser Lys Gly Thr Val Asn Leu Thr
        385                 390                 395                 400
        Trp Ser Arg Ala Ser Gly Lys Pro Val Asn His Ser Thr Arg Lys Glu
                        405                 410                 415
        Glu Lys Gln Arg Asn Gly Thr Leu Thr Val Thr Ser Thr Leu Pro Val
                        420                 425                 430
        Gly Thr Arg Asp Trp Ile Glu Gly Glu Thr Tyr Gln Cys Arg Val Thr
                        435                 440                 445
        His Pro His Leu Pro Arg Ala Leu Met Arg Ser Thr Thr Lys Thr Ser
                450                 455                 460
        Gly Pro Arg Ala Ala Pro Glu Val Tyr Ala Phe Ala Thr Pro Glu Trp
        465                 470                 475                 480
        Pro Gly Ser Arg Asp Lys Arg Thr Leu Ala Cys Leu Ile Gln Asn Phe
                        485                 490                 495
        Met Pro Glu Asp Ile Ser Val Gln Trp Leu His Asn Glu Val Gln Leu
                        500                 505                 510
        Pro Asp Ala Arg His Ser Thr Thr Gln Pro Arg Lys Thr Lys Gly Ser
                        515                 520                 525
        Gly Phe Phe Val Phe Ser Arg Leu Glu Val Thr Arg Ala Glu Trp Glu
                530                 535                 540
        Gln Lys Asp Glu Phe Ile Cys Arg Ala Val His Glu Ala Ala Ser Pro
        545                 550                 555                 560
        Ser Gln Thr Val Gln Arg Ala Val Ser Val Asn Pro Gly Lys
                        565                 570

<210> SEQ ID NO 3
<211> LENGTH: 108
<212> TYPE: DNA
<213> ORGANISM: homo sapiens

<400> SEQUENCE: 3
cgcacctata cctgccaggt gacctatcag ggccatacct ttgaagatag caccaaaaaa         60
tgcgcggata gcaacccgcg cggcgtgagc gcgtatctga gccgcccg                     108

<210> SEQ ID NO 4
<211> LENGTH: 36
<212> TYPE: PRT
<213> ORGANISM: Homo sapiens

<400> SEQUENCE: 4

Arg Thr Tyr Thr Cys Gln Val Thr Tyr Gln Gly His Thr Phe Glu Asp
1               5                   10                  15

Ser Thr Lys Lys Cys Ala Asp Ser Asn Pro Arg Gly Val Ser Ala Tyr
                20                  25                  30

Leu Ser Arg Pro
        35
```

<210> SEQ ID NO 5
<211> LENGTH: 90
<212> TYPE: DNA
<213> ORGANISM: Homo sapiens

<400> SEQUENCE: 5
agcccgtttg atctgtttat tcgcaaaagc ccgaccatta cctgcctggt ggtggatctg    60
gcgccgagca aaggcaccgt gaacctgacc                                    90

<210> SEQ ID NO 6
<211> LENGTH: 30
<212> TYPE: PRT
<213> ORGANISM: Homo sapiens

<400> SEQUENCE: 6

Ser Pro Phe Asp Leu Phe Ile Arg Lys Ser Pro Thr Ile Thr Cys Leu
1               5                   10                  15

Val Val Asp Leu Ala Pro Ser Lys Gly Thr Val Asn Leu Thr
            20                  25                  30

<210> SEQ ID NO 7
<211> LENGTH: 81
<212> TYPE: DNA
<213> ORGANISM: Homo sapiens

<400> SEQUENCE: 7
aaaccggtga accatagcac ccgcaaagaa gaaaaacagc gcaacggcac cctgaccgtg    60
accagcaccc tgccggtggg c                                             81

<210> SEQ ID NO 8
<211> LENGTH: 27
<212> TYPE: PRT
<213> ORGANISM: Homo sapiens

<400> SEQUENCE: 8

Lys Pro Val Asn His Ser Thr Arg Lys Glu Glu Lys Gln Arg Asn Gly
1               5                   10                  15

Thr Leu Thr Val Thr Ser Thr Leu Pro Val Gly
            20                  25

<210> SEQ ID NO 9
<211> LENGTH: 102
<212> TYPE: DNA
<213> ORGANISM: Homo sapiens

<400> SEQUENCE: 9
acccgcgatt ggattgaagg cgaaacctat cagtgccgcg tgacccatcc gcatctgccg    60
cgcgcgctga tgcgcagcac caccaaaacc agcggcccgc gc                     102

<210> SEQ ID NO 10
<211> LENGTH: 34
<212> TYPE: PRT
<213> ORGANISM: Homo sapiens

<400> SEQUENCE: 10

Thr Arg Asp Trp Ile Glu Gly Glu Thr Tyr Gln Cys Arg Val Thr His
1               5                   10                  15

Pro His Leu Pro Arg Ala Leu Met Arg Ser Thr Thr Lys Thr Ser Gly
            20                  25                  30

Pro Arg

<210> SEQ ID NO 11
<211> LENGTH: 87
<212> TYPE: DNA
<213> ORGANISM: Homo sapiens

<400> SEQUENCE: 11
gagggcgaga cctaccagtg cagggtgacc caccccacc tgcccagggc cctgatgagg    60
agcaccacca agaccagcgg ccccagg                                       87

<210> SEQ ID NO 12
<211> LENGTH: 29
<212> TYPE: PRT
<213> ORGANISM: Homo sapiens

<400> SEQUENCE: 12

Glu Gly Glu Thr Tyr Gln Cys Arg Val Thr His Pro His Leu Pro Arg
1               5                   10                  15

Ala Leu Met Arg Ser Thr Thr Lys Thr Ser Gly Pro Arg
            20                  25

<210> SEQ ID NO 13
<211> LENGTH: 72
<212> TYPE: DNA
<213> ORGANISM: Homo sapiens

<400> SEQUENCE: 13
cagtgcaggg tgacccaccc ccacctgccc agggccctga tgaggagcac caccaagacc    60
agcggcccca gg                                                        72

<210> SEQ ID NO 14
<211> LENGTH: 24
<212> TYPE: PRT
<213> ORGANISM: Homo sapiens

<400> SEQUENCE: 14

Gln Cys Arg Val Thr His Pro His Leu Pro Arg Ala Leu Met Arg Ser
1               5                   10                  15

Thr Thr Lys Thr Ser Gly Pro Arg
            20

<210> SEQ ID NO 15
<211> LENGTH: 57
<212> TYPE: DNA
<213> ORGANISM: Homo sapiens

<400> SEQUENCE: 15 caccccacc tgcccagggc cctgatgagg agcaccacca agaccagcgg ccccagg        57

<210> SEQ ID NO 16
<211> LENGTH: 19
<212> TYPE: PRT
<213> ORGANISM: Homo sapiens

<400> SEQUENCE: 16

His Pro His Leu Pro Arg Ala Leu Met Arg Ser Thr Thr Lys Thr Ser
1               5                   10                  15

Gly Pro Arg

<210> SEQ ID NO 17
<211> LENGTH: 60

<212> TYPE: DNA
<213> ORGANISM: Homo sapiens

<400> SEQUENCE: 17
cagtgcaggg tgacccaccc cgccctgatg aggagcacca ccaagaccag cggccccagg    60

<210> SEQ ID NO 18
<211> LENGTH: 25
<212> TYPE: PRT
<213> ORGANISM: Homo sapiens

<400> SEQUENCE: 18

Glu Gly Glu Thr Tyr Gln Cys Arg Val Thr His Pro Ala Leu Met Arg
1               5                   10                  15

Ser Thr Thr Lys Thr Ser Gly Pro Arg
            20                  25

<210> SEQ ID NO 19
<211> LENGTH: 45
<212> TYPE: DNA
<213> ORGANISM: Homo sapiens

<400> SEQUENCE: 19
caccccgccc tgatgaggag caccaccaag accagcggcc ccagg    45

<210> SEQ ID NO 20
<211> LENGTH: 15
<212> TYPE: PRT
<213> ORGANISM: Homo sapiens

<400> SEQUENCE: 20

His Pro Ala Leu Met Arg Ser Thr Thr Lys Thr Ser Gly Pro Arg
1               5                   10                  15

<210> SEQ ID NO 21
<211> LENGTH: 87
<212> TYPE: DNA
<213> ORGANISM: Homo sapiens

<400> SEQUENCE: 21
gagggcgaga cctaccagtg cagggtgacc caccccacc tgcccagggc cctgatgagg    60
agcaccacca agaccagcgg ccccagg    87

<210> SEQ ID NO 22
<211> LENGTH: 12
<212> TYPE: DNA
<213> ORGANISM: Homo sapiens

<400> SEQUENCE: 22
cacctgccca gg    12

<210> SEQ ID NO 23
<211> LENGTH: 4
<212> TYPE: PRT
<213> ORGANISM: Homo sapiens

<400> SEQUENCE: 23

His Leu Pro Arg
1

<210> SEQ ID NO 24
<211> LENGTH: 27
<212> TYPE: DNA

```
<213> ORGANISM: Homo sapiens

<400> SEQUENCE: 24
caccccacca agaccagcgg ccccagg                                              27

<210> SEQ ID NO 25
<211> LENGTH: 9
<212> TYPE: PRT
<213> ORGANISM: Homo sapiens

<400> SEQUENCE: 25

His Pro Thr Lys Thr Ser Gly Pro Arg
1               5

<210> SEQ ID NO 26
<211> LENGTH: 75
<212> TYPE: DNA
<213> ORGANISM: Homo sapiens

<400> SEQUENCE: 26
tatcagtgcc gcgtgaccca tccgcatctg ccgcgcgcgc tgatgcgcag caccaccaaa         60
accagcggcc cgcgc                                                          75

<210> SEQ ID NO 27
<211> LENGTH: 25
<212> TYPE: PRT
<213> ORGANISM: Homo sapiens

<400> SEQUENCE: 27

Tyr Gln Cys Arg Val Thr His Pro His Leu Pro Arg Ala Leu Met Arg
1               5                   10                  15

Ser Thr Thr Lys Thr Ser Gly Pro Arg
            20                  25

<210> SEQ ID NO 28
<211> LENGTH: 51
<212> TYPE: DNA
<213> ORGANISM: Homo sapiens

<400> SEQUENCE: 28
cagtgccgcg tgacccatcc gcatctgccg cgcgcgctga tgcgcagcac c                  51

<210> SEQ ID NO 29
<211> LENGTH: 17
<212> TYPE: PRT
<213> ORGANISM: Homo sapiens

<400> SEQUENCE: 29

Gln Cys Arg Val Thr His Pro His Leu Pro Arg Ala Leu Met Arg Ser
1               5                   10                  15

Thr

<210> SEQ ID NO 30
<211> LENGTH: 36
<212> TYPE: DNA
<213> ORGANISM: Homo sapiens

<400> SEQUENCE: 30
catccgcatc tgccgcgcgc gctgatgcgc agcacc                                   36

<210> SEQ ID NO 31
<211> LENGTH: 12
```

```
<212> TYPE: PRT
<213> ORGANISM: Homo sapiens

<400> SEQUENCE: 31

His Pro His Leu Pro Arg Ala Leu Met Arg Ser Thr
1               5                   10

<210> SEQ ID NO 32
<211> LENGTH: 24
<212> TYPE: DNA
<213> ORGANISM: Homo sapiens

<400> SEQUENCE: 32
catccggcgc tgatgcgcag cacc                                          24

<210> SEQ ID NO 33
<211> LENGTH: 39
<212> TYPE: DNA
<213> ORGANISM: Homo sapiens

<400> SEQUENCE: 33
cagtgccgcg tgacccatcc ggcgctgatg cgcagcacc                          39

<210> SEQ ID NO 34
<211> LENGTH: 13
<212> TYPE: PRT
<213> ORGANISM: Homo sapiens

<400> SEQUENCE: 34

Gln Cys Arg Val Thr His Pro Ala Leu Met Arg Ser Thr
1               5                   10

<210> SEQ ID NO 35
<211> LENGTH: 21
<212> TYPE: DNA
<213> ORGANISM: Homo sapiens

<400> SEQUENCE: 35
cagtgccgcg tgacccatcc g                                             21

<210> SEQ ID NO 36
<211> LENGTH: 7
<212> TYPE: PRT
<213> ORGANISM: Homo sapiens

<400> SEQUENCE: 36

Gln Cys Arg Val Thr His Pro
1               5

<210> SEQ ID NO 37
<211> LENGTH: 18
<212> TYPE: DNA
<213> ORGANISM: Homo sapiens

<400> SEQUENCE: 37
tatcagtgcc gcgtgacc                                                 18

<210> SEQ ID NO 38
<211> LENGTH: 6
<212> TYPE: PRT
<213> ORGANISM: Homo sapiens

<400> SEQUENCE: 38

Tyr Gln Cys Arg Val Thr
```

<210> SEQ ID NO 39
<211> LENGTH: 18
<212> TYPE: DNA
<213> ORGANISM: Homo sapiens

<400> SEQUENCE: 39
gcgctgatgc gcagcacc                                                  18

<210> SEQ ID NO 40
<211> LENGTH: 6
<212> TYPE: PRT
<213> ORGANISM: Homo sapiens

<400> SEQUENCE: 40

Ala Leu Met Arg Ser Thr
1               5

<210> SEQ ID NO 41
<211> LENGTH: 54
<212> TYPE: DNA
<213> ORGANISM: Ecballium elaterium

<400> SEQUENCE: 41
ctaatgcgtt gcaaacagga ctccgactgc ctggctggct gcgtttgctg cgga          54

<210> SEQ ID NO 42
<211> LENGTH: 18
<212> TYPE: PRT
<213> ORGANISM: Ecballium elaterium

<400> SEQUENCE: 42

Leu Met Arg Cys Lys Gln Asp Ser Asp Ser Leu Ala Gly Cys Val Cys
1               5                   10                  15

Cys Gly

<210> SEQ ID NO 43
<211> LENGTH: 57
<212> TYPE: DNA
<213> ORGANISM: Ecballium elaterium

<400> SEQUENCE: 43
ctaatgcgtt gcaaacagga ctccgactgc ctggctggct gcgtttgctt ctgcgga       57

<210> SEQ ID NO 44
<211> LENGTH: 19
<212> TYPE: PRT
<213> ORGANISM: Ecballium elaterium

<400> SEQUENCE: 44

Leu Met Arg Cys Lys Gln Asp Ser Asp Ser Leu Ala Gly Cys Val Cys
1               5                   10                  15

Phe Cys Gly

<210> SEQ ID NO 45
<211> LENGTH: 69
<212> TYPE: DNA
<213> ORGANISM: Ecballium elaterium

<400> SEQUENCE: 45
ctaatgcgtt gcaaacagga ctccgactgc ctggctggct gcgtttgcgg gcccaacggt    60

```
ttctgcgga                                                             69
```

```
<210> SEQ ID NO 46
<211> LENGTH: 23
<212> TYPE: PRT
<213> ORGANISM: Ecballium elaterium

<400> SEQUENCE: 46

Leu Met Arg Cys Lys Gln Asp Ser Asp Cys Leu Ala Gly Ser Val Cys
1               5                   10                  15

Gly Pro Asn Gly Phe Cys Gly
            20

<210> SEQ ID NO 47
<211> LENGTH: 84
<212> TYPE: DNA
<213> ORGANISM: Ecballium elaterium

<400> SEQUENCE: 47
gggtgcccgc gaatcctaat gcgttgcaaa caggactccg actgcctggc tggctgcgtt    60
tgcgggccca acggtttctg cgga                                           84

<210> SEQ ID NO 48
<211> LENGTH: 28
<212> TYPE: PRT
<213> ORGANISM: Ecballium elaterium

<400> SEQUENCE: 48

Gly Cys Pro Arg Ile Leu Met Arg Cys Lys Gln Asp Ser Asp Cys Leu
1               5                   10                  15

Ala Gly Cys Val Cys Gly Pro Asn Gly Phe Cys Gly
            20                  25

<210> SEQ ID NO 49
<211> LENGTH: 1161
<212> TYPE: DNA
<213> ORGANISM: E.coli

<400> SEQUENCE: 49
atgaaaattg aagaaggcaa actggtgatt tggattaacg gcgataaagg ctataacggc    60
ctggcggaag tggcaaaaaa atttgaaaaa gataccggca ttaaagtgac cgtggaacat   120
ccggataaac tggaagaaaa atttccgcag gtggcggcga ccggcgatgg cccggatatt   180
attttttggg cgcatgatcg ctttggcggc tatgcgcaga gcggcctgct ggcggaaatt   240 acccccggata agcgtttca ggataaactg tatccgttta cctgggatgc ggtgcgctat   300
aacggcaaac tgattgcgta tccgattgcg gtggaagcgc tgagcctgat ttataacaaa   360
gatctgctgc cgaacccgcc gaaaacctgg gaagaaattc cggcgctgga taagaactg   420 aaagcgaaag caaaagcgc gctgatgttt aacctgcagg aaccgtattt acctggccg    480 ctgattgcgg cggatggcgg ctatgcgttt aaatatgaaa acggcaaata tgatattaaa   540
gatgtgggcg tggataacgc gggcgcgaaa gcgggcctga cctttctggt ggatctgatt   600
aaaaacaaac atatgaacgc ggataccgat tatagcattg cggaagcggc gtttaacaaa   660
ggcgaaaccg cgatgaccat taacggcccg tgggcgtgga gcaacattga tccagcaaa   720 gtgaactatg gcgtgaccgt gctgccgacc tttaaaggcc agccgagcaa accgtttgtg   780
ggcgtgctga cgcgggcat taacgcgcg agcccgaaca aagaactggc gaaagaattt   840
ctggaaaact atctgctgac cgatgaaggc ctggaagcgg tgaacaaaga taaaccgctg   900
```

```
ggcgcggtgg cgctgaaaag ctatgaagaa gaactggcga agatccgcg cattgcggcg      960 accatggaaa acgcgcagaa aggcgaaatt atgccgaaca ttccgcagat gagcgcgttt    1020
tggtatgcgg tgcgcaccgc ggtgattaac gcggcgagcg ccgccagac cgtggatgaa    1080 gcgctgaaag atgcgcagac caacagcagc agcaacaaca acaacaacaa caacaacaac    1140
aacctgggca ttgaaggccg c                                              1161
```

```
<210> SEQ ID NO 50
<211> LENGTH: 387
<212> TYPE: PRT
<213> ORGANISM: E. coli

<400> SEQUENCE: 50
```

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320
```

```
Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
    370                 375                 380

Glu Gly Arg
385

<210> SEQ ID NO 51
<211> LENGTH: 720
<212> TYPE: DNA
<213> ORGANISM: Aequorea victoria

<400> SEQUENCE: 51
atgagtaaag gagaagaact tttcactgga gttgtcccaa ttcttgttga attagatggt    60
gatgttaatg ggcacaaatt ttctgtcagt ggagagggtg aaggtgatgc aacatacgga   120
aaacttaccc ttaaatttat ttgcactact ggaaaactac ctgttccatg gccaacactt   180
gtcactactt tctcttatgg tgttcaatgc ttttcccgtt atccggatca tatgaaacgg   240
catgactttt tcaagagtgc catgcccgaa ggttatgtac aggaacgcac tatatctttc   300
aaagatgacg ggaactacaa gacgcgtgct gaagtcaagt ttgaaggtga taccttgtt   360 aatcgtatcg agttaaaagg tattgatttt aaagaagatg aaacattct cggacacaaa   420 ctcgagtaca actataactc acacaatgta tacatcacgg cagacaaaca aaagaatgga   480
atcaaagcta acttcaaaat tcgccacaac attgaagatg gatccgttca actagcagac   540
cattatcaac aaaatactcc aattggcgat ggccctgtcc ttttaccaga caaccattac   600
ctgtcgacac aatctgccct ttcgaaagat cccaacgaaa agcgtgacca catggtcctt   660
cttgagtttg taactgctgc tgggattaca catggcatgg atgagctcta caataatga   720

<210> SEQ ID NO 52
<211> LENGTH: 238
<212> TYPE: PRT
<213> ORGANISM: Aequorea victoria

<400> SEQUENCE: 52

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125
```

-continued

```
Asp Phe Lys Glu Asp Gly Asn Ile Leu Gly His Lys Leu Glu Tyr Asn
        130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 53
<211> LENGTH: 78
<212> TYPE: DNA
<213> ORGANISM: H. sapiens

<400> SEQUENCE: 53
cagtgcaggg tgacccaccc caacccgcgc ggcgtgagcg ccctgatgag gagcaccacc    60
aagaccagcg gccccagg    78

<210> SEQ ID NO 54
<211> LENGTH: 75
<212> TYPE: DNA
<213> ORGANISM: H. sapiens

<400> SEQUENCE: 54
cagtgcaggg tgacccaccc cccgcgcggc gtgagcgccc tgatgaggag caccaccaag    60
accagcggcc ccagg    75

<210> SEQ ID NO 55
<211> LENGTH: 75
<212> TYPE: DNA
<213> ORGANISM: H. sapiens

<400> SEQUENCE: 55
cagtgcaggg tgacccaccc caacccgcgc ggcgtggccc tgatgaggag caccaccaag    60
accagcggcc ccagg    75

<210> SEQ ID NO 56
<211> LENGTH: 72
<212> TYPE: DNA
<213> ORGANISM: H. sapiens

<400> SEQUENCE: 56
cagtgcaggg tgacccaccc cccgcgcggc gtggccctga tgaggagcac caccaagacc    60
agcggcccca gg    72

<210> SEQ ID NO 57
<211> LENGTH: 26
<212> TYPE: PRT
<213> ORGANISM: H. sapiens

<400> SEQUENCE: 57

```
Gln Cys Arg Val Thr His Pro Asn Pro Arg Val Val Ser Ala Leu Met
1               5                   10                  15
```

```
Arg Ser Thr Thr Lys Thr Ser Gly Pro Arg
            20                  25

<210> SEQ ID NO 58
<211> LENGTH: 25
<212> TYPE: PRT
<213> ORGANISM: H. sapiens

<400> SEQUENCE: 58

Gln Cys Arg Val Thr His Pro Pro Arg Val Val Ser Ala Leu Met Arg
1               5                   10                  15

Ser Thr Thr Lys Thr Ser Gly Pro Arg
            20                  25

<210> SEQ ID NO 59
<211> LENGTH: 25
<212> TYPE: PRT
<213> ORGANISM: H. sapiens

<400> SEQUENCE: 59

Gln Cys Arg Val Thr His Pro Asn Pro Arg Val Val Ala Leu Met Arg
1               5                   10                  15

Ser Thr Thr Lys Thr Ser Gly Pro Arg
            20                  25

<210> SEQ ID NO 60
<211> LENGTH: 24
<212> TYPE: PRT
<213> ORGANISM: H. sapiens

<400> SEQUENCE: 60

Gln Cys Arg Val Thr His Pro Pro Arg Val Val Ala Leu Met Arg Ser
1               5                   10                  15

Thr Thr Lys Thr Ser Gly Pro Arg
            20

<210> SEQ ID NO 61
<211> LENGTH: 63
<212> TYPE: DNA
<213> ORGANISM: H.sapines

<400> SEQUENCE: 61
caccccaacc cgcgcggcgt gagcgccctg atgaggagca ccaccaagac cagcggcccc    60
agg                                                                 63

<210> SEQ ID NO 62
<211> LENGTH: 60
<212> TYPE: DNA
<213> ORGANISM: H. sapiens

<400> SEQUENCE: 62
caccccccgc gcggcgtgag cgccctgatg aggagcacca ccaagaccag cggccccagg    60

<210> SEQ ID NO 63
<211> LENGTH: 60
<212> TYPE: DNA
<213> ORGANISM: H. sapiens

<400> SEQUENCE: 63
caccccaacc cgcgcggcgt ggccctgatg aggagcacca ccaagaccag cggccccagg    60
```

```
<210> SEQ ID NO 64
<211> LENGTH: 57
<212> TYPE: DNA
<213> ORGANISM: H. sapiens

<400> SEQUENCE: 64
caccccccgc gcggcgtggc cctgatgagg agcaccacca agaccagcgg ccccagg      57

<210> SEQ ID NO 65
<211> LENGTH: 21
<212> TYPE: PRT
<213> ORGANISM: h. SAPIENS

<400> SEQUENCE: 65

His Pro Asn Pro Arg Gly Val Ser Ala Leu Met Arg Ser Thr Thr Lys
1               5                   10                  15

Thr Ser Gly Pro Arg
            20

<210> SEQ ID NO 66
<211> LENGTH: 20
<212> TYPE: PRT
<213> ORGANISM: H. sapiens

<400> SEQUENCE: 66

His Pro Pro Arg Gly Val Ser Ala Leu Met Arg Ser Thr Thr Lys Thr
1               5                   10                  15

Ser Gly Pro Arg
            20

<210> SEQ ID NO 67
<211> LENGTH: 20
<212> TYPE: PRT
<213> ORGANISM: H. sapiens

<400> SEQUENCE: 67

His Pro Asn Pro Arg Gly Val Ala Leu Met Arg Ser Thr Thr Lys Thr
1               5                   10                  15

Ser Gly Pro Arg
            20

<210> SEQ ID NO 68
<211> LENGTH: 19
<212> TYPE: PRT
<213> ORGANISM: H. sapiens

<400> SEQUENCE: 68

His Pro Pro Arg Gly Val Ala Leu Met Arg Ser Thr Thr Lys Thr Ser
1               5                   10                  15

Gly Pro Arg

<210> SEQ ID NO 69
<211> LENGTH: 105
<212> TYPE: DNA
<213> ORGANISM: H. sapiens

<400> SEQUENCE: 69
gagggcgaga cctaccagtg cagggtgacc caccccaacc cgcgcggcgt gagccacctg      60
cccagggccc tgatgaggag caccaccaag accagcggcc ccagg                    105

<210> SEQ ID NO 70
<211> LENGTH: 102
```

```
<212> TYPE: DNA
<213> ORGANISM: H. sapiens

<400> SEQUENCE: 70
gagggcgaga cctaccagtg cagggtgacc caccccccgc gcggcgtgag ccacctgccc    60
agggccctga tgaggagcac caccaagacc agcggcccca gg                     102

<210> SEQ ID NO 71
<211> LENGTH: 102
<212> TYPE: DNA
<213> ORGANISM: H. sapiens

<400> SEQUENCE: 71
gagggcgaga cctaccagtg cagggtgacc caccccaacc cgcgcggcgt gcacctgccc    60
agggccctga tgaggagcac caccaagacc agcggcccca gg                     102

<210> SEQ ID NO 72
<211> LENGTH: 99
<212> TYPE: DNA
<213> ORGANISM: H. sapiens

<400> SEQUENCE: 72
gagggcgaga cctaccagtg cagggtgacc caccccccgc gcggcgtgca cctgcccagg    60
gccctgatga ggagcaccac caagaccagc ggccccagg                          99

<210> SEQ ID NO 73
<211> LENGTH: 31
<212> TYPE: PRT
<213> ORGANISM: H. sapiens

<400> SEQUENCE: 73

Glu Gly Glu Thr Tyr Gln Cys Arg Val Thr His Pro Asn Pro Arg Gly
1               5                   10                  15
Val Ser Ala Leu Met Arg Ser Thr Thr Lys Thr Ser Gly Pro Arg
            20                  25                  30

<210> SEQ ID NO 74
<211> LENGTH: 30
<212> TYPE: PRT
<213> ORGANISM: H. sapiens

<400> SEQUENCE: 74

Glu Gly Glu Thr Tyr Gln Cys Arg Val Thr His Pro Pro Arg Gly Val
1               5                   10                  15
Ser Ala Leu Met Arg Ser Thr Thr Lys Thr Ser Gly Pro Arg
            20                  25                  30

<210> SEQ ID NO 75
<211> LENGTH: 30
<212> TYPE: PRT
<213> ORGANISM: H. sapiens

<400> SEQUENCE: 75

Glu Gly Glu Thr Tyr Gln Cys Arg Val Thr His Pro Asn Pro Arg Gly
1               5                   10                  15
Val Ala Leu Met Arg Ser Thr Thr Lys Thr Ser Gly Pro Arg
            20                  25                  30

<210> SEQ ID NO 76
<211> LENGTH: 29
<212> TYPE: PRT
```

<213> ORGANISM: H. sapiens

<400> SEQUENCE: 76

Glu Gly Glu Thr Tyr Gln Cys Arg Val Thr His Pro Pro Arg Gly Val
1               5                   10                  15

Ala Leu Met Arg Ser Thr Thr Lys Thr Ser Gly Pro Arg
            20                  25

<210> SEQ ID NO 77
<211> LENGTH: 78
<212> TYPE: DNA
<213> ORGANISM: H. sapiens

<400> SEQUENCE: 77
cagtgcaggg tgacccaccc cgtggatctg gcgccgagcg ccctgatgag gagcaccacc    60
aagaccagcg gccccagg                                                 78

<210> SEQ ID NO 78
<211> LENGTH: 75
<212> TYPE: DNA
<213> ORGANISM: H. sapiens

<400> SEQUENCE: 78
cagtgcaggg tgacccaccc cgatctggcg ccgagcgccc tgatgaggag caccaccaag    60
accagcggcc ccagg                                                    75

<210> SEQ ID NO 79
<211> LENGTH: 75
<212> TYPE: DNA
<213> ORGANISM: H. sapiens

<400> SEQUENCE: 79
cagtgcaggg tgacccaccc cgtggatctg gcgccggccc tgatgaggag caccaccaag    60
accagcggcc ccagg                                                    75

<210> SEQ ID NO 80
<211> LENGTH: 72
<212> TYPE: DNA
<213> ORGANISM: H. sapiens

<400> SEQUENCE: 80
cagtgcaggg tgacccaccc cgatctggcg ccggccctga tgaggagcac caccaagacc    60
agcggcccca gg                                                       72

<210> SEQ ID NO 81
<211> LENGTH: 25
<212> TYPE: PRT
<213> ORGANISM: H. sapiens

<400> SEQUENCE: 81

Gln Cys Arg Val Thr His Pro Asp Leu Ala Pro Ser Ala Leu Met Arg
1               5                   10                  15

Ser Thr Thr Lys Thr Ser Gly Pro Arg
            20                  25

<210> SEQ ID NO 82
<211> LENGTH: 25
<212> TYPE: PRT
<213> ORGANISM: H. sapiens

<400> SEQUENCE: 82

Gln Cys Arg Val Thr His Pro Val Asp Leu Ala Pro Ala Leu Met Arg
1               5                   10                  15

Ser Thr Thr Lys Thr Ser Gly Pro Arg
            20                  25

<210> SEQ ID NO 83
<211> LENGTH: 25
<212> TYPE: PRT
<213> ORGANISM: H. sapiens

<400> SEQUENCE: 83

Gln Cys Arg Val Thr His Pro Val Asp Leu Ala Pro Ala Leu Met Arg
1               5                   10                  15

Ser Thr Thr Lys Thr Ser Gly Pro Arg
            20                  25

<210> SEQ ID NO 84
<211> LENGTH: 24
<212> TYPE: PRT
<213> ORGANISM: H. sapiens

<400> SEQUENCE: 84

Gln Cys Arg Val Thr His Pro Asp Leu Ala Pro Ala Leu Met Arg Ser
1               5                   10                  15

Thr Thr Lys Thr Ser Gly Pro Arg
            20

<210> SEQ ID NO 85
<211> LENGTH: 63
<212> TYPE: DNA
<213> ORGANISM: H. sapiens

<400> SEQUENCE: 85 cacccegtgg atctggcgcc gagcgccctg atgaggagca ccaccaagac cagcggcccc      60
agg                                                                   63

<210> SEQ ID NO 86
<211> LENGTH: 60
<212> TYPE: DNA
<213> ORGANISM: H. sapiens

<400> SEQUENCE: 86 cacccegatc tggcgccgag cgccctgatg aggagcacca ccaagaccag cggccccagg      60

<210> SEQ ID NO 87
<211> LENGTH: 60
<212> TYPE: DNA
<213> ORGANISM: H. sapiens

<400> SEQUENCE: 87 cacccegtgg atctggcgcc ggccctgatg aggagcacca ccaagaccag cggccccagg      60

<210> SEQ ID NO 88
<211> LENGTH: 57
<212> TYPE: DNA
<213> ORGANISM: H. sapiens

<400> SEQUENCE: 88 cacccegatc tggcgccggc cctgatgagg agcaccacca agaccagcgg ccccagg         57

<210> SEQ ID NO 89

<211> LENGTH: 21
<212> TYPE: PRT
<213> ORGANISM: H. sapiens

<400> SEQUENCE: 89

His Pro Val Asp Leu Ala Pro Ser Ala Leu Met Arg Ser Thr Thr Lys
1               5                   10                  15

Thr Ser Gly Pro Arg
            20

<210> SEQ ID NO 90
<211> LENGTH: 20
<212> TYPE: PRT
<213> ORGANISM: H. sapiens

<400> SEQUENCE: 90

His Pro Asp Leu Ala Pro Ser Ala Leu Met Arg Ser Thr Thr Lys Thr
1               5                   10                  15

Ser Gly Pro Arg
            20

<210> SEQ ID NO 91
<211> LENGTH: 20
<212> TYPE: PRT
<213> ORGANISM: H. sapiens

<400> SEQUENCE: 91

His Pro Val Asp Leu Ala Pro Ala Leu Met Arg Ser Thr Thr Lys Thr
1               5                   10                  15

Ser Gly Pro Arg
            20

<210> SEQ ID NO 92
<211> LENGTH: 19
<212> TYPE: PRT
<213> ORGANISM: H. sapiens

<400> SEQUENCE: 92

His Pro Asp Leu Ala Pro Ala Leu Met Arg Ser Thr Thr Lys Thr Ser
1               5                   10                  15

Gly Pro Arg

<210> SEQ ID NO 93
<211> LENGTH: 105
<212> TYPE: DNA
<213> ORGANISM: H. sapiens

<400> SEQUENCE: 93
gagggcgaga cctaccagtg cagggtgacc caccccgtgg atctggcgcc gagccacctg     60
cccagggccc tgatgaggag caccaccaag accagcggcc ccagg                    105

<210> SEQ ID NO 94
<211> LENGTH: 102
<212> TYPE: DNA
<213> ORGANISM: H. sapiens

<400> SEQUENCE: 94
gagggcgaga cctaccagtg cagggtgacc caccccgatc tggcgccgag ccacctgccc     60
agggccctga tgaggagcac caccaagacc agcggcccca gg                       102

<210> SEQ ID NO 95

```
<211> LENGTH: 102
<212> TYPE: DNA
<213> ORGANISM: H. sapiens

<400> SEQUENCE: 95
gagggcgaga cctaccagtg cagggtgacc caccccgtgg atctggcgcc gcacctgccc      60
agggccctga tgaggagcac caccaagacc agcggcccca gg                        102

<210> SEQ ID NO 96
<211> LENGTH: 99
<212> TYPE: DNA
<213> ORGANISM: H. sapiens

<400> SEQUENCE: 96
gagggcgaga cctaccagtg cagggtgacc caccccgatc tggcgccgca cctgcccagg      60
gccctgatga ggagcaccac caagaccagc ggccccagg                            99

<210> SEQ ID NO 97
<211> LENGTH: 31
<212> TYPE: PRT
<213> ORGANISM: H. sapiens

<400> SEQUENCE: 97

Glu Gly Glu Thr Tyr Gln Cys Arg Val Thr His Pro Val Asp Leu Ala
1               5                   10                  15
Pro Ser Ala Leu Met Arg Ser Thr Thr Lys Thr Ser Gly Pro Arg
            20                  25                  30

<210> SEQ ID NO 98
<211> LENGTH: 30
<212> TYPE: PRT
<213> ORGANISM: H. sapiens

<400> SEQUENCE: 98

Glu Gly Glu Thr Tyr Gln Cys Arg Val Thr His Pro Asp Leu Ala Pro
1               5                   10                  15
Ser Ala Leu Met Arg Ser Thr Thr Lys Thr Ser Gly Pro Arg
            20                  25                  30

<210> SEQ ID NO 99
<211> LENGTH: 30
<212> TYPE: PRT
<213> ORGANISM: H. sapiens

<400> SEQUENCE: 99

Glu Gly Glu Thr Tyr Gln Cys Arg Val Thr His Pro Val Asp Leu Ala
1               5                   10                  15
Pro Ala Leu Met Arg Ser Thr Thr Lys Thr Ser Gly Pro Arg
            20                  25                  30

<210> SEQ ID NO 100
<211> LENGTH: 29
<212> TYPE: PRT
<213> ORGANISM: H. sapiens

<400> SEQUENCE: 100

Glu Gly Glu Thr Tyr Gln Cys Arg Val Thr His Pro Asp Leu Ala Pro
1               5                   10                  15
Ala Leu Met Arg Ser Thr Thr Lys Thr Ser Gly Pro Arg
            20                  25
```

```
<210> SEQ ID NO 101
<211> LENGTH: 72
<212> TYPE: DNA
<213> ORGANISM: H. sapiens

<400> SEQUENCE: 101
cagtgcaggg tgacccaccc ccgcaacggc accgccctga tgaggagcac caccaagacc      60
agcggcccca gg                                                          72

<210> SEQ ID NO 102
<211> LENGTH: 57
<212> TYPE: DNA
<213> ORGANISM: H. sapiens

<400> SEQUENCE: 102
cacccccgca acggcaccgc cctgatgagg agcaccacca agaccagcgg ccccagg         57

<210> SEQ ID NO 103
<211> LENGTH: 99
<212> TYPE: DNA
<213> ORGANISM: H. sapiens

<400> SEQUENCE: 103
gagggcgaga cctaccagtg cagggtgacc cacccccgca acggcaccca cctgcccagg      60
gccctgatga ggagcaccac caagaccagc ggccccagg                             99

<210> SEQ ID NO 104
<211> LENGTH: 24
<212> TYPE: PRT
<213> ORGANISM: H. sapiens

<400> SEQUENCE: 104

Gln Cys Arg Val Thr His Pro Arg Asn Gly Thr Ala Leu Met Arg Ser
1               5                   10                  15

Thr Thr Lys Thr Ser Gly Pro Arg
            20

<210> SEQ ID NO 105
<211> LENGTH: 19
<212> TYPE: PRT
<213> ORGANISM: H. sapiens

<400> SEQUENCE: 105

His Pro Arg Asn Gly Thr Ala Leu Met Arg Ser Thr Thr Lys Thr Ser
1               5                   10                  15

Gly Pro Arg

<210> SEQ ID NO 106
<211> LENGTH: 29
<212> TYPE: PRT
<213> ORGANISM: H. sapiens

<400> SEQUENCE: 106

Glu Gly Glu Thr Tyr Gln Cys Arg Val Thr His Pro Arg Asn Gly Thr
1               5                   10                  15

Ala Leu Met Arg Ser Thr Thr Lys Thr Ser Gly Pro Arg
            20                  25

<210> SEQ ID NO 107
<211> LENGTH: 18
<212> TYPE: DNA
<213> ORGANISM: H. sapiens
```

<400> SEQUENCE: 107
catccgcatc tgccgcgc                                                 18

<210> SEQ ID NO 108
<211> LENGTH: 6
<212> TYPE: PRT
<213> ORGANISM: H. sapiens

<400> SEQUENCE: 108

His Pro His Leu Pro Arg
1               5

<210> SEQ ID NO 109
<211> LENGTH: 18
<212> TYPE: DNA
<213> ORGANISM: H. sapiens

<400> SEQUENCE: 109
aacccgcgcg gcgtgagc                                                 18

<210> SEQ ID NO 110
<211> LENGTH: 6
<212> TYPE: PRT
<213> ORGANISM: H. sapiens

<400> SEQUENCE: 110

Asn Pro Arg Gly Val Ser
1               5

<210> SEQ ID NO 111
<211> LENGTH: 12
<212> TYPE: DNA
<213> ORGANISM: H. sapiens

<400> SEQUENCE: 111
ccgcgcggcg tg                                                       12

<210> SEQ ID NO 112
<211> LENGTH: 4
<212> TYPE: PRT
<213> ORGANISM: H. sapiens

<400> SEQUENCE: 112

Pro Arg Gly Val
1

<210> SEQ ID NO 113
<211> LENGTH: 18
<212> TYPE: DNA
<213> ORGANISM: H. sapiens

<400> SEQUENCE: 113
gtggatctgg cgccgagc                                                 18

<210> SEQ ID NO 114
<211> LENGTH: 6
<212> TYPE: PRT
<213> ORGANISM: H. sapiens

<400> SEQUENCE: 114

Val Asp Leu Ala Pro Ser
1               5

```
<210> SEQ ID NO 115
<211> LENGTH: 15
<212> TYPE: DNA
<213> ORGANISM: H. sapiens

<400> SEQUENCE: 115
gatctggcgc cgagc                                                    15

<210> SEQ ID NO 116
<211> LENGTH: 15
<212> TYPE: DNA
<213> ORGANISM: H. sapiens

<400> SEQUENCE: 116
gtggatctgg cgccg                                                    15

<210> SEQ ID NO 117
<211> LENGTH: 12
<212> TYPE: DNA
<213> ORGANISM: H. sapiens

<400> SEQUENCE: 117
gatctggcgc cg                                                       12

<210> SEQ ID NO 118
<211> LENGTH: 5
<212> TYPE: PRT
<213> ORGANISM: H. sapiens

<400> SEQUENCE: 118

Asp Leu Ala Pro Ser
1               5

<210> SEQ ID NO 119
<211> LENGTH: 5
<212> TYPE: PRT
<213> ORGANISM: H. sapiens

<400> SEQUENCE: 119

Val Asp Leu Ala Pro
1               5

<210> SEQ ID NO 120
<211> LENGTH: 4
<212> TYPE: PRT
<213> ORGANISM: H. sapiens

<400> SEQUENCE: 120

Asp Leu Ala Pro
1

<210> SEQ ID NO 121
<211> LENGTH: 18
<212> TYPE: DNA
<213> ORGANISM: H. sapiens

<400> SEQUENCE: 121
cagcgcaacg gcaccctg                                                 18

<210> SEQ ID NO 122
<211> LENGTH: 12
<212> TYPE: DNA
<213> ORGANISM: H. sapiens
```

```
<400> SEQUENCE: 122
cgcaacggca cc                                                            12

<210> SEQ ID NO 123
<211> LENGTH: 6
<212> TYPE: PRT
<213> ORGANISM: H. sapiens

<400> SEQUENCE: 123

Gln Arg Asn Gly Thr Leu
1               5

<210> SEQ ID NO 124
<211> LENGTH: 4
<212> TYPE: PRT
<213> ORGANISM: H. sapiens

<400> SEQUENCE: 124

Arg Asn Gly Thr
1

<210> SEQ ID NO 125
<211> LENGTH: 21
<212> TYPE: DNA
<213> ORGANISM: H. sapiens

<400> SEQUENCE: 125
accaaaacca gcggcccgcg c                                                  21

<210> SEQ ID NO 126
<211> LENGTH: 7
<212> TYPE: PRT
<213> ORGANISM: H. sapiens

<400> SEQUENCE: 126

Thr Lys Thr Ser Gly Pro Arg
1               5

<210> SEQ ID NO 127
<211> LENGTH: 24
<212> TYPE: DNA
<213> ORGANISM: Ecballium elaterium

<400> SEQUENCE: 127
tgcgggccca acggtttctg cgga                                               24

<210> SEQ ID NO 128
<211> LENGTH: 6
<212> TYPE: PRT
<213> ORGANISM: Ecballium elaterium

<400> SEQUENCE: 128

Cys Gly Pro Asn Phe Cys
1               5

<210> SEQ ID NO 129
<211> LENGTH: 6
<212> TYPE: PRT
<213> ORGANISM: Mus musculus

<400> SEQUENCE: 129

Glu Pro Arg Gly Val Ile
1               5
```

<210> SEQ ID NO 130
<211> LENGTH: 4
<212> TYPE: PRT
<213> ORGANISM: Mus musculus

<400> SEQUENCE: 130

Asp Leu Ala Glu
1

<210> SEQ ID NO 131
<211> LENGTH: 5
<212> TYPE: PRT
<213> ORGANISM: Mus musculus

<400> SEQUENCE: 131

Asn Asn Ala Thr Leu
1               5

<210> SEQ ID NO 132
<211> LENGTH: 4
<212> TYPE: PRT
<213> ORGANISM: Mus musculus

<400> SEQUENCE: 132

Asp Phe Pro Lys
1

<210> SEQ ID NO 133
<211> LENGTH: 6
<212> TYPE: PRT
<213> ORGANISM: H. sapiens

<400> SEQUENCE: 133

Thr Phe Glu Asp Ser Thr
1               5

<210> SEQ ID NO 134
<211> LENGTH: 4
<212> TYPE: PRT
<213> ORGANISM: H. sapiens

<400> SEQUENCE: 134

Ala Tyr Leu Ser
1

<210> SEQ ID NO 135
<211> LENGTH: 83
<212> TYPE: DNA
<213> ORGANISM: Ecballium elaterium

<400> SEQUENCE: 135
gcggccgcct aatgcgttgc aaacaggact ccgactgcct ggctggctgc gtttgcgggc      60
ccaacggttt ctgcggagaa ttc                                             83

<210> SEQ ID NO 136
<211> LENGTH: 34
<212> TYPE: PRT
<213> ORGANISM: H. sapiens

<400> SEQUENCE: 136

Thr Met Ile Thr Pro Ser Leu Gln Cys Arg Val Thr Met Pro Ala Leu
1               5                   10                  15

Met Ser Thr Thr Lys Thr Ser Gly Pro Arg Val Pro Val Glu Lys Met

-continued

```
                 20                  25                  30

Ser Lys

<210> SEQ ID NO 137
<211> LENGTH: 40
<212> TYPE: PRT
<213> ORGANISM: H. sapiens

<400> SEQUENCE: 137

Thr Met Ile Thr Pro Ser Leu Gln Cys Arg Val Thr Met Pro Glu Pro
1               5                  10                  15

Arg Gly Val Ile Ala Leu Met Ser Thr Thr Lys Thr Ser Gly Pro Arg
                20                  25                  30

Val Pro Val Glu Lys Met Ser Lys
        35                  40

<210> SEQ ID NO 138
<211> LENGTH: 38
<212> TYPE: PRT
<213> ORGANISM: H. sapiens

<400> SEQUENCE: 138

Thr Met Ile Thr Pro Ser Leu Gln Cys Arg Val Thr Met Pro Asp Leu
1               5                  10                  15

Ala Glu Ala Leu Met Ser Thr Thr Lys Thr Ser Gly Pro Arg Val Pro
                20                  25                  30

Val Glu Lys Met Ser Lys
        35

<210> SEQ ID NO 139
<211> LENGTH: 38
<212> TYPE: PRT
<213> ORGANISM: H. sapiens

<400> SEQUENCE: 139

Thr Met Ile Thr Pro Ser Leu Gln Cys Arg Val Thr Met Pro Asn Asn
1               5                  10                  15

Ala Thr Ala Leu Met Ser Thr Thr Lys Thr Ser Gly Pro Arg Val Pro
                20                  25                  30

Val Glu Lys Met Ser Lys
        35

<210> SEQ ID NO 140
<211> LENGTH: 38
<212> TYPE: PRT
<213> ORGANISM: H. sapiens

<400> SEQUENCE: 140

Thr Met Ile Thr Pro Ser Leu Gln Cys Arg Val Thr Met Pro Asp Phe
1               5                  10                  15

Pro Lys Ala Leu Met Ser Thr Thr Lys Thr Ser Gly Pro Arg Val Pro
                20                  25                  30

Val Glu Lys Met Ser Lys
        35

<210> SEQ ID NO 141
<211> LENGTH: 71
<212> TYPE: DNA
<213> ORGANISM: EE+IGE

<400> SEQUENCE: 141
```

```
cgccaagctt ggggtgcgat tccaacccga gaggggtgag ctgcaaacag gactccgact    60
gcctggctgg c                                                          71

<210> SEQ ID NO 142
<211> LENGTH: 71
<212> TYPE: DNA
<213> ORGANISM: EE+IGE

<400> SEQUENCE: 142
tcataagctt cggatctctt aatccgcaga aaccgttggg cccgcaaacg cagccagcca    60
ggcagtcgga g                                                          71

<210> SEQ ID NO 143
<211> LENGTH: 73
<212> TYPE: DNA
<213> ORGANISM: EE+IGE

<400> SEQUENCE: 143
cgccaagctt ggggtgcccg cgaatcctaa tgcgttgcga ttccaacccg agaggggtga    60
gctgcctggc tgg                                                        73

<210> SEQ ID NO 144
<211> LENGTH: 72
<212> TYPE: DNA
<213> ORGANISM: EE+IGE

<400> SEQUENCE: 144
tcataagctt cggatctctt aatccgcaga aaccgttggg cccgcaaacg cagccagcca    60
ggcagctcac cc                                                         72

<210> SEQ ID NO 145
<211> LENGTH: 75
<212> TYPE: DNA
<213> ORGANISM: EE+IGE

<400> SEQUENCE: 145
cgccaagctt ggggtgcccg cgaatcctaa tgcgttgcaa acaggactcc gactgcgatt    60
ccaacccgag agggg                                                      75

<210> SEQ ID NO 146
<211> LENGTH: 76
<212> TYPE: DNA
<213> ORGANISM: EE+IGE

<400> SEQUENCE: 146
tcataagctt cggatctctt aatccgcaga aaccgttggg cccgcaaacg cagctcaccc    60
ctctcgggtt ggaatc                                                     76

<210> SEQ ID NO 147
<211> LENGTH: 73
<212> TYPE: DNA
<213> ORGANISM: EE+IGE

<400> SEQUENCE: 147
cgccaagctt ggggtgcccg cgaatcctaa tgcgttgcaa acaggactcc gactgcctgg    60
ctggctgcgt ttg                                                        73

<210> SEQ ID NO 148
```

```
<211> LENGTH: 74
<212> TYPE: DNA
<213> ORGANISM: EE+IGE

<400> SEQUENCE: 148
tcataagctt cggatctctt aatccgcagc tcacccctct cgggttggaa tcgcaaacgc    60
agccagccag gcag                                                     74

<210> SEQ ID NO 149
<211> LENGTH: 46
<212> TYPE: DNA
<213> ORGANISM: EE+IGE

<400> SEQUENCE: 149
caagctttgg gtgccaaaga aacggtactc tttgcaaaca ggactc                  46

<210> SEQ ID NO 150
<211> LENGTH: 46
<212> TYPE: DNA
<213> ORGANISM: EE+IGE

<400> SEQUENCE: 150
gagtcctgtt tgcaaagagt accgtttctt tggcacccca agcttg                  46

<210> SEQ ID NO 151
<211> LENGTH: 46
<212> TYPE: DNA
<213> ORGANISM: EE+IGE

<400> SEQUENCE: 151
caagctttgg gtgcgttgat cttgctccat cttgcaaaca ggactc                  46

<210> SEQ ID NO 152
<211> LENGTH: 46
<212> TYPE: DNA
<213> ORGANISM: EE+IGE

<400> SEQUENCE: 152
gagtcctgtt tgcaagatgg agcaagatca acgcacccca agcttg                  46

<210> SEQ ID NO 153
<211> LENGTH: 45
<212> TYPE: DNA
<213> ORGANISM: EE+IGE

<400> SEQUENCE: 153
cctaatgcgt tgccaaagaa acggtactct ttgcctggct ggctg                   45

<210> SEQ ID NO 154
<211> LENGTH: 45
<212> TYPE: DNA
<213> ORGANISM: EE+IGE

<400> SEQUENCE: 154
cagccagcca ggcaaagagt accgtttctt tggcaacgca ttagg                   45

<210> SEQ ID NO 155
<211> LENGTH: 45
<212> TYPE: DNA
<213> ORGANISM: EE+IGE

<400> SEQUENCE: 155
cctaatgcgt tgcgttgatc ttgctccatc ttgcctggct ggctg                   45
```

<210> SEQ ID NO 156
<211> LENGTH: 45
<212> TYPE: DNA
<213> ORGANISM: EE+IGE

<400> SEQUENCE: 156
cagccagcca ggcaagatgg agcaagatca acgcaacgca ttagg            45

<210> SEQ ID NO 157
<211> LENGTH: 44
<212> TYPE: DNA
<213> ORGANISM: EE+IGE

<400> SEQUENCE: 157
ggactccgac tgccaaagaa acggtactct ttgcgtttgc gggc             44

<210> SEQ ID NO 158
<211> LENGTH: 44
<212> TYPE: DNA
<213> ORGANISM: EE+IGE

<400> SEQUENCE: 158
gcccgcaaac gcaaagagta ccgtttcttt ggcagtcgga gtcc             44

<210> SEQ ID NO 159
<211> LENGTH: 44
<212> TYPE: DNA
<213> ORGANISM: EE+IGE

<400> SEQUENCE: 159
ggactccgac tgcgttgatc ttgctccatc ttgcgtttgc gggc             44

<210> SEQ ID NO 160
<211> LENGTH: 44
<212> TYPE: DNA
<213> ORGANISM: EE+IGE

<400> SEQUENCE: 160
gcccgcaaac gcaagatgga gcaagatcaa cgcagtcgga gtcc             44

<210> SEQ ID NO 161
<211> LENGTH: 46
<212> TYPE: DNA
<213> ORGANISM: EE+IGE

<400> SEQUENCE: 161
ctggctgcgt tgccaaaga aacggtactc tttgcggagg aggacc            46

<210> SEQ ID NO 162
<211> LENGTH: 46
<212> TYPE: DNA
<213> ORGANISM: EE+IGE

<400> SEQUENCE: 162
ggtcctcctc cgcaaagagt accgtttctt tggcaaacgc agccag           46

<210> SEQ ID NO 163
<211> LENGTH: 46
<212> TYPE: DNA
<213> ORGANISM: EE+IGE

<400> SEQUENCE: 163
ctggctgcgt ttgcgttgat cttgctccat cttgcggagg aggacc					46

<210> SEQ ID NO 164
<211> LENGTH: 46
<212> TYPE: DNA
<213> ORGANISM: EE+IGE

<400> SEQUENCE: 164
ggtcctcctc cgcaagatgg agcaagatca acgcaaacgc agccag					46

<210> SEQ ID NO 165
<211> LENGTH: 30
<212> TYPE: DNA
<213> ORGANISM: EE+IGE

<400> SEQUENCE: 165
gatcgcggcc gcgggtgccc gcgaatccta					30

<210> SEQ ID NO 166
<211> LENGTH: 28
<212> TYPE: DNA
<213> ORGANISM: EE+IGE

<400> SEQUENCE: 166
gatcgaattc tccgcagaaa ccgttggg					28

<210> SEQ ID NO 167
<211> LENGTH: 30
<212> TYPE: DNA
<213> ORGANISM: EE+IGE

<400> SEQUENCE: 167
gatcgcggcc gcgggtgcca agaaacggt					30

<210> SEQ ID NO 168
<211> LENGTH: 18
<212> TYPE: DNA
<213> ORGANISM: EE+IGE

<400> SEQUENCE: 168
gggtgcgttg atcttgct					18

<210> SEQ ID NO 169
<211> LENGTH: 18
<212> TYPE: DNA
<213> ORGANISM: EE+IGE

<400> SEQUENCE: 169
gggtgctgca aacaggac					18

<210> SEQ ID NO 170
<211> LENGTH: 18
<212> TYPE: DNA
<213> ORGANISM: EE+IGE

<400> SEQUENCE: 170
tccgcaaaga gtaccgtt					18

<210> SEQ ID NO 171
<211> LENGTH: 26
<212> TYPE: DNA
<213> ORGANISM: EE+IGE

<400> SEQUENCE: 171

-continued

```
gatcgaattc tccgcaagat ggagca                                           26

<210> SEQ ID NO 172
<211> LENGTH: 26
<212> TYPE: DNA
<213> ORGANISM: EE+IGE

<400> SEQUENCE: 172
gatcgaattc tccgcaagat ggagca                                           26

<210> SEQ ID NO 173
<211> LENGTH: 25
<212> TYPE: DNA
<213> ORGANISM: EE+IGE

<400> SEQUENCE: 173
gatcgcggcc gcttgcaaac aggac                                            25

<210> SEQ ID NO 174
<211> LENGTH: 32
<212> TYPE: DNA
<213> ORGANISM: EE+IGE

<400> SEQUENCE: 174
gatcgaattc tccgcagcaa acgcagccag cc                                    32

<210> SEQ ID NO 175
<211> LENGTH: 54
<212> TYPE: DNA
<213> ORGANISM: EE+IGE

<400> SEQUENCE: 175
ctaatgcgtt gcaaacagga ctccgactgc ctggctggct gcgtttgctg cgga            54

<210> SEQ ID NO 176
<211> LENGTH: 33
<212> TYPE: DNA
<213> ORGANISM: EE+IGE

<400> SEQUENCE: 176
gatcgcggcc gcctaatgcg ttgcaaacag gac                                   33

<210> SEQ ID NO 177
<211> LENGTH: 32
<212> TYPE: DNA
<213> ORGANISM: EE+IGE

<400> SEQUENCE: 177
gatcgaattc tccgcagcaa acgcagccag cc                                    32

<210> SEQ ID NO 178
<211> LENGTH: 60
<212> TYPE: DNA
<213> ORGANISM: EE+IGE

<400> SEQUENCE: 178
ctaatgcgtt gcaaacagga ctccgactgc ctggctggct gcgtttgctg cggagaattc      60

<210> SEQ ID NO 179
<211> LENGTH: 72
<212> TYPE: DNA
<213> ORGANISM: EE+IGE
```

<400> SEQUENCE: 179
ggctgcgttt gcgattccaa cccgagaggg gtgagcgcct acctaagccg gcccagcccg    60
tgcggagaat tc                                                       72

<210> SEQ ID NO 180
<211> LENGTH: 17
<212> TYPE: PRT
<213> ORGANISM: EE+IGE

<400> SEQUENCE: 180

Asp Ser Asn Pro Arg Gly Val Ser Ala Tyr Leu Ser Arg Pro Ser Pro
1               5                   10                  15

Cys

<210> SEQ ID NO 181
<211> LENGTH: 60
<212> TYPE: DNA
<213> ORGANISM: EE+IGE

<400> SEQUENCE: 181
gattccaacc cgagaggggt gagcgcctac ctaagccggc ccagcccgtg cggagaattc    60

<210> SEQ ID NO 182
<211> LENGTH: 72
<212> TYPE: DNA
<213> ORGANISM: EE+IGE

<400> SEQUENCE: 182
gaattctccg cacgggctgg gccggcttag gtaggcgctc acccctctcg ggttggaatc    60
gcaaacgcag cc                                                       72

<210> SEQ ID NO 183
<211> LENGTH: 17
<212> TYPE: PRT
<213> ORGANISM: EE+IGE

<400> SEQUENCE: 183

Pro Ser Pro Arg Ser Leu Tyr Ala Ser Val Gly Arg Pro Asn Ser Asp
1               5                   10                  15

Cys

<210> SEQ ID NO 184
<211> LENGTH: 60
<212> TYPE: DNA
<213> ORGANISM: EE+IGE

<400> SEQUENCE: 184
cgggctgggc cggcttaggt aggcgctcac ccctctcggg ttggaatcgc aaacgcagcc    60

<210> SEQ ID NO 185
<211> LENGTH: 12
<212> TYPE: DNA
<213> ORGANISM: EE+IGE

<400> SEQUENCE: 185
ggctgcgttt gc                                                       12

<210> SEQ ID NO 186
<211> LENGTH: 12
<212> TYPE: DNA
<213> ORGANISM: EE+IGE

```
<400> SEQUENCE: 186
gcaaacgcag cc                                                    12

<210> SEQ ID NO 187
<211> LENGTH: 32
<212> TYPE: DNA
<213> ORGANISM: EE+IGE

<400> SEQUENCE: 187
gatcaagctt gcgcacctac acctgccagg tc                              32

<210> SEQ ID NO 188
<211> LENGTH: 32
<212> TYPE: DNA
<213> ORGANISM: EE+IGE

<400> SEQUENCE: 188
gatcaccggt acacgcgggc cgctggtctt gg                              32

<210> SEQ ID NO 189
<211> LENGTH: 26
<212> TYPE: DNA
<213> ORGANISM: EE+IGE

<400> SEQUENCE: 189
ccggcccagc ccggtaccgg tagaaa                                     26

<210> SEQ ID NO 190
<211> LENGTH: 26
<212> TYPE: DNA
<213> ORGANISM: EE+IGE

<400> SEQUENCE: 190
tttctaccgg taccgggctg ggccgg                                     26

<210> SEQ ID NO 191
<211> LENGTH: 34
<212> TYPE: DNA
<213> ORGANISM: EE+IGE

<400> SEQUENCE: 191
tgattacgcc aagcttgttc gacctgttca tccg                            34

<210> SEQ ID NO 192
<211> LENGTH: 34
<212> TYPE: DNA
<213> ORGANISM: EE+IGE

<400> SEQUENCE: 192
cggatgaaca ggtcgaacaa gcttggcgta atca                            34

<210> SEQ ID NO 193
<211> LENGTH: 32
<212> TYPE: DNA
<213> ORGANISM: EE+IGE

<400> SEQUENCE: 193
gattacgcca agcttggtga accactccac ca                              32

<210> SEQ ID NO 194
<211> LENGTH: 32
<212> TYPE: DNA
```

```
<213> ORGANISM: EE+IGE

<400> SEQUENCE: 194
tggtggagtg gttcaccaag cttggcgtaa tc                                32

<210> SEQ ID NO 195
<211> LENGTH: 32
<212> TYPE: DNA
<213> ORGANISM: EE+IGE

<400> SEQUENCE: 195
gattacgcca agcttgaccc gagactggat cg                                32

<210> SEQ ID NO 196
<211> LENGTH: 32
<212> TYPE: DNA
<213> ORGANISM: EE+IGE

<400> SEQUENCE: 196
cgatccagtc tcgggtcaag cttggcgtaa tc                                32

<210> SEQ ID NO 197
<211> LENGTH: 138
<212> TYPE: DNA
<213> ORGANISM: EE+IGE

<400> SEQUENCE: 197
atgaccatga ttacgccaag cttggggtgc cgcgaatcc taatgcgttg caaacaggac    60
tccgactgcc tggctggctg cgtttgcggg cccaacggtt tctgcggagg aggaccaagc  120
ttgatgagta aaggagaa                                                138

<210> SEQ ID NO 198
<211> LENGTH: 104
<212> TYPE: DNA
<213> ORGANISM: EE+IGE

<400> SEQUENCE: 198
atgaccatga ttacgccaag cttggggtgc cgcgaatcc taatgcgttg caaacaggac    60
tccgactgcc tggctggctg cgtttgcggg cccaacggtt tctg                   104

<210> SEQ ID NO 199
<211> LENGTH: 30
<212> TYPE: DNA
<213> ORGANISM: EE+IGE

<400> SEQUENCE: 199
ccaagcttgg ggtgctgcaa acaggactcc                                   30

<210> SEQ ID NO 200
<211> LENGTH: 30
<212> TYPE: DNA
<213> ORGANISM: EE+IGE

<400> SEQUENCE: 200
ggagtcctgt ttgcagcacc ccaagcttgg                                   30

<210> SEQ ID NO 201
<211> LENGTH: 138
<212> TYPE: DNA
<213> ORGANISM: EE+IGE

<400> SEQUENCE: 201
```

```
atgaccatga ttacgccaag cttggggtgc ccgcgaatcc taatgcgttg caaacaggac    60
tccgactgcc tggctggctg cgtttgcggg cccaacggtt tctgcggagg aggaccaagc   120
ttgatgagta aaggagaa                                                 138

<210> SEQ ID NO 202
<211> LENGTH: 30
<212> TYPE: DNA
<213> ORGANISM: EE+IGE

<400> SEQUENCE: 202
atcctaatgc gttgctgcct ggctggctgc                                     30

<210> SEQ ID NO 203
<211> LENGTH: 30
<212> TYPE: DNA
<213> ORGANISM: EE+IGE

<400> SEQUENCE: 203
gcagccagcc aggcagcaac gcattaggat                                     30

<210> SEQ ID NO 204
<211> LENGTH: 104
<212> TYPE: DNA
<213> ORGANISM: EE+IGE

<400> SEQUENCE: 204
atgaccatga ttacgccaag cttggggtgc ccgcgaatcc taatgcgttg caaacaggac    60
tccgactgcc tggctggctg cgtttgcggg cccaacggtt tctg                    104

<210> SEQ ID NO 205
<211> LENGTH: 26
<212> TYPE: DNA
<213> ORGANISM: EE+IGE

<400> SEQUENCE: 205
ggactccgac tgctgcgttt gcgggc                                         26

<210> SEQ ID NO 206
<211> LENGTH: 26
<212> TYPE: DNA
<213> ORGANISM: EE+IGE

<400> SEQUENCE: 206
gcccgcaaac gcagcagtcg gagtcc                                         26

<210> SEQ ID NO 207
<211> LENGTH: 138
<212> TYPE: DNA
<213> ORGANISM: EE+IGE

<400> SEQUENCE: 207
atgaccatga ttacgccaag cttggggtgc ccgcgaatcc taatgcgttg caaacaggac    60
tccgactgcc tggctggctg cgtttgcggg cccaacggtt tctgcggagg aggaccaagc   120
ttgatgagta aaggagaa                                                 138

<210> SEQ ID NO 208
<211> LENGTH: 33
<212> TYPE: DNA
<213> ORGANISM: EE+IGE
```

```
<400> SEQUENCE: 208
ggctggctgc gtttgctgcg gaggaggacc aag                           33

<210> SEQ ID NO 209
<211> LENGTH: 33
<212> TYPE: DNA
<213> ORGANISM: EE+IGE

<400> SEQUENCE: 209
cttggtcctc ctccgcagca aacgcagcca gcc                           33

<210> SEQ ID NO 210
<211> LENGTH: 46
<212> TYPE: DNA
<213> ORGANISM: EE+IGE

<400> SEQUENCE: 210
caagcttggg gtgccaaaga acggtactc tttgcaaaca ggactc              46

<210> SEQ ID NO 211
<211> LENGTH: 46
<212> TYPE: DNA
<213> ORGANISM: EE+IGE

<400> SEQUENCE: 211
gagtcctgtt tgcaaagagt accgtttctt tggcacccca agcttg             46

<210> SEQ ID NO 212
<211> LENGTH: 138
<212> TYPE: DNA
<213> ORGANISM: EE+IGE

<400> SEQUENCE: 212
atgaccatga ttacgccaag cttggggtgc caaagaaacg gtactctttg caaacaggac    60
tccgactgcc tggctggctg cgtttgcggg cccaacggtt tctgcggagg aggaccaagc   120
ttgatgagta aggagaa                                                 138

<210> SEQ ID NO 213
<211> LENGTH: 46
<212> TYPE: DNA
<213> ORGANISM: EE+IGE

<400> SEQUENCE: 213
caagcttggg gtgcgttgat cttgctccat cttgcaaaca ggactc              46

<210> SEQ ID NO 214
<211> LENGTH: 46
<212> TYPE: DNA
<213> ORGANISM: EE+IGE

<400> SEQUENCE: 214
gagtcctgtt tgcaagatgg agcaagatca acgcacccca agcttg              46

<210> SEQ ID NO 215
<211> LENGTH: 138
<212> TYPE: DNA
<213> ORGANISM: EE+IGE

<400> SEQUENCE: 215
atgaccatga ttacgccaag cttggggtgc gttgatcttg ctccatcttg caaacaggac    60
tccgactgcc tggctggctg cgtttgcggg cccaacggtt tctgcggagg aggaccaagc   120
```

-continued ttgatgagta aaggagaa                                                        138

<210> SEQ ID NO 216
<211> LENGTH: 45
<212> TYPE: DNA
<213> ORGANISM: EE+IGE

<400> SEQUENCE: 216
cctaatgcgt tgccaaagaa acggtactct ttgcctggct ggctg             45

<210> SEQ ID NO 217
<211> LENGTH: 45
<212> TYPE: DNA
<213> ORGANISM: EE+IGE

<400> SEQUENCE: 217
cagccagcca ggcaaagagt accgtttctt tggcaacgca ttagg             45

<210> SEQ ID NO 218
<211> LENGTH: 141
<212> TYPE: DNA
<213> ORGANISM: EE+IGE

<400> SEQUENCE: 218
atgaccatga ttcgccaag cttggggtgc ccgcgaatcc taatgcgttg ccaaagaaac         60
ggtactcttt gcctggctgg ctgcgtttgc gggcccaacg gtttctgcgg aggaggacca      120
agcttgatga gtaaaggaga a                                                  141

<210> SEQ ID NO 219
<211> LENGTH: 46
<212> TYPE: DNA
<213> ORGANISM: EE+IGE

<400> SEQUENCE: 219
acctaatgcg ttgcgttgat cttgctccat cttgcctggc tggctg            46

<210> SEQ ID NO 220
<211> LENGTH: 45
<212> TYPE: DNA
<213> ORGANISM: EE+IGE

<400> SEQUENCE: 220
cagccagcca ggcaagatgg agcaagatca acgcaacgca ttagg             45

<210> SEQ ID NO 221
<211> LENGTH: 141
<212> TYPE: DNA
<213> ORGANISM: EE+IGE

<400> SEQUENCE: 221
atgaccatga ttcgccaag cttggggtgc ccgcgaatcc taatgcgttg cgttgatctt         60
gctccatctt gcctggctgg ctgcgtttgc gggcccaacg gtttctgcgg aggaggacca      120
agcttgatga gtaaaggaga a                                                  141

<210> SEQ ID NO 222
<211> LENGTH: 147
<212> TYPE: DNA
<213> ORGANISM: EE+IGE

<400> SEQUENCE: 222

```
atgaccatga ttacgccaag cttggggtgc ccgcgaatcc taatgcgttg caaacaggac    60
tccgactgcc aaagaaacgg tactctttgc gtttgcgggc ccaacggttt ctgcggagga   120
ggaccaagct tgatgagtaa aggagaa                                       147
```

<210> SEQ ID NO 223
<211> LENGTH: 44
<212> TYPE: DNA
<213> ORGANISM: EE+IGE

<400> SEQUENCE: 223

```
ggactccgac tgccaaagaa acggtactct ttgcgtttgc gggc                     44
```

<210> SEQ ID NO 224
<211> LENGTH: 44
<212> TYPE: DNA
<213> ORGANISM: EE+IGE

<400> SEQUENCE: 224

```
gcccgcaaac gcaaagagta ccgtttcttt ggcagtcgga gtcc                     44
```

<210> SEQ ID NO 225
<211> LENGTH: 147
<212> TYPE: DNA
<213> ORGANISM: EE+IGE

<400> SEQUENCE: 225

```
atgaccatga ttacgccaag cttggggtgc ccgcgaatcc taatgcgttg caaacaggac    60
tccgactgcg ttgatcttgc tccatcttgc gtttgcgggc ccaacggttt ctgcggagga   120
ggaccaagct tgatgagtaa aggagaa                                       147
```

<210> SEQ ID NO 226
<211> LENGTH: 44
<212> TYPE: DNA
<213> ORGANISM: EE+IGE

<400> SEQUENCE: 226

```
ggactccgac tgcgttgatc ttgctccatc ttgcgtttgc gggc                     44
```

<210> SEQ ID NO 227
<211> LENGTH: 44
<212> TYPE: DNA
<213> ORGANISM: EE+IGE

<400> SEQUENCE: 227

```
gcccgcaaac gcaagatgga gcaagatcaa cgcagtcgga gtcc                     44
```

<210> SEQ ID NO 228
<211> LENGTH: 141
<212> TYPE: DNA
<213> ORGANISM: EE+IGE

<400> SEQUENCE: 228

```
atgaccatga ttacgccaag cttggggtgc ccgcgaatcc taatgcgttg caaacaggac    60
tccgactgcc tggctggctg cgtttgccaa agaaacggta ctctttgcgg aggaggacca   120
agcttgatga gtaaaggaga a                                             141
```

<210> SEQ ID NO 229
<211> LENGTH: 46
<212> TYPE: DNA
<213> ORGANISM: EE+IGE

```
<400> SEQUENCE: 229
ctggctgcgt tgccaaaga aacggtactc tttgcggagg aggacc              46

<210> SEQ ID NO 230
<211> LENGTH: 46
<212> TYPE: DNA
<213> ORGANISM: EE+IGE

<400> SEQUENCE: 230
ggtcctcctc cgcaaagagt accgtttctt tggcaaacgc agccag              46

<210> SEQ ID NO 231
<211> LENGTH: 141
<212> TYPE: DNA
<213> ORGANISM: EE+IGE

<400> SEQUENCE: 231
atgaccatga ttacgccaag cttggggtgc ccgcgaatcc taatgcgttg caaacaggac     60
tccgactgcc tggctggctg cgtttgcgtt gatcttgctc catcttgcgg aggaggacca   120
agcttgatga gtaaaggaga a                                             141

<210> SEQ ID NO 232
<211> LENGTH: 46
<212> TYPE: DNA
<213> ORGANISM: EE+IGE

<400> SEQUENCE: 232
ctggctgcgt tgcgttgat cttgctccat cttgcggagg aggacc               46

<210> SEQ ID NO 233
<211> LENGTH: 46
<212> TYPE: DNA
<213> ORGANISM: EE+IGE

<400> SEQUENCE: 233
ggtcctcctc cgcaagatgg agcaagatca acgcaaacgc agccag              46

<210> SEQ ID NO 234
<211> LENGTH: 54
<212> TYPE: DNA
<213> ORGANISM: EE+IGE

<400> SEQUENCE: 234
ctaatgcgtt gcaaacagga ctccgactgc ctggctggct gcgtttgctg cgga         54

<210> SEQ ID NO 235
<211> LENGTH: 33
<212> TYPE: DNA
<213> ORGANISM: EE+IGE

<400> SEQUENCE: 235
gatcgcggcc gcctaatgcg ttgcaaacag gac                            33

<210> SEQ ID NO 236
<211> LENGTH: 32
<212> TYPE: DNA
<213> ORGANISM: EE+IGE

<400> SEQUENCE: 236
gatcgaattc tccgcagcaa acgcagccag cc                             32
```

<210> SEQ ID NO 237
<211> LENGTH: 38
<212> TYPE: DNA
<213> ORGANISM: EE+IGE

<400> SEQUENCE: 237
gatcgaattc tccgcattcg cattcaacgc agccagcc                           38

<210> SEQ ID NO 238
<211> LENGTH: 114
<212> TYPE: DNA
<213> ORGANISM: EE+IGE

<400> SEQUENCE: 238
gggtgcccgc gaatcctaat gcgttgcaaa caggactccg actgcctggc tggctgcgtt   60
tgcgggccca acggtttctg cggagggtgc ccgcgaatcc cacgggcgc ttag         114

<210> SEQ ID NO 239
<211> LENGTH: 69
<212> TYPE: DNA
<213> ORGANISM: EE+IGE

<400> SEQUENCE: 239
ctaatgcgtt gcaaacagga ctccgactgc ctggctggct gcgtttgcgg gcccaacggt   60
ttctgcgga                                                          69

<210> SEQ ID NO 240
<211> LENGTH: 69
<212> TYPE: DNA
<213> ORGANISM: EE+IGE

<400> SEQUENCE: 240
gattacgcaa cgtttgtcct gaggctgacg gaccgaccga cgcaaacgcc cgggttgcca   60
aagacgcct                                                          69

<210> SEQ ID NO 241
<211> LENGTH: 33
<212> TYPE: DNA
<213> ORGANISM: EE+IGE

<400> SEQUENCE: 241
gatcgcggcc gcctaatgcg ttgcaaacag gac                                33

<210> SEQ ID NO 242
<211> LENGTH: 31
<212> TYPE: DNA
<213> ORGANISM: EE+IGE

<400> SEQUENCE: 242
gatcgaattc tccgcagaaa ccgttgggcc c                                  31

<210> SEQ ID NO 243
<211> LENGTH: 23
<212> TYPE: PRT
<213> ORGANISM: EE+IGE

<400> SEQUENCE: 243

Leu Met Arg Cys Lys Gln Asp Ser Asp Cys Leu Ala Gly Cys Val Cys
1               5                   10                  15

Gly Pro Asn Gly Phe Cys Gly
            20

<210> SEQ ID NO 244
<211> LENGTH: 150
<212> TYPE: DNA
<213> ORGANISM: EE+IGE

<400> SEQUENCE: 244

```
ctaatgcgtt gcaaacagga ctccgactgc ctggctggct gcgtttgcac ccgcgattgg      60
attgaaggcg aaacctatca gtgccgcgtg acccatccgc atctgccgcg cgcgctgatg     120
cgcagcacca ccaaaaccag cggcccgcgc                                       150
```

<210> SEQ ID NO 245
<211> LENGTH: 129
<212> TYPE: DNA
<213> ORGANISM: EE+IGE

<400> SEQUENCE: 245

```
ctaatgcgtt gcaaacagga ctccgactgc ctggctggct gcgtttgcca gtgccgcgtg      60
acccatccgc atctgccgcg cgcgctgatg cgcagcacca ccaaaaccag cggcccgcgc     120
ttctgcgga                                                              129
```

<210> SEQ ID NO 246
<211> LENGTH: 124
<212> TYPE: DNA
<213> ORGANISM: EE+IGE

<400> SEQUENCE: 246

```
ctaatgcgtt gcaaacagga ctccgactgc ctggctggct gcgtttgccc gcgtgaccca      60
tccgcatctg ccgcgcgcgc tgatgcgcag caccaccaaa accagcggcc cgcgcttctg     120
cgga                                                                   124
```

<210> SEQ ID NO 247
<211> LENGTH: 52
<212> TYPE: PRT
<213> ORGANISM: EE+IGE

<400> SEQUENCE: 247

Leu Met Arg Cys Lys Gln Asp Ser Asp Cys Leu Ala Gly Ser Val Cys
1               5                   10                  15

Thr Arg Asp Trp Ile Glu Gly Glu Thr Tyr Gln Cys Arg Val Thr His
            20                  25                  30

Pro His Leu Pro Arg Ala Leu Met Arg Ser Thr Thr Lys Thr Ser Gly
        35                  40                  45

Pro Arg Phe Cys
    50

<210> SEQ ID NO 248
<211> LENGTH: 42
<212> TYPE: PRT
<213> ORGANISM: EE+IGE

<400> SEQUENCE: 248

Leu Met Arg Cys Lys Gln Asp Ser Asp Cys Leu Ala Gly Ser Val Cys
1               5                   10                  15

Gln Cys Arg Val Thr His Pro His Leu Pro Arg Ala Leu Met Arg Ser
            20                  25                  30

Thr Thr Lys Thr Ser Gly Pro Arg Phe Cys
        35                  40

<210> SEQ ID NO 249
<211> LENGTH: 35
<212> TYPE: PRT
<213> ORGANISM: EE+IGE

<400> SEQUENCE: 249

Leu Met Arg Cys Lys Gln Asp Ser Asp Cys Leu Ala Gly Ser Val Cys
1               5                   10                  15

His Pro His Leu Pro Arg Ala Leu Met Arg Ser Thr Thr Lys Thr Ser
            20                  25                  30

Gly Pro Arg
        35

<210> SEQ ID NO 250
<211> LENGTH: 144
<212> TYPE: DNA
<213> ORGANISM: EE+IGE

<400> SEQUENCE: 250
ctaatgcgtt gcaaacagga ctccgactgc ctggctggct gcgtttgcga aggcgaaacc      60
tatcagtgcc gcgtgaccca tccgcatctg ccgcgcgcgc tgatgcgcag caccaccaaa     120
accagcggcc gcgcttctg cgga                                            144

<210> SEQ ID NO 251
<211> LENGTH: 47
<212> TYPE: PRT
<213> ORGANISM: EE+IGE

<400> SEQUENCE: 251

Leu Met Arg Cys Lys Gln Asp Ser Asp Cys Leu Ala Gly Ser Val Cys
1               5                   10                  15

Glu Gly Glu Thr Tyr Gln Cys Arg Val Thr His Pro His Leu Pro Arg
            20                  25                  30

Ala Leu Met Arg Ser Thr Thr Lys Thr Ser Gly Pro Arg Phe Cys
        35                  40                  45

<210> SEQ ID NO 252
<211> LENGTH: 26
<212> TYPE: PRT
<213> ORGANISM: H. sapiens

<400> SEQUENCE: 252

Gly His Thr Phe Glu Asp Ser Thr Lys Lys Cys Ala Asp Ser Asn Pro
1               5                   10                  15

Arg Gly Val Ser Ala Tyr Leu Ser Arg Pro
            20                  25

<210> SEQ ID NO 253
<211> LENGTH: 21
<212> TYPE: PRT
<213> ORGANISM: H. sapiens

<400> SEQUENCE: 253

Asp Ser Thr Lys Lys Cys Ala Asp Ser Asn Pro Arg Gly Val Ser Ala
1               5                   10                  15

Tyr Leu Ser Arg Pro
            20

<210> SEQ ID NO 254

```
<211> LENGTH: 16
<212> TYPE: PRT
<213> ORGANISM: H. sapiens

<400> SEQUENCE: 254

Cys Ala Asp Ser Asn Pro Arg Gly Val Ser Ala Tyr Leu Ser Arg Pro
1               5                   10                  15

<210> SEQ ID NO 255
<211> LENGTH: 30
<212> TYPE: PRT
<213> ORGANISM: H. sapiens

<400> SEQUENCE: 255

Arg Thr Tyr Thr Cys Gln Val Thr Tyr Gln Gly His Thr Phe Glu Asp
1               5                   10                  15

Ser Thr Lys Lys Cys Ala Asp Ser Asn Pro Arg Gly Val Ser
            20                  25                  30

<210> SEQ ID NO 256
<211> LENGTH: 31
<212> TYPE: PRT
<213> ORGANISM: H. sapiens

<400> SEQUENCE: 256

Gln Val Thr Tyr Gln Gly His Thr Phe Glu Asp Ser Thr Lys Lys Cys
1               5                   10                  15

Ala Asp Ser Asn Pro Arg Gly Val Ser Ala Tyr Leu Ser Arg Pro
            20                  25                  30

<210> SEQ ID NO 257
<211> LENGTH: 15
<212> TYPE: PRT
<213> ORGANISM: H. sapiens

<400> SEQUENCE: 257

Ala Asp Ser Asn Pro Arg Gly Val Ser Ala Tyr Leu Ser Arg Pro
1               5                   10                  15

<210> SEQ ID NO 258
<211> LENGTH: 29
<212> TYPE: PRT
<213> ORGANISM: H. sapiens

<400> SEQUENCE: 258

Thr Tyr Gln Gly His Thr Phe Glu Asp Ser Thr Lys Lys Cys Ala Asp
1               5                   10                  15

Ser Asn Pro Arg Gly Val Ser Ala Tyr Leu Ser Arg Pro
            20                  25

<210> SEQ ID NO 259
<211> LENGTH: 16
<212> TYPE: PRT
<213> ORGANISM: H. sapiens

<400> SEQUENCE: 259

Cys Ala Asp Ser Asn Pro Arg Gly Val Ser Ala Tyr Leu Ser Arg Pro
1               5                   10                  15

<210> SEQ ID NO 260
<211> LENGTH: 22
<212> TYPE: PRT
<213> ORGANISM: H. sapiens
```

<400> SEQUENCE: 260

Glu Asp Ser Thr Lys Lys Cys Ala Asp Ser Asn Pro Arg Gly Val Ser
1               5                   10                  15

Ala Tyr Leu Ser Arg Pro
            20

<210> SEQ ID NO 261
<211> LENGTH: 31
<212> TYPE: PRT
<213> ORGANISM: H. sapiens

<400> SEQUENCE: 261

Gln Val Thr Tyr Gln Gly His Thr Phe Glu Asp Ser Thr Lys Lys Cys
1               5                   10                  15

Ala Asp Ser Asn Pro Arg Gly Val Ser Ala Tyr Leu Ser Arg Pro
            20                  25                  30

<210> SEQ ID NO 262
<211> LENGTH: 27
<212> TYPE: PRT
<213> ORGANISM: H. sapiens

<400> SEQUENCE: 262

Thr Arg Asp Trp Ile Glu Gly Glu Thr Tyr Gln Cys Arg Val Thr His
1               5                   10                  15

Pro His Leu Pro Arg Ala Leu Met Arg Ser Thr
            20                  25

<210> SEQ ID NO 263
<211> LENGTH: 12
<212> TYPE: PRT
<213> ORGANISM: H. sapiens

<400> SEQUENCE: 263

His Pro His Leu Pro Arg Ala Leu Met Arg Ser Thr
1               5                   10

<210> SEQ ID NO 264
<211> LENGTH: 29
<212> TYPE: PRT
<213> ORGANISM: H. sapiens

<400> SEQUENCE: 264

Thr Arg Asp Trp Ile Glu Gly Glu Thr Tyr Gln Cys Arg Val Thr His
1               5                   10                  15

Pro His Leu Pro Arg Ala Leu Met Arg Ser Thr Thr Lys
            20                  25

<210> SEQ ID NO 265
<211> LENGTH: 24
<212> TYPE: PRT
<213> ORGANISM: H. sapiens

<400> SEQUENCE: 265

Thr Arg Asp Trp Ile Glu Gly Glu Thr Tyr Gln Cys Arg Val Thr His
1               5                   10                  15

Pro His Leu Pro Arg Ala Leu Met
            20

<210> SEQ ID NO 266
<211> LENGTH: 48
<212> TYPE: PRT

```
<213> ORGANISM: H. sapiens

<400> SEQUENCE: 266

Leu Met Arg Cys Lys Gln Asp Ser Asp Cys Leu Ala Gly Ser Val Cys
1               5                   10                  15

Thr Arg Asp Trp Ile Glu Gly Glu Thr Tyr Gln Cys Arg Val Thr His
            20                  25                  30

Pro Ala Leu Met Arg Ser Thr Thr Lys Thr Ser Gly Pro Arg Phe Cys
        35                  40                  45

<210> SEQ ID NO 267
<211> LENGTH: 41
<212> TYPE: PRT
<213> ORGANISM: H. sapiens

<400> SEQUENCE: 267

Leu Met Arg Cys Lys Gln Asp Ser Asp Cys Leu Ala Gly Ser Val Cys
1               5                   10                  15

Phe Glu Asp Ser Thr Lys Lys Cys Ala Asp Ser Asn Pro Arg Gly Val
            20                  25                  30

Ser Ala Tyr Leu Ser Arg Pro Phe Cys
        35                  40

<210> SEQ ID NO 268
<211> LENGTH: 48
<212> TYPE: PRT
<213> ORGANISM: H. sapiens

<400> SEQUENCE: 268

Leu Met Arg Cys Lys Gln Asp Ser Asp Cys Leu Ala Gly Ser Val Cys
1               5                   10                  15

Val Thr Tyr Gln Gly His Thr Phe Glu Asp Ser Thr Lys Lys Cys Ala
            20                  25                  30

Asp Ser Asn Pro Arg Gly Val Ser Ala Tyr Leu Ser Arg Pro Phe Cys
        35                  40                  45

<210> SEQ ID NO 269
<211> LENGTH: 18
<212> TYPE: PRT
<213> ORGANISM: H. sapiens

<400> SEQUENCE: 269

Lys Lys Cys Ala Asp Ser Asn Pro Arg Gly Val Ser Ala Tyr Leu Ser
1               5                   10                  15

Arg Pro

<210> SEQ ID NO 270
<211> LENGTH: 25
<212> TYPE: PRT
<213> ORGANISM: H. sapiens

<400> SEQUENCE: 270

Glu Gly Glu Thr Tyr Gln Cys Arg Val Thr His Pro Ala Leu Met Arg
1               5                   10                  15

Ser Thr Thr Lys Thr Ser Gly Pro Arg
            20                  25

<210> SEQ ID NO 271
<211> LENGTH: 22
<212> TYPE: PRT
<213> ORGANISM: H. sapiens
```

<400> SEQUENCE: 271

Arg Val Thr His Pro His Leu Pro Arg Ala Leu Met Arg Ser Thr Thr
1               5                   10                  15

Lys Thr Ser Gly Pro Arg
            20

<210> SEQ ID NO 272
<211> LENGTH: 29
<212> TYPE: PRT
<213> ORGANISM: H. sapiens

<400> SEQUENCE: 272

Thr Arg Asp Trp Ile Glu Gly Glu Thr Tyr Gln Cys Arg Val Thr His
1               5                   10                  15

Pro His Leu Pro Arg Ala Leu Met Arg Ser Thr Thr Lys
            20                  25

<210> SEQ ID NO 273
<211> LENGTH: 24
<212> TYPE: PRT
<213> ORGANISM: H. sapiens

<400> SEQUENCE: 273

Thr Arg Asp Trp Ile Glu Gly Glu Thr Tyr Gln Cys Arg Val Thr His
1               5                   10                  15

Pro His Leu Pro Arg Ala Leu Met
            20

<210> SEQ ID NO 274
<211> LENGTH: 31
<212> TYPE: PRT
<213> ORGANISM: H. sapiens

<400> SEQUENCE: 274

Thr Arg Asp Trp Ile Glu Gly Glu Thr Tyr Gln Cys Arg Val Thr His
1               5                   10                  15

Pro His Leu Pro Arg Ala Leu Met Arg Ser Thr Thr Lys Thr Ser
            20                  25                  30

<210> SEQ ID NO 275
<211> LENGTH: 16
<212> TYPE: PRT
<213> ORGANISM: H. sapiens

<400> SEQUENCE: 275

Leu Pro Arg Ala Leu Met Arg Ser Thr Thr Lys Thr Ser Gly Pro Arg
1               5                   10                  15

<210> SEQ ID NO 276
<211> LENGTH: 12
<212> TYPE: PRT
<213> ORGANISM: H. sapiens

<400> SEQUENCE: 276

His Pro His Leu Pro Arg Ala Leu Met Arg Ser Thr
1               5                   10

<210> SEQ ID NO 277
<211> LENGTH: 12
<212> TYPE: DNA
<213> ORGANISM: EE+IGE

```
<400> SEQUENCE: 277
ggctgcgttt gc                                                             12

<210> SEQ ID NO 278
<211> LENGTH: 83
<212> TYPE: DNA
<213> ORGANISM: EE+IGE

<400> SEQUENCE: 278
gcggccgcct aatgcgttgc aaacaggact ccgactgcct ggctggctgc gtttgcgggc         60
ccaacggttt ctgcggagaa ttc                                                 83

<210> SEQ ID NO 279
<211> LENGTH: 5
<212> TYPE: PRT
<213> ORGANISM: H. sapiens

<400> SEQUENCE: 279

Pro Arg Gly Val Ser
1               5

<210> SEQ ID NO 280
<211> LENGTH: 5
<212> TYPE: PRT
<213> ORGANISM: H. sapiens

<400> SEQUENCE: 280

Asn Pro Arg Gly Val
1               5
```

DISPLAYING NATIVE HUMAN IGE NEUTRALIZING FCEPSILONRIA-CONTACTING IGE B-CELL EPITOPES BY CONSTRAINING SUPER BETA(B)-STRANDS AND CYSTINE KNOTS ON THERMOSTABLE PROTEIN SCAFFOLD

This application claims priority in U.S. Provisional Application No. 61/590,778 filed on Jan. 25, 2012, which is incorporated herein by reference in its entirety.

FIELD OF THE INVENTION

This invention pertains to novel methods of scaffolding IgE peptides into native conformation as antigenic vaccine epitopes.

BACKGROUND OF INVENTION

Multifactorial pathogenic process of allergic asthma has posed a challenge in treating this disease. IgE-mediated immediate hypersensitivity exercises two subsystems in play: (i) Upstream CD4-T-cells/IgE+ B-cells subsystem: Allergen-specific Th2/Th17 CD4 T-cells contribute to the cytokine-mediated late phase reactions. In contrast, follicular CD4 (Tfh) T-cells provide essential help to stimulate IgE+ B-cells in the germinal center (GC) and peri-GC memory B-cells (Crotty, 2011, Ann. Rev. Immunol., 29: 621). (ii) Downstream IgE network subsystem: IgE produced by the upstream Tfh/IgE B-cells initiates and amplifies a complex network of the inflammatory cell circuit of extraordinary diversity, involving a web of high affinity IgE receptor (FceRI)-bearing mast cells, basophils, eosinophils, dendritic cells and Langerhans cells, and recently neutrophils. Mezzanine intercommunication layer: Histamine released by mast cells skews dendritic cells (DCs) for Th2 preference (Lambrecht, 2009, Immunity, 31:412). FceRI on mast cells mediated IgE-dependent antigen presentation, and further augmented Th2 development (Gong, 2010, BMC Immunol, 2010, 11:34).

IgE-mediated inflammation can cause the acute phase of immediate hypersensitivity, and the late phase reaction via a plethora of IgE-produced mediators; and the IgE-FceRI cellular network can in turn enhance Th2, and the Th2-mediated late and chronic phases of allergic asthma. To add further importance to IgE is the expression of FceRI on airway smooth muscle cells for the release of TNF-a during intractable asthma. Bronchial epithelial cells also exhibit FceRI, implicated in released IL-33 and TSLP that amplify Th2-mediated inflammation (Galli and Tsai, 2012, Nat. Med., 18:693).

Besides the IgE/FceRI network, low affinity IgE receptors (FceRII, CD23) are expressed on nearly all B-cells, which mediate IgE-dependent antigen presentation for Th2 (Schmaltz, 1996, Immunol. Invest., 25: 481). FceRII on epithelial cells plays a key role in retrograde transport of IgE immune complexes in the BAL fluid, which can therefore play a role in augmenting allergen/IgE complexes-induced inflammation on intraepithelial mast cells and airway dendritic cells. The expression of FceRI on IL17AR+ neutrophils strongly suggests a new synergy of IgE and Th17-mediated inflammation in allergic asthma (Galli and Tsai, 2012, Nat. Med. 18:693; Lambrecht et al., 2009, at. Med., 31: 412).

Thus, IgE is of paramount importance in the etiology of allergic asthma by affecting IgE-mediated inflammation, a plethora of cytokines by multiple cell types, and the profound impact on Th2 (Schmaltz, 1996, Immunol. Invest., 25: 481; Gong et al., 2010, BMC Immunol., 11:34). Thus a drug candidate such as IgE B-cell vaccine targeting IgE attenuates inflammation at the multiple levels, in particular ramification of the IgE-FceRI network. Blunting IgE and IgE receptors by neutralizing anti-IgE remains the central question in treating clinical allergic asthma.

To alleviate or cure the IgE-mediated allergic diseases, it is imperative to remove circulating and mucosal IgE. In this regard, the present treatment modality focuses on the removal of circulating IgE via passive administered monoclonal antibody, Xolair. Anti-IgE, Xolair that neutralizes the receptor-binding FG loop of IgE molecules alleviates IgE-mediated allergic asthma (Chang, 2000, Nat. Biotech., 18:157). In contrast to the passive monoclonal antibody-based passive vaccine, active IgE vaccines were proposed as another treatment modality to invoke actively produced anti-IgE that neutralizes host's IgE. One approach resides in random chemical coupling of synthetic IgE peptides to the immunogenic protein carriers as active vaccines (Brown et al., 2009, U.S. patent application Ser. No. 12/634,336).

Another embodiment of invention resides in engineering neutralizing IgE B-cell epitopes within thermostable, immunogenic protein scaffold in a single step internally (Chen, 2008, U.S. patent application Ser. No. 12/011,303; Chen, 2008, J. Immunol. Meth., 333: 10). The present embodiment of the invention represents constraining native IgE B-cell epitopes in two internal steps: into super b-strands, and further into the cystine knots; and then integrated in one external step onto the protein scaffold, of which the thermostability of the immunogenic protein scaffold is not compromised by foreign loop insertion.

Conception of a monospecific B-cell epitope and its conjugation as synthetic peptide unto an immunogenic protein was pioneered by Atassi, Lerner and Brown in the late 80's (Rowlands et al., 1983, Nature, 306: 694; Atassi, 1978, Immunochem., 15: 909). Most antigenic structure are presented as a loop constrained by the secondary alpha helix and beta sheet structure, and properly folded in the three dimensional array determined by favorable energetics.

Through extensive studies of numerous potential B-cell candidate epitopes, a B-cell loop antigenic epitope, taken out from the native constrained secondary and tertiary protein folding, is distorted in conformation. Such synthetic or recombinant peptides randomly conjugated to or integrated to a protein carrier backbone exhibited thermodynamically unpredictable, multiple distorted, random conformations (Rowlands, et al., 1983, Nature, 306:694). Synthetic or recombinant linear IgE B-cell epitopes without proper constraint remain in a state of complex random array without definable structural integrity. Constraining scaffold in supporting the antigenic loop is required for enabling functional native conformation with structural integrity.

In contrast, conception of constrained IgE B-cell epitopes prompts the step to constrain the IgE B-cell epitope directly in the thermostable protein scaffold, whereby functional native conformation of the constrained neutralizing IgE B-cell epitopes can be enabled by the constraint. The embodiment of this invention further improves the constraining platform in placing B-cell epitopes into the super constraining beta (b)-strands, and further strengthened by the thermostable cystine knots, and finally integrated onto another thermostable protein scaffold, engineered in an optimal oxidative folding chemical milieu. Hence the embodiment of the three improvements in this invention enables the native expression and structural integrity of the B-cell epitopes.

The embodiment of this invention with active, conformationally constrained IgE B-cell epitope vaccine improves over the passive neutralizing anti-IgE monoclonal antibody (Chang, 1995, U.S. Pat. No. 5,428,133): (i) Sustained circulating IgE-Xolair complexes in treated patients cause long-term IgE suppression. The regimen requires 36 to 54 week-long treatment in order to neutralize 95% circulating IgE. However, due to the small size of immune complexes, circulating IgE/IgG1 Xolair complexes assume a half-life of 21 days of IgG1 (IgE lasts only one day); consequently, total circulating IgE in the complexes are persistently elevated ~100 fold as a result of treatment (Chang, 2010, Nat. Biotech., 18:157).

Active IgE B-cell vaccines embodied by this invention improve the safety margin by producing active polyclonal anti-IgE in the vaccinated recipients with appropriate length of protection based on the vaccination/booster regimen. The duration is controlled by reactivation of memory CD4 helper T-cells to the protein scaffold. Due to the polyclonal antibodies, the clearance of circulating and mucosal IgE and IgG complexes will be efficient via the liver sinusoids and Kupffer cells. Furthermore, as a murine human chimera antibodies, Xolair causes anaphylaxis in individuals (3.14/1000 patients vs 5.4 events/million shots), the constrained IgE B-cell active vaccine induces endogenous autologous anti-IgE indigenous to the host.

(ii) Xolair is inefficient in targeting the mission-critical pathogenic IgE in the lung. The passively delivered Xolair via the subcut route, sieved through afferent lymphatics into thoracic duct lymph into the general blood circulation, without permeating into the critical sites of the lung, central for allergic asthma. Allergen-specific IgE, secreted by IgE plasma cells present in induced peribronchus-associated lymphoid tissues (iBALT), into the surrounding lamina propria under the bronchial epithelial and endothelial cells, remains inaccessible to circulating anti-IgE monoclonal antibodies, whose delivery depends solely on inflammation-mediated changes in vascular permeability (Lambrecht, 2009, Nat. Med., 31: 412).

A further embodiment of this invention is that IgE B-cell vaccines delivered via mucosa route of immunization elicit anti-IgE in iBALT that neutralizes pathogenic IgE in situ in the iBALT. The FG super b-strands constrained IgE B-cell epitopes with or without Min-23 cystine knot constraint, integrated onto the immunogenic protein scaffold can be employed as IgE B-cell vaccines. B-cells recognizing native, constrained FceRIa receptor-binding IgE-B-cell epitopes are activated by CD4 helper T-cells reactive with CD4 helper epitopes on the immunogenic protein scaffold. Anti-IgE antibodies of the IgA and IgG classes can be released directly in mucosal secretion in addition to circulation via a preferred mucosal route of immunization with FDA-approved adjuvants, Toll like receptor (TLR)-7 agonist imiquimod, alum, lipid A-based adjuvant or TLR-9 adjuvant presently being evaluated.

The designed constrained IgE B-cell vaccines elicit polyclonal neutralizing anti-IgE of the IgG and IgA classes that inhibits IgE-mediated mast cell degranulation, and prevents airway inflammation and airway hyper-reactivity (Ahr) (Zuberi et al, 2000, J. I., 164: 2667). Thus engineering constrained IgE B-cell epitopes in the FG super b-strands and cystine knots, integrated onto the immunogenic protein scaffold yields can lead to new anti-IgE pan-allergy vaccines that can benefit asthmatics of different disease spectra through mucosal IgE targeting and neutralization.

SUMMARY OF THIS INVENTION

The embodiment of this invention is to identify super constraining b-stranded secondary structure, and employing the identified super b-strands to accommodate and support the newly inserted a monospecific B-cell epitope of the loop structure, which constitutes the active site for receptor recognition or protein-protein interactions in the inflammatory pathways or bacterial or viral infections. The robust or super energy-favorable b-stranded secondary structure can next be integrated into a thermostable cystine knotted structure onto a thermostable scaffold protein. This presents a novel invented method of grafting and preserving 3-dimensional B-cell epitopes for eliciting neutralizing antibodies against microbial antigens and inflammatory molecules.

BRIEF DESCRIPTION OF THE FIGURES

FIG. 6 depicts detection of swapped native human C2-3, BC, and DE core loop sequences in super b-strands of truncated FG microdomain on GFP. FG-5 and FG-10 truncated FG-GFP were prepared as above. SDM was conducted with primers with foreign IgE B-cell epitopes: core loop sequences from C2-3, BC and DE, while devoid of the native FG loop sequences were performed by primer extension. The resulting mutated clones with the replaced loop sequences were ascertained by DNA sequencing. Panel A: various loop-substituted recombinant products with C-terminal His-tag were affinity purified by IMAC column. Immune reactivity with 100 ng native inserted sequences was detected under native condition as described in legend of FIG. 5 by neutralizing polyclonal goat anti-IgE antibodies. The neutralizing antibodies were tested blocking human IgE binding to the recombinantly produced FceRI, D2/D1 subunit. Panel B: conventional western blot was also performed with the above products run under denaturing SDS-PAGE with heated sample treatment buffer containing 2-ME and SDS. 1) FG full length (SEQ ID: 10); 2) FG N-5 (SEQ ID: 12); 3) FG N-10 (SEQ ID: 14); 4) FG N-5 delete HLPR (SEQ ID: 270); 5) N-5 FG+ RNGT (SEQ ID: 106); 6) FG N-10 +NPRGVS (SEQ ID: 57); 7) FG N-10 +DLAP (SEQ ID: 84); 8) IgE (BED) (SEQ ID: 1).

FIG. 7 A/B/C depict comparison native expression of swapped C2-3, BC, DE loop B-cell epitopes in super b-strands of FG-N5 (SEQ ID: 11) versus FG-N10 FG (SEQ ID: 13) microdomain onto GFP scaffold. A complete set of three IgE B-cell loop epitopes, C2-3, BC, and DE core loop sequences were cloned into the FG-5 FG core loop swapped GFP, and FG-10 FG core loop swapped GFP. In the native detecting conditions, FG native loop and loop swapped-GFP recombinant products exist as tetramers around 120 KDa, characteristic of GFP in native tetramers. The effect of deletion of core loop sequences on the integrity of GFP protein scaffold is evaluated (lane 11 and 12 of Panel C). 1) IgE (SEQ ID: 1); 2) GFP (SEQ ID: 52); 3) DE full length (SEQ ID: 8); 4) BC full length (SEQ ID: 6); 5) N-10 FG+DLAP (SEQ ID: 84); 6) N-5 FG+ DLAP (SEQ ID: 100); 7) N-10 FG+ NPRGVS (SEQ ID: 57); 8) FG N-5+ NPRGVS (SEQ ID: 73); 9) N-10 FG+ RNGT (SEQ ID: 104); 10) N-5 FG+ RNGT (SEQ ID: 106); 11) N-10 FGF minus HLPR (SEQ ID: 18); 12) N-5 FG minus HLPR (SEQ ID: 21); 13) N-10 FG (SEQ ID: 14); 14) N-5 FG (SEQ ID: 12).

FIG. 8. depicts rodent sequences for C2-3, BC, DE loop swapped surrogate vaccines. A corresponding set of surrogate rodent vaccine were prepared by replacing the homologous rodent sequences with the native human FG core loop sequence: C2-3L (EPRGVI) (SEQ ID: 129), BC (DLAE) (SEQ ID: 130), DE (NNATL) (SEQ ID: 131), and FG (DFPK) (SEQ ID: 132) loops were swapped into the human super b-strands that flank the native human FG loop with the native human HLPR sequence deleted. The recombinant proteins are detected by rabbit anti-26.82 rodent IgE prepared in the lab. 1) N-10 FG+rodent C2-3 core (SEQ ID: 137); 2) N-10 FG+rodent BC core (SEQ ID: 138); 3) N-10 FG+rodent DE core (SEQ ID: 139); 4) N-10 FG+rodent FG core (SEQ ID: 140).

FIG. 9 depicts anti-IgE elicited by FG-N-10-GFP blocking human IgE binding to recombinant human FceRIa. Panel A showed a standard IgE binding curve to recombinant receptors with OD signal ~1.2 at 50 ng/ml (the red open bar). Panel B showed diluted sera from the FG-N-10-GFP immunized mice attenuated the human IgE binding to D2/D1 FceRIa.

FIG. 14 depicts expression of loop B-cell epitopes of BC and DE swapped into loop 1, 2, 3, 5 of wild type EETI-II. Two overlapping forward and reverse primers, each partially encompassing wild type EETI-II were synthesized, and annealed, and filled in. PCR reaction was next conducted with short forward and reverse primer (with the HindIII site), and the amplified full length of EETI-II was digested with HindIII and annealed with HindIII digested GFP$_{UV}$ vector, and bacterial clone selected by DNA sequencing. BC and DE loop B-cell epitope insertion mutants are prepared by addition primer extension with forward and reverse primers encompassing the overlapping sequence of EETI-II and the added BC, DE loop sequences via SDM. 1) EETI-II (min 28) (SEQ ID: 47, SEQ ID: 48); 2) EETI-II Loop 1 deletion clone 1 replaced with VDLAPS (SEQ ID: 151, SEQ ID: 152); 3) EETI-II Loop 1 deletion clone 2 replaced with QRNGTL (SEQ ID: 149, SEQ ID: 150); 4) EETI-II Loop 2 deletion clone 3 replaced with VDLAPS (SEQ ID: 155, SEQ ID: 156); 5) EETI-II Loop 2 deletion clone 4 replaced with QRNGTL (SEQ ID: 153, SEQ ID: 154); 6) EETI-II Loop 3 deletion clone 5 replaced with VDLAPS (SEQ ID:159, SEQ ID: 160); 7) EETI-II Loop 3 deletion clone 6 replaced with QRNGTL (SEQ ID: 157, SEQ ID: 158); 8) EETI-II Loop 5 deletion clone 7 replaced with VDLAPS (SEQ ID: 163, SEQ ID: 164); 9) EETI-II Loop 5 deletion clone 8 replaced with QRNGTL (SEQ ID: 161, SEQ ID: 162).

(SEQ ID: 260); 4) pMal M23 (empty loop 5)+ C31 C2-3 (SEQ ID: 261); 5) pMal M23 (empty loop 5)+FG (SEQ ID: 10); 6) pMal M23 (empty loop 5)+ N-10 FG (SEQ ID: 14); 7) pMal (SEQ ID: 50) Min23 empty loop5 (SEQ ID: 42); 8) IgE (BED) (SEQ ID: 1).

FIG. 19 depicts enhanced reactivities of native truncated N-10 FG-Min-18-pMal (Min-23 series) with neutralizing anti-human IgE. Truncated FG-N-10-Min-18-pMal was purified form periplasmic space via maltose column. 200 ng of the recombinant constructs of various deletions from the N- or C-terminus, including HLPR deleted constructed were detected under the native non-denaturing conditions with neutralizing anti-IgE. The intensity of the expression unpurified, in the bacterial extract, was compared to high dose of human myeloma IgE (BED). Notably, full length FG microdomain exhibited weak expression of native FG loop in the bacterial extract, while the intensity of native loop HLPR (SEQ ID: 23) of one single B-cell epitope expressed in FG N-10 construct in bacterial extract in the oxidative periplasmic space, exceeded that of myeloma human IgE with all four neutralizing B-cell epitopes. 1) pMal (SEQ ID: 50) min23 (empty loop 5 without glyglygly linker, i.e, min18) (SEQ ID: 42) (SEQ ID: 44)+ FG (SEQ ID: 10); 2) min23 (empty loop 5)+ N-5 FG (SEQ ID: 251); 3) min 23 (empty loop 5)+ N-15 FG (SEQ ID: 249); 4) min 23 (empty loop 5)+ N-18 FG (SEQ ID: 275); 5) min 23 (empty loop 5)+ C-3 FG (SEQ ID: 274); 6) min23 (empty loop 5)+ C-5 FG (SEQ ID: 272); 7) min 23 (empty loop 5) + C-10 FG (SEQ ID: 273); 8) min23 empty loop 5 (without glyglygly linker) (SEQ ID: 42); 8) IgE (BED) (SEQ ID: 1).

Figure 20:
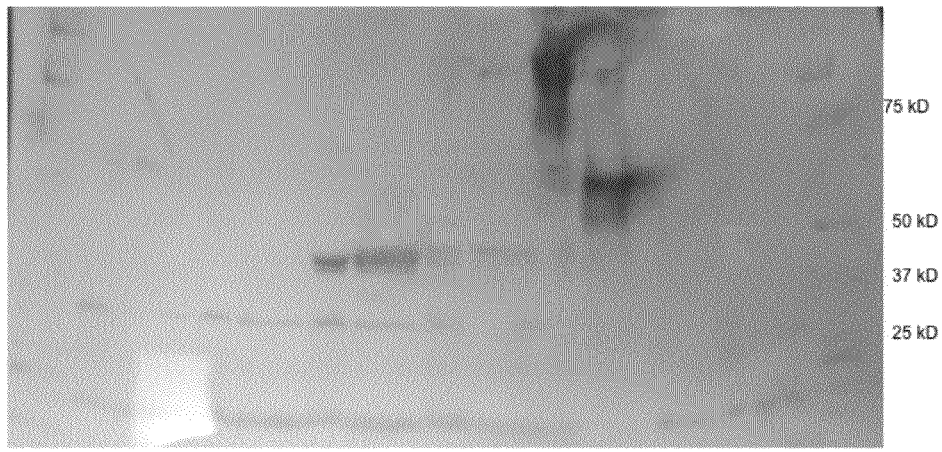

FIG. 20 depicts reactivity of native versus denatured truncated C2-3 of 22 amino acids in Min 19-pMBP. Different lengths of truncated C2-3 in Min-18-MBP constructs were prepared by SDM by primer extension. Recombinant products were affinity pure on maltose column, and 100 ng purified products were evaluated under both native and denaturing conditions. The construct of 22 amino acids from the C-terminus of the C2-3 microdomain was detectable in both native and denatured conditions. Moreover, C-terminal amino acids were critical for the native expression of FG loop B-cell epitopes, and C-7 constructs (both C-7 and C-7/N-15 constructs) failed to exhibit the indigenous FG loop B-cell epitopes. 1) pMal-p5E (SEQ ID 50) Min 23 empty loop 5 (without glyglygly linker, i.e., min18) (SEQ ID: 42); 3) pMal-p5E Min 23 empty loop 5+C16 C2-3 (SEQ ID: 259); 5) pMal-p5E Min 23 empty loop 5+ C-22 C2-3 (SEQ ID: 260); 7) pMal-p5E Min 23 empty loop 5+ C31 C2-3 (SEQ ID: 261); 9) IgE (BED) (SEQ ID: 1); 11) GFP (SEQ ID: 52)+ C-7 FG (SEQ ID: 262); 12) GFP+ N-15, C-7 FG (SEQ ID: 263).

DETAILED DESCRIPTION OF THE INVENTION

IgE-mediated allergic asthma and allergic inflammation affects 46 million US population and 300 million worldwide. Research on IgE molecules for a cure for IgE-mediated allergic diseases has been intense for decades. Spatial IgE receptor-binding B-cell epitopes defined according to X-ray IgE receptor-cocrystal (Garman et al., 2000, Nature, 406: 259), were engineered via the constraining platform designed by the lab. There is yet no active vaccine prepared based on preserving neutralizing IgE B-cell epitopes based on constraining secondary structure on thermostable protein scaffold. Vaccine-elicited antibodies to well-defined neutralizing IgE B-cell epitopes can prevent or neutralize IgE binding or sensitization to type I IgE Fc receptors (FceRIa).

Because IgE, complexed with vaccine-elicited anti-IgE is sequestered from binding to FceRIa, the immune complexes can be cleared from circulation or IgE-infested mucosal sites of the lung and the GI tract. The embodiment of this invention will also not cause cross-linking receptor bound IgE on sensitized mast cells/basophils since the IgE B-cell epitopes, which the neutralizing antibodies recognize, are blocked from interacting with the FceRIa receptor binding sites. Thus IgE sensitized mast cells/basophils can not be activated by neutralizing antibodies and undergo mast cells/basophil degranulation.

The feasibility of retaining the reconstructed, constrained three-dimensional B-cell epitopes was demonstrated by its capacity of being recognized by neutralizing antibodies under the native non-denaturing conditions. The embodiment of scaffolding with two to three successive, categorically different constraining molecular devices has not been undertaken. Straight forward synthetic peptide coupling to protein carrier led to random and/or linear peptide B-cell epitopes, and antibodies raised to the linear peptide epitopes do not cross-react or cross-neutralize native IgE proteins, nor host inflammatory cytokines, nor cross-react and neutralize pathogenic bacteria or viruses.

Although the knowledge exists concerning IgE loop sequences that directly bind to FceRIa by X-ray cocrystal, or secondary structures adjacent to the receptor-binding loop of IgE (Garman, 2000, Nature, 406: 259), there exists no enablement of translating the receptor-binding, loop antigenic sequences into B-cell vaccines that elicit neutralizing antibodies to the receptor-binding sites of IgE. The embodiment of the invention enables the native IgE loop sequences immunogenic for eliciting IgE neutralizing antibodies as protective allergy vaccine.

IgE in solutions maintains a closed dyad symmetry, slightly twisted for 3° at the C2-3 junction. This twisted angle ensures an asymmetric docking of IgE dimer on receptor molecules. Herein, we exemplify the two receptor-binding sites of IgE. The exemplification serves a heuristic attempt to describe the need for a constraining strategy for accommodating the receptor-contacting loop structure onto appropriate constraining scaffolds: b-strands or super b-strands, cysteine knots, and thermostable protein scaffold in toto serving as scaffolding for the IgE receptor-binding sites. Not only the receptor-binding sites but also the adjacent sites to the IgE receptor-binding sequences, to which interfering antibodies can be raised, serve as the druggable sequences for eliciting IgE neutralizing and/or receptor interfering antibodies. The embodiment includes the constraining both FceRI-receptor binding and receptor-interfering IgE sequences in super b-strands and/or cysteine knots as first and second-tiered constraining scaffold onto further a third-tiered thermostable protein scaffold.

X-ray structure of IgE/receptor complexes (Garman et al., 2000, Nature, 406: 259) showed that receptor D2 and D2-D1 linker exhibit asymmetric contact to different amino acid residues on both half molecules of IgE. There are two major recesses in the IgE receptor: the P426 and Y131 pockets. The BC, DE, C2-3L loops of one half IgE molecule, bind predominantly to the Y131 pocket over an 830 angstrom$^2$ surface, whereas four main amino acids of the FG loop (HLPR) (SEQ ID: 23) on the other IgE half molecule, bind the P426 pocket (named after the HLP (426) R) (SEQ ID: 23), spanning the D2 and D2-D1 linker of FceRIa. The P426 receptor pocket buries a large surface area of IgE predominantly the FG loop about 970 angstrom$^2$.

Surface areas of FG and antigenicity: The contact area of crucial FG loop of IgE with receptor's BC loop and D2-D1 linker covers a major stem area ~670 angstrom$^2$ of P426, and the C2-3 linker contributes at the receptor's FG loop tip area to ~300 angstrom$^2$ of P426. The four amino acids, HLPR (SEQ ID: 23) form intimate contact with about 450 angstrom$^2$ out of a total of 930 angstrom$^2$ space (the rest occupied by C2-3L), and the R residue of FG loop also buried deep in the Y131 pocket.

Overall, two asymmetric amino acid sequences of the dimeric CHe2-CHe3 of IgE heavy chain work in synergy to bind to the receptor D2 and D2-D1 linker to confer high affinity IgE binding to receptor in a one to one stoichiometry. The contact IgE residues to receptors are respectively C2-3L, BC loop, DE loop, and FG loop. The surface IgE receptor-binding loops are antigenic and solvent accessible according to B-cell epitope predictive algorithms, suitable for neutralizing antibody targeting. While all four FG loop core residues of one IgE heavy chain, i.e., HLPR (SEQ ID: 23), bind to the P426 pocket, the H residue of the FG loop and C2-3, BC and DE of the other IgE chain bind to the Y131 receptor pocket. Initially, the FG loop of IgE and predominantly the C2-3, BC and DE loops bind to a single receptor domain, the Y131 pocket, resulting in a low affinity interaction ($10^5$ M$^{-1}$) (Robertson, 1993, J. B. C., 268: 12736). Subsequently, engaging the entire FG loop (HLPR) (SEQ ID: 23) to D2-D1 linker of the P426 pocket along also with the C2-3 loop of IgE, and FG and C2-3 loops in concert, renders a high affinity binding to IgE ($10^{9-10}$ M$^{-1}$).

The binding energetics is the depiction of the energy landscape of the IgE ligand binding to the receptor, an integrated expression of enthalpy and entropy of the binding, which controls the folding of the respective contact of the loops between the D2-D1 domains of the FceRI receptors and IgE ligand. Thus to take the amino acids out of the context of the native constraining milieu without imposing a substitute constraining device or devices, i.e., preparing synthetic peptides onto KLH, BSA or viral like particle conjugates via direct chemical conjugation at the random locations of carrier proteins, or the straightforward use of two flanking cysteine linearly, leads to the loss of the native conformation.

One-step or single constraint for retaining native B-cell epitopes: Previously, the construction of monospecific neutralizing IgE B-cell epitopes in a special constrained format in the internal sequences of the GFP protein (SEQ ID: 52), which simultaneously also serves as the protein scaffold has been advocated (Chen, 2008, J. Immunol. Meth., 333:10). In this single-step constraint, the foreign loop epitopes are inserted or replacing the endogenous loop of the protein, which also serves as the scaffold for exhibiting the inserted sequences. The demand of the scaffold protein to perform is two-fold in accommodating the inserted determinants as well as in serving as an overall protein scaffold.

Two- to three-step, or multiple constraints for retaining B-cell epitopes: the embodiment of the invention. To constrain the above epitopes, a constraining platform is required. This prompts the invention of the first tier in seeking a stable pair of b-strands within the four receptor-binding loops of IgE. A series of truncation mutants of the four receptor-binding IgE segments (C2-3, BC, DE, and FG) were prepared unto GFP, and the native epitopes were expressed and test with neutralizing anti-IgE under native conditions, devoid of reducing agents, heating, and denaturing SDS by native western blots. The core embodiment of this invention is to determine the existence of such a super b-strands which can serve as a universal clamps for accommodating as many pertinent loops to the native state critical for invoking a pharmacological response, or serving as the antigen or vaccine for eliciting neutralizing antibodies against IgE molecules or proinflammatory cytokines, or blocking bacterial or viral infectivity.

The embodiment of this invention resides in enabling a super-stable loop epitope (preferably with the proline as a kink) with a flanking super b-stranded scaffold. The embodiment of the invention is to invoke the IgE B-cell vaccines with one of the four FceRIa contacting IgE B-cell epitopes as monospecific vaccine alone, and in combination as a combinatory polyvalent vaccine. Taken together, we therefore reason that antibodies to a properly designed FG loop and other receptor-binding or receptor-interfering sequences can similarly efficiently prevent IgE binding to receptor via direct blocking or steric hindrance, due to blocking on one half molecules at the P426 pocket, and in synergy with blocking Arg$^{427}$ of the other half molecule at the Y131 pocket. Similarly, constrained C2-3 loops in super b-strands and/or cystine-knotted on a thermostable, immunogenic protein scaffold, elicit neutralizing anti-IgE that block IgE binding to receptor at the Y131 and P426 sites. DE and BC core loop sequences constrained in super b-strands and/or cystine-knotted onto protein scaffold, elicit neutralizing antibodies that block at the Y131 sites. Direct blocking at one IgE ligand binding site causes also steric hindrance at the P426 and vice versa.

Receptor-blocking neutralizing antibodies elicited from properly scaffolded receptor-binding or receptor interfering IgE sequences protect human IgE from binding to human high affinity IgE receptors on mast cells, basophils, dendritic cells, neutrophils and eosinophils.

Thus, the descriptive sequence knowledge based on X-ray cocrystal is directly enabled into a three dimension preserved conformation by the embodiment of this invention, and is translated into a pharmaceutical product for treating IgE-mediated allergic diseases. Specifically shown in Examples: (i) With regard to specific FG loop, we showed that the FG loop is naturally, most robustly scaffolded within its flanking b-strands, which is also capable of super performance in that the b-strands of the FG loop also constrains core loop sequences of BC, DE and C2-3L loops.

(ii) It is well known that the cystine stabilized b-sheets (CSB) containing miniprotein, cystine knots (CK), exhibits a broad range of bioactivities and are exceptionally stable (melting/denaturing temperature (Tm>100° C.) being resistant to chemical, thermal and enzymatic degradation. Therefore, the FG loop with the native b-stranded scaffold can be further scaffolded in the cystine knot stabilized b-sheets. (iii) The doubly constrained FG loop can co-fold with GFP protein (Tm~100° C.) that supports the overall cystine knots-constrained FG loop as well as activating helper T-cells required for antibody production as shown in our lab and affinity maturation. The fluorescence of GFP also serves as a first indication for the integrity of the fusion protein.

Candidacy of Linear B-Cell Epitopes as Neutralizing B-Cell Vaccines

Conception of monospecific B-cell epitope and its conjugation as synthetic peptide unto an immunogenic protein was pioneered by M. Atassi, Richard Lerner and Fred Brown in the 80's (Atassi, 1978, Immunochem., 15: 909; Rowlands, 1983, Nature, 306: 694). However through extensive studies of numerous potential B-cell candidate epitopes, B-cell epitopes randomly conjugated to protein carriers are thermodynamically unpredictable, and exhibiting in a random, distorted conformation unlikely to present the native antigenic epitopes, resulting in frequently linear epitopes recognized by the denatured PAGE/western blot condition by anti-peptide antibodies (Maloy, 2012, Curr. Prot. Immunol. Unit 9.4).

The linear epitope is likely to represent a minor folding pathway of B-cell epitope presentation similar to the presentation of the fraction of denatured protein co-existing with the native protein. The other source of anti-peptide antibodies is derived from the degraded products of the vaccine, which assume linear or amino acid sequence dependent B-cell epitopes recognized by the host antibody repertoire. This embodiment of the invention disables generating antibodies against the pool of spurious sequence-dependent linear epitopes, which are of insignificant import in serving as prophylactic or anti-inflammatory antibodies. The anti-linear B-cell epitopes antibodies can serve a minor role in clearing the effete life cycle products of degraded IgE, inflammatory proteins, cytokines, protein kinases, transcription factors. While denatured B-cell epitopes of the viral and inflammatory proteins can be cleared by the anti-peptide antibodies, these antibodies do not neutralize active ongoing bacterial and viral infectious agents, nor neutralize inflammatory protein, IgE and cytokines to achieve therapeutic effect.

Although anti-linear peptide antibodies are dominant in the reagent markets, this approach of random conjugation of B-cell epitopes to proteins is rarely relevant for the purpose of preparing protective vaccines. For decades randomly coupled synthetic peptides has not led to anticipated B-cell vaccine candidates in order to elicit protective neutralizing antibodies, although linear peptides are considered CTL vaccine candidate since class I MHC typically accommodates linear peptide sequences, and not native peptides (Fridman et al. 2012, OncoImmunol, 1: 1258).

Chemical conjugation of IgE B-cell epitopes to protein carriers without constraint, invariably leads to distorted conformation of the epitope, or in an extended linear display, which was detected in SDS extended linearized form detected by antibodies to IgE synthetic peptides randomly coupled to the protein carrier. Chemical coupling reagents including homo- and hetero-bifunctional reagents such as MDS and SPDP, and random chemical coupling reagents such as carbodiimide and glutaraldehyde have been deployed for raising only anti-linear peptide antibodies. And there are numerous conjugating compounds developed by the reagent companies, Sigma, and Pierce. Random chemically conjugated, unconstrained B-cell epitopes onto the Qbeta structural protein in a viral like particle (VLP), an platform initially developed for eliciting linear CTL epitopes are subject to distortion of the native conformation (Bachmann et al, 2002, U.S. Pat. No. 7,128,911).

Embodiment of this invention enables active site specific viral B-cell vaccines: Structural vaccine design pertaining to B-cell vaccine epitope is gaining increasing importance in major viral infectious diseases, i.e., human immunodeficiency virus (HIV) (Johnston and Fauci, 2007, N. Eng. J. Med., 356: 207). The visualization of the protective surface by b12 and ARC01 elucidates both the CD4 binding site (CD4bs) of gp120 (interacting with host CD4 molecule) and a mannose-binding site surface. To form a mimetics for a large complex surface or carbohydrate-binding site via protein fragments or genetically modifying the whole antigenic surface via global antigen resurfacing has met with major computation challenges. The embodiment of this invention indicates that critical fragments of contact residues of CD4bs may be inserted into the super b-strands and the cystine knots on the support of a protein scaffold.

Gp41 is a subunit of the envelope protein complex, non-covalently bound to gp120 and provides a second step for HIV's entry to the cells via contacting host cell CD74 (Zwick at al., 2001, 75: 10892). Thus blocking gp41 with neutralizing antibodies can attenuate viral infections. The invariant 30 amino acids of gp41 of HIV in the membrane proximal region can interact with CD74 and cause enhanced infectivity. In the embodiment of the invention, CD74 contact loop epitopes can be inserted into the super b-strands, in the cystine knots on the thermostable protein scaffold.

In the influenza virus, the hemagglutinin binding the sialic acid accounts for infectivity. The two glycoproteins of the influenza virus membrane, hemagglutinin (HA) and neuraminidase (NA), both recognize sialic acid (Gamblin and Skehl, 2010, J. B. C., 285: 28403). Initiation of virus infection involves multiple HAs binding to sialic acids on carbohydrate side chains of cell-surface glycoproteins and glycolipids. Following virus replication, the receptor-destroying enzyme, NA, removes its substrate, sialic acid, from infected cell surfaces so that newly made viruses are released to infect more cells. Both activities are the targets of antibodies that block infection. The embodiment of this invention is to place the core loop region of neuraminidase in the super b-strands (FG), in the cystine knots on a scaffold protein.

The binding depression surrounds the sialic acid domain with three primary regions of the hemagglutinin structure. This region consists of a loop-helix-loop (130 loop-190 helix-220 loop) structure forming the triangular opening into the beta-sheet depression. The core loop regions, i.e., the 130 loop and 220 loop are accessible to the aqueous phase in triplicates and are target for loop-specific mono-specific neutralizing antibodies. In the embodiment of this invention core loop sequence of 130 and 220 loops can be inserted in the super-b-strands (FG) in the cystine knots on a protein scaffold as HA-specific B-cell vaccines.

Despite the knowledge of three dimensional structures of influenza virus, respiratory syncytial virus (RSV) and HIV protective proteins, active vaccines with monospecific neutralizing B-cell epitopes to protect against viral infections are not forthcoming with synthetic peptides conjugated to protein carriers. The embodiment of FG loop, and BC, DC, C2-3 linker loop-specific vaccine in a highly constrained super b-strands on a stable protein scaffold, can be extended to similarly molecular engineered active site (such as FG loop)-specific active microbial vaccines such as GP120, and GP41-specific active HIV vaccine, human HA-specific flu vaccine, and human RSV vaccines (Dudas and Karron, 1998, Clin. Microbiol. Rev., 11: 430).

Embodiment of this invention as a remedy for linear B-cell epitopes: The effort herein is to invent a general antigen display via a combined effort to include scaffolding the B-cell vaccine candidate loops into the indigenous super b-strands of truncated FG microdomain, with or without further constraint into the thermostable cystine knots, integrated onto the thermostable protein scaffold.

This approach enables a new platform for discovery of the critical monospecific B-cell vaccines for major IgE-mediated, cytokine-mediated inflammatory diseases, and major viral infectious diseases. Approach of random synthetic peptide conjugation to protein carrier leads to linear peptide epitope presentation. The embodiment of this invention enables the grafted B-cell epitopes to assume the native, three dimensional antigenic B-cell neutralizing epitopes The embodiment of the invention enables treatment of human IgE-mediated allergy therapy: Specific immunotherapy (SIT). SIT is an FDA-approved prevalent therapy, based on induction of specific anergy by regulatory CD4 T-cells and immune deviation of CD4 T-cells. Extracts of allergenic source materials have been employed, which require safety supervision.

The embodiment of this invention for preparing FG, C2-3, BC and DE loop monospecific and polyvalent IgE B-cell vaccines in FG super b-strands offers expediencies over productions and clinical testing of a host of recombinant allergens. The IgE loop-specific B-cell vaccine ensures the safety in contrast to crude allergen extracts. As a pan-IgE neutralizing vaccine, it covers diverse allergen specificities, and its efficacies and safety can be evaluated by measuring the protective anti-IgE loop in contrast to immune deviation and induction of allergen-specific regulatory T cells (Treg).

By targeting the receptor-binding and receptor interfering sequences of human IgE, a commonly shared antigenic epitope, this active vaccination with conformational constrained IgE B-cell active vaccine can alleviate a wide spectra of IgE-mediated diseases caused by a myriad of allergens. The cost/benefit ratios of the FG loop vaccine over passive monoclonal antibodies are favorable in extending the patient base. Vaccination via mucosal immunization can achieve protection at the mucosal organs, lungs and the GI tracts. The safety of the active vaccine will be ensured by a regimen for booster-required six month-treatment duration windows similar to that of the passive anti-IgE antibodies.

One aspect of embodiment of the invention resides in immunogenicity of the protein scaffold in controlling the duration of anti-B-cell epitope response. The protein scaffold that supports monospecific B-cell epitope constrained by the super b-strands with or without further constraint of the cystine knots, can recruit CD4 helper T-cells that activate B-cells specific for native IgE B-cell epitopes. The bifunctional protein scaffolds include but are not limited to green fluorescent protein and maltose-binding protein. The longevity of anti-IgE responses can be moderated by a vaccine booster regimen. Without a booster dose, CD4 helper T-cells become quiescent and neutralizing anti-IgE responses decline and basal levels of IgE resume. The recovered levels of autologous IgE also cause tolerance of IgE-specific B-cells. These processes ensure that no persistent anti-IgE responses cause long-term suppression of circulating IgE or mucosal IgE. The embodiment of this invention also can sustain high titers of neutralizing anti-bacterial and viral antibodies with vaccine boosting for activating memory CD4 helper T-cells specific for protein scaffold.

Another embodiment of the invention enables treatment of IgE-mediated allergy in pet animals and economically useful large animals Because of the identity of the FG loop core sequence among humans and non-human primates, it efficacies and safety can be further tested in these species. Veterinary IgE B-cell vaccines can be prepared by replacing the native FG loop sequences of human FG super b-strands on a protein scaffold with FceRI-binding IgE sequences of feline, canine, equine, and bovine species.

EXAMPLES

Example 1

Antigenicity: Preservation of Constrained Human IgE Mono-Specific Subunit Vaccine Epitopes The super b-strand flanking sequences and the replaced loops: The major embodiment of the invention is to enable the most rigid b-strands energetically favorable for accommodating the foreign insertion loop epitope. The discovery step consists of determining a robust IgE FceRIa binding B-cell epitope region or microdomain that can be molecularly presented by a thermostable protein scaffold. Following this identification, the region or microdomain can be further trimmed to identify the critical rigid secondary structure, flanking b-strand that present the endogenous and swaps with foreign loop epitopes.

Figure 1:
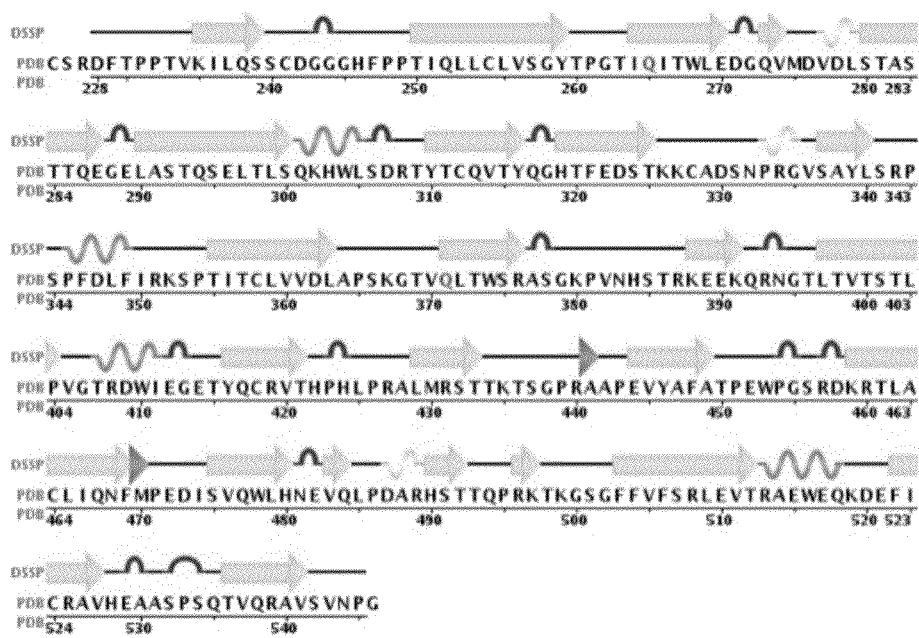
FIG. 1 depicts the primary sequence and secondary structures of human IgE CHe2 to CHe4 domain. The secondary sequence was assigned according to 1FP5 of the PDB, according to crystal structure analysis of the human IgE-Fc epsilon3-Fc epsilon4 fragment by Wurzburg et al., 2000, Immunity, 13: 375.

FIG. 1 describes sequences from the primary amino acid sequences derived from human IgE constant regions sequences 1FP5 of the PDB database. The sequences of interest are from the four high affinity IgE receptor-binding regions and the core loop sequences: C2-3 region is defined as RTYTCQVTYQGHTFEDSTKKCADS NPRGVSAYLSRPSP (SEQ ID: 4) (308-334) cloned into the GFP for truncation for the minimal sequences required for presenting native IgE B-cell epitopes. NPRGVS (332-337) (SEQ ID: 110) is the core loop sequences that contact the IgE FceRIa. VDLAPS (362-366) (SEQ ID: 114) is the receptor-contacting core loop sequence of the BC region. RNGT (393-396) (SEQ ID: 124) is the receptor-contacting core loop sequence of the DE region.

TRDWIEGETYQCRVTHP (SEQ ID: 36) (HLPR) (SEQ ID: 23) ALMRST (SEQ ID: 40) TKTSGPR (SEQ ID: 126) (408-440) is the full length FG region (SEQ ID: 10). The core loop sequence (HLPR) (SEQ ID: 23) is flanked by two b-strands as also scaffold that can present the native FG core loop sequence HLPR, and also can present core loop sequences of C2-3, BC or DE core loop sequences for native B-cell epitope presentation.

Discovery of this embodiment consists of three enablement steps: (i) selecting an intrinsically robust scaffold; (ii) delineating the minimal length of the flanking amino acids for the loop epitope; (iii) replacing the native loop epitope with foreign epitope.

Enablement of super b-strands of the FG microdomain: The selection of an intrinsically stable IgE epitope was first dissected by expression the respective C2-3, BC, DE FG region (or microdomain) and/or a contiguous C2-3/BC/DE/FG complete region (minidomain) on the N-terminus of GFP, and the immune reactivities to neutralizing anti-IgE under native conditions were evaluated.

Figure 2:
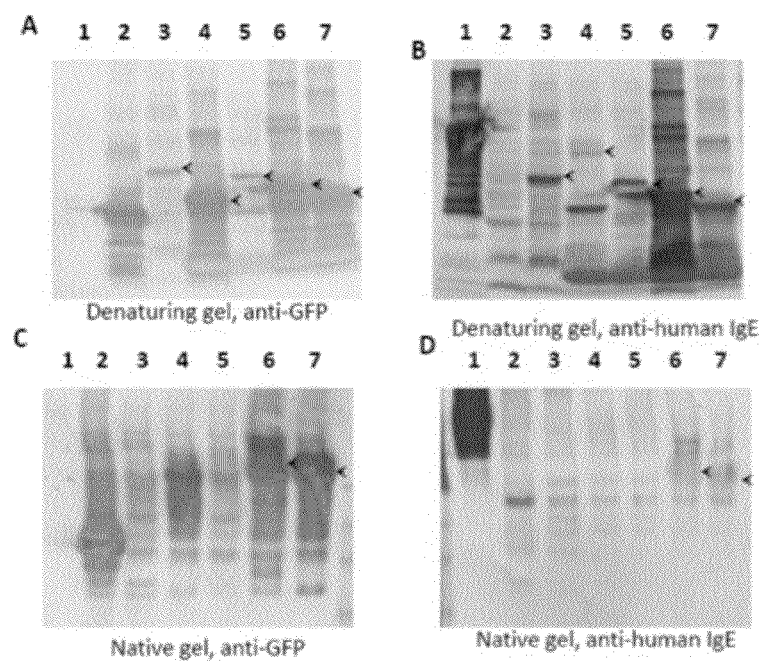
FIG. 2 depicts expression of mini- and micro-IgE-GFPuv fusion proteins. The mini-IgE domain (including C2-3 linker, BC, DE and FG loops) and 4 micro-IgE domains (C2-3 linker, BCDEFG, DEFG and FG) were inserted into the N-terminal of GFPuv to form IgE-GFPuv fusion proteins. The fusion proteins were expressed and analyzed by denaturing gels (A and B) and native gels (C and D) against anti-GFP antibodies (A and C) and anti-human IgE antibodies (B and D). Under denaturing conditions, all mini-IgE-GFPuv and micro-IgE-GFPuv proteins had strong reaction with anti-IgE antibodies (B). Two of the micro-IgE-GFPuv, DEFG-GFPuv and FG-GFPuv, kept the strong reaction with anti-IgE antibodies under native conditions (D). The sample loading orders were: 1) Human IgE; 2) wtGFPuv; 3) pMini-IgE-GFPuv; 4) pC2-3-GFPuv; 5) pBCDEFG-GFPuv; 6) pDEFG-GFPuv; and 7) pFG-GFPuv.

As shown in FIG. 2, the complete region of C2-3/BC/DE/FG mini-IgE domain is under-expressed according to GFP under both native and denaturing conditions (lane 3, Panel A and Panel C), while IgE reactivities were noticed under denaturing conditions but not under native conditions, indicating the folding of mini-IgE domain negatively affects the conformation of GFP, and despite the preservation of linear denatured B-cell epitopes, the critical native IgE B-cell epitopes were however not expressed. In contrast, C2-3 microdomain expressed on N-terminus of GFP caused strong expression of GFP detected by both denaturing and native conditions, indicating favorable GFP folding and expression (lane 4 of FIG. 2 Panel A and B).

Despite the favorable GFP folding in both native and denaturing conditions (lane 4, Panel A and C) and detection of the C2-3 B-cell epitope strongly under denatured conditions (lane 4, Panel B), C2-3 epitope was non-detectable under native conditions (lane 4, panel D). This indicates that C2-3 folding appears restricted only to the native chemical milieu of IgE molecules, and the native conformation is lost upon cloning onto GFP protein scaffold. This further indicates that the b-strands flanking the C2-3 are incapable of sustaining the presentation of the indigenous C2-3, and suggests that this may not sustain the conformation of the molecularly grafted foreign B-cell epitopes, i.e., a candidate for the super-b-strands that can accommodate promiscuously a diverse B-cell antigenic loop epitopes.

Next, C2-3 deleted from the mini-IgE domain also leads only to expression of the linear epitope detected under denaturing conditions (lane 5, Panel B). Importantly, further truncation of BC in addition to C2-3 leads to strong augmented expression of GFP under both denatured and native conditions, indicating the dual microdomain construct does not affect the conformation of GFP (with detected fluorescence), and importantly leads to the expression of immune reactive DE and FG B-cell epitopes strongly under both denatured and native conditions. Lastly, the single microdomain FG construct caused also strong expression of native GFP conformation (lane 7, Panel C) and the native expression of FG loop determinant (lane 7, Panel D). Therefore the discovery of the robust chemical structure, the super b-strands in FG microdomain, which constrains the core FG loop, serves as the foundation for its use as a key conformation constrainer for not only FG core loop but also core loops of other IgE microdomain IgE, and extending to protective B-cell epitopes in microbial infectious diseases.

Delineation of the Super-b-Strands in the Truncated, Minimal FG Microdomain

1. Strategy of Constraining FG Loop Antigen onto GFP Scaffold

Figure 3:
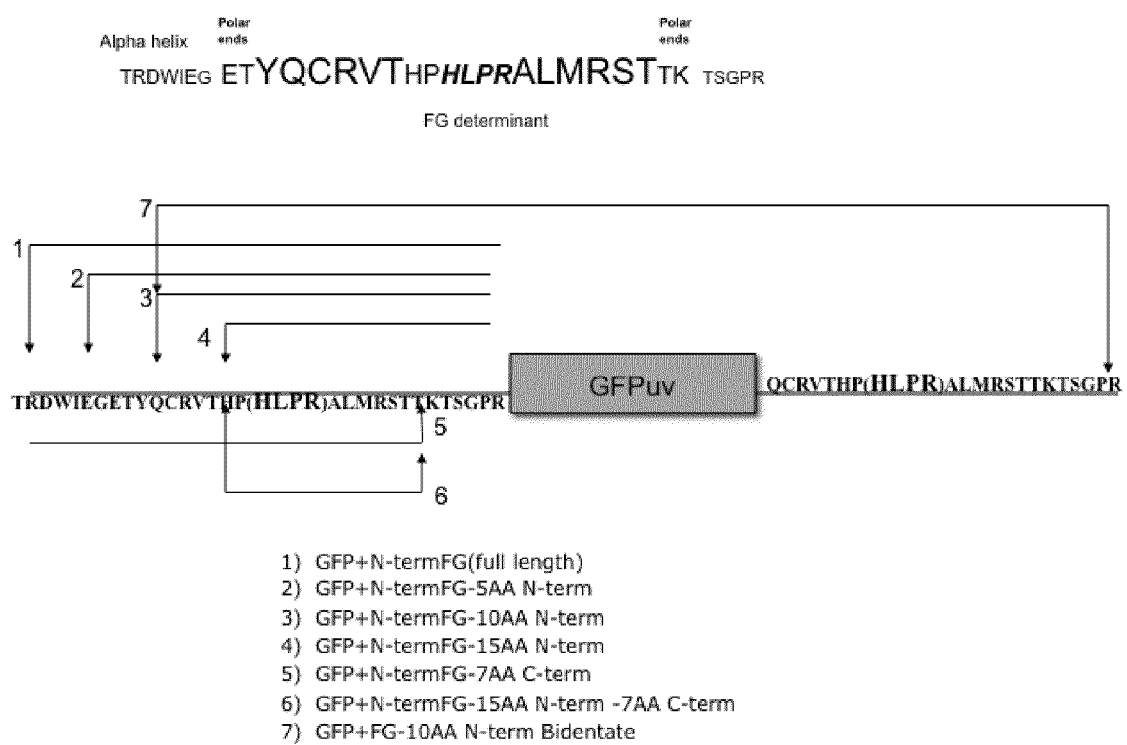
FIG. 3 depicts mapping super b-strands of FG microdomain onto GFP. Synthetic oligonucleotides corresponding to various truncated N- or C-termini of the human FG loop amino acid sequences were ligated to the N-terminus of GFP$_{UV}$ (with c-His constructed in the lab) by assembly PCR reactions. Suitable lengths (-5AAN, and -10NAAN) were determined as minimal sequences for expressing indigenous native human FG loop sequence, HLPR. The diagram showed that the full length FG microdomain (amino acids, 413-439) (SEQ ID: 10), including the FG core loop (HLPR) (SEQ ID: 23) flanked by the b-strand sequences (QCRVTHP) (SEQ ID: 36) and (ALMRST) (SEQ ID: 40), was prepared by PCR using the human IgE heavy chain gene as a template, ligated by assembly PCR at the N-terminus of GFP. Various 5' (N-) and 3' (C-) truncations were performed with the arrow depiction, and the orientation of FG super b-stands was depicted on both the N- and C-terminal of GFP. Lane 1-7: 1) N-termFG (full length) (SEQ ID: 10); 2) FG-5AA N-term (SEQ ID: 11); 3) FG-10 AA N-term (SEQ ID: 13); 4) FG-15 AA N-term (SEQ ID: 16); 5) FG-7AA C-term (SEQ ID: 262); 6) FG-15 AA N-term-7AA C-term (SEQ ID: 263); 7) FG-10AA N-term (SEQ ID: 13) Bidentate.
Figure 4:
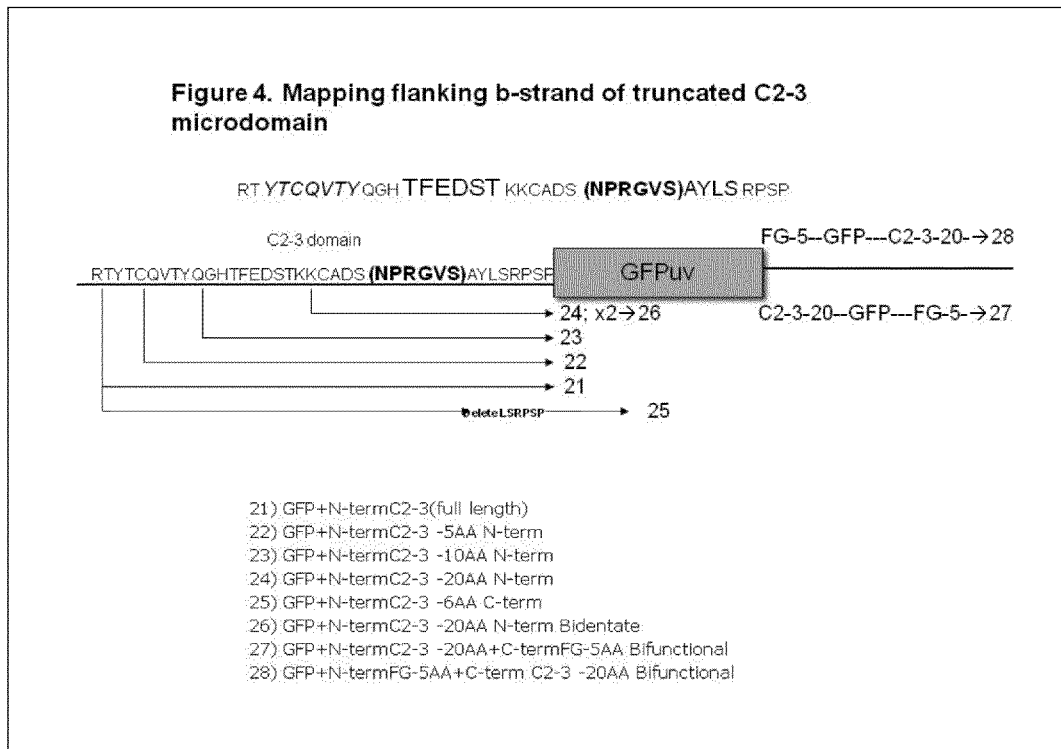
FIG. 4 depicts mapping flanking b-strands of truncated C2-3 microdomain. The diagram showed that the full length C2-3 microdomain (amino acids, 308-345) (SEQ ID: 4), including the C2-3 core loop (NPRGVS) (SEQ ID: 223) flanked by the b-strand sequences (TFEDST) (SEQ ID: 133) and (AYLS) (SEQ ID: 134), was prepared by PCR using the human IgE heavy chain gene as a template, ligated by assembly PCR at the N-terminus of GFP. Various 5' (N-) and 3' (C-) truncations were performed with the arrow depiction, and the orientation of truncated C2-3 are depicted on both the N- and C-terminal of GFP as prepared in the single, bidentate and bifunctional orientations. 21) N-termC2-3 (full length) (SEQ ID: 4); 22) N-termC2-3-5AA N-term (SEQ ID: 256); 23) N-termC2-3-10AA N-term (SEQ ID: 252); 24) N-termC2-3-20AA N-term (SEQ ID: 254); 25) N-termC2-3-6AA C-term (SEQ ID: 255); 26) N-termC2-3-20AA N-term Bidentate (SEQ ID: 254); 27) N-termC2-3-20AA+C-termFG-5AA Bifunctional (SEQ ID: 254)+ (SEQ ID: 12); 28) N-termFG-5AA+C-term C2-3-20AA Bifunctional (SEQ ID: 12)+ (SEQ ID: 254).

To determine the super-b-stands as scaffold, truncation was made on the N-terminal ends of both C2-3 and FG segments. This construct strategy consists of two molecular matrix layers of super-beta strands, integrated with a thermostable protein scaffold. FIG. 3 diagram showed that the design construct of FG microdomain at the N-terminus of GFP scaffold, with deletion of the microdomain from the N- and C-terminus. FIG. 4 showed molecular integration of C2-3 microdomain into GFP scaffold, with truncations from the N- or C-terminus.

Figure 5:
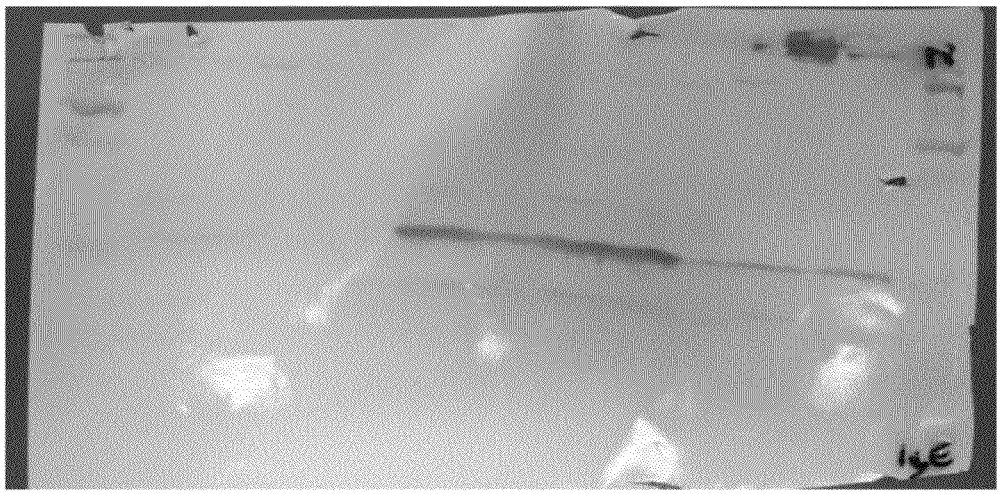
FIG. 5 depicts reactivities with native FG loop B-cell epitopes, flanked by FG super b-strands on the truncated FG microdomain. Full length of FG and C2-3 were prepared with oligonucleotides with HindIII cloning sites and recombined with GFP$_{UV}$. Site-directed mutagenesis (SDM) with different truncations from N- and C-termini was performed with primers devoid of different length of sequences. Recombinant clones were obtained by high efficiency bacterial transformation, and recombinant protein prepared by batch purification on the IMAC bead. To detect the native conformation, the affinity pure FG-GFP and C2-3-GFP, truncated as design were not boiled and the running sample buffer did not contain 2-ME reducing agent, and 1% SDS substituted with 1% CHAPS; the running buffer contains 0.1% CHAPS. The gel was transferred in 0.5% methanol in 0.5% CHAPS and probed by neutralizing polyclonal goat anti-IgE antibodies (pAb, of several sources from the NEN, Clontech, and the Bethyl lab). 1) FL C2-3 (SEQ ID: 4); 2) N-10 AA C2-3 (SEQ ID: 252); 3) N-15 AA C2-3 (SEQ ID: 253); 4) N-20 AA C2-3 (SEQ ID: 254); 5) C-6 AA C2-3 (SEQ ID: 255); 6) FL-FG (SEQ ID: 10); 7) N-5 FG (SEQ ID: 12); 8) N-10 FG (SEQ ID: 13); 9) N-15 FG (SEQ ID: 16); 10) GFP (SEQ ID: 52); 11) IgE (SEQ ID: 1).

We test whether the FG loop may be delineated and its antigenicity studied by co-folding at the N-terminus of GFP. The total FG loop (407-440), including the FG core loop (HLPR) (SEQ ID: 23) flanked by the b-strand sequences (QCRVT) (SEQ ID: 38) and (LMRST) (SEQ ID: 40) was prepared by PCR using the FG-GFP template or human IgE heavy chain cDNA as templates, and then ligated at the N-terminus of GFP by assembly PCR. In order to assess the native FG determinants, samples were neither heated nor treated with 2ME, and separation and transfer were conducted in native buffer, substituting SDS with CHAPS. FIG. 5 showed that N-terminal deletion of five, ten and fifteen amino acids, did not affect the expression of the core FG loop epitope (lane 7, 8, 9), and provided three potential enablement constructs of inserting foreign B-cell epitopes to replace the native core loop of the FG loop.

In contrast, as shown in FIG. 5, C2-3 is not capable for providing the b-scaffolding device in that neither the full C2-3 microdomain nor its trimmed constructs: N minus ten, or fifteen or twenty amino acid deletion eliminates the native immunoreactivity. The full length DE microdomain augments reactivity with neutralizing anti-IgE (compared to Lane 6, Panel D of the previous FIG. 2). In one aspect of the embodiment of this invention, DE microdomain integrated with GFP, can be similarly truncated for determining presentation of the native DE loop sequences, and extended to FceRI interfering sequences other than FceRIa receptor binding sequences of IgE. The evidence indicates that the native b-strands flanking the FG loop are the most robust b-strands amongst four receptor-binding loops due to its reactivities under native conditions to the polyclonal neutralizing anti-IgE. The polyclonal goat anti-IgE neutralizing antibodies blocked IgE binding to solid phase FceRIa receptors.

2. Swapping the Foreign B-Cell Antigenic Epitopes Among the Super-b-Strands onto GFP Protein Scaffold The embodiment of this invention is therefore to utilize the rigidity of the original native b-strands that flank the antigenic loop in a b-hairpins or super b-strands may serve as a first order constraining molecular clamps not just for the indigenous sequences. And thus this leads to the inventive concept that foreign loop sequences replacing the endogenous loop sequence, i.e., the FG core loop sequences can also maintain the necessary conformation of the super-b-strands, which in turn can constrain the foreign replacement loops, and the overall productive folding of the foreign B-cell loop in the b-strands can also help the folding of the supporting protein scaffold.

In order to ascertain the specificity of FG loop sequence detection by neutralizing anti-IgE, the native loop sequence is deleted from the N-5 FG construct. As shown in FIG. 6, importantly the elimination of the loop antigenic epitope removes its specific reactivity to the neutralizing anti-IgE (lane 4, panel A). This indicates that this precise location being the antigenic sites being accommodated by the flanking b-strands is confirmed, and can serve a site for exchanging or swapping with other foreign loop sequences.

FIG. 6 also confirmed that with FG microdomain derivatives with N-5 and N-10 deletion are strongly reactive to detected by neutralizing anti-IgE under native conditions (lane 2 and 3, Panel A, FIG. 6), while the FG loop with the core loop sequence (HLPR) (SEQ ID: 23) deleted was not detected (lane 4, panel A of FIG. 6).

The conformation of the FG loop is robust. It is possible that both the flanking b-strands of the FG loop [QCRVT (SEQ ID: 38); LMRST (SEQ ID: 40)] and the proline 422 as a kink of the HP (422) HLPR (SEQ ID: 108) core loop sequence work in synergy for forming this extra-stabilized hairpin FG loop. The grafting of other loop sequences into the FG b-stand scaffolding clamps renders it a robust central platform for preparing future multivalent neutralizing IgE epitopes as the vaccine. The conception of this invention is validated and materialized by replacing the native FG core loop sequences with three other IgE B-cell epitopes, C2-3, BC, and DE epitopes. As shown in FIG. 6, it is of critical importance that this strategy of accommodating the other there human neutralization sequences into the deleted core residues that lead to restoration of the filled-in swapped sequences: RNGT (SEQ ID: 124) (the DE loop core sequence, lane 5), NPRGVS (SEQ ID: 110) (the C2-3L loop core sequence, lane 6) and DLAP (SEQ ID: 120) (the BC loop core sequence, lane 7) by native western to pAb under native conditions, and BED IgE as positive control (Ln 8).

FIG. 6 showed that the FG-GFP with N-5, and N-10 truncations, or with various swapped loops was detected under native conditions as a native tetramer of 120 KDa by neutralizing pAb: polyclonal goat anti-IgE neutralizing antibodies. It should be pointed out that since GFP, under native conditions, is present as a dimer or tetramer by the X-ray data (1GFL, PDB bank), the detectable FG loop swapped sequences in GFP protein scaffold migrated at the 120 KDa. In contrast, these recombinant IgE-epitopes GFP constructs also reacted with anti-GFP with the corresponding 35 KDa band under denatured conditions, shown in similar order in FIG. 6B. We have since then focused on the C2-3-GFP and FG-GFP constructs due to their respective important role in docking to high affinity IgE receptor; in particular the FG loop appeared to bind to neutralizing antibody, Xolair according to the computer fitting, epitope docking model (Zheng et al., 2008, B.B.R.C., 375: 619).

The expression of GFP moiety in the above constructs is compared. The same material, FG loop (N-5) and (N-10) was detected as a 35 KDa band with anti-GFP under denatured conditions (lanes 2,3 and 4, Panel B), while the empty FG loop was detected with less intensity by anti-GFP, indicating that the presence of the native endogenous sequence appears to stabilize the expression of GFP scaffold, and/or the presence of the native loop sequence not only prevents the distortion of the FG microdomain, but the integrity of FG microdomain in turn also supports the folding and integrity of GFP. Thus protein folding properly consummated is dependent on integrity of the secondary b-strand structure, which flanks the endogenous loop sequences.

Although C2-3L can be constrained within the internal loop of GFP (SEQ ID: 52) (Chen, 2008, J. Immunol. Meth., 333: 10), it is not amenable to other loop sequence insertions. Thus reproduction of all four FceRI binding IgE B-cell epitopes by swapping and replacing the native FG loop sequences with other IgE B-cell epitopes, indicates strongly that the FG loop flanking b-strands constitutes the super b-strands for scaffolding pharmaceutically important B-cell epitope loop sequences, including receptor-binding IgE B-cell epitopes.

3. Further Validation of the B-Cell Epitope Swapping in the Super b-Strands of FG Domain In yet another verification and extension of the embodiment of the invention with loop sequences swapped in dual vectors, the swapping of BC, DC and C2-3 core loop B-cell epitope is replaced in both N-5 and N-10 super-b-strand scaffold of the FG microdomain. The comparison of native gel reactivity with neutralization is performed with loading with 200 ng of purified recombinants products via the His-tag on the C-terminal of GFP scaffold.

As shown in FIG. 7A, the full length DE loop microdomain on GFP protein scaffold maintains the native conformation reactive to neutralizing anti-IgE (lane 3, FIG. 7A). This confirms the previous observation that DE/FG-GFP construct maintains the stronger reactivity than that of FG microdomain alone integrated in GFP (lane 6 versus 7, Panel D of FIG. 2). This strongly suggests that b-strands of DE microdomain may serve as another set of super b-strands for accommodating other B-cell loop epitopes. A critical important point is that N-5 and N-10 FG truncated constructs can serve in concert to optimize accommodation of the three IgE core loop B-cell epitopes selectively. Thus FG N-5 construct accommodates optimally for RNGT (SEQ ID: 124) and well for NPRGVS (SEQ ID: 110) but not for DLAP (SEQ ID: 120), while N-10 construct accommodates all three, and are best for DLAP (SEQ ID: 120) and NPRGVS (SEQ ID: 110). Thus to materialize a native loop of a B-cell epitope, insertion in both the super-b-stranded, differentially truncated according to N-10 versus N-5 FG construct in GFP scaffold, maximizes the optimal outcome.

Under denaturing conditions, FIG. 7B showed that full length DE on GFP protein scaffold expressed the linear IgE epitopes. Products expressed by FG N-5 versus N-10 on GFP protein scaffold, exhibited the same intense denatured, linear B-cell epitopes, despite the deletion of the FG core loop epitope, the residual super-b-strands and the neighboring amino acids exhibited week reactivity under denatured conditions with anti-IgE.

Moreover, deleting the endogenous loop sequences (lane 3 and lane 4) interfered with the overall folding of FG microdomain, which also distorted the folding of GFP as shown by loss of reactivity under even denatured conditions, detected with anti-GFP, since equal amount of sample of 200 ng were mounted for all samples. In most instances, reactivities to denatured products did not have bearing to the native reactivities, since most chemically conjugated peptides to carrier proteins elicit only anti-peptide antibodies reactive with linear peptides under denatured conditions. In contrast, native B-cell core loop B-cell epitopes, flanked by super b-strands onto GFP protein scaffold, can exhibit both native conformation-sensitive, native B-cell epitopes under non-denaturing conditions and linear epitopes under denaturing conditions.

Under these circumstances, the intensity of expression of C2-3, BC, and DE core loop sequences in the FG N-5 and N-10 constructs under denatured conditions also correlated with the relative intensity of native epitopes stoichiometrically.

GFP, under native conditions, is present as a dimer or tetramer according to numerous submitted and published X-ray data to the PDB bank (1GFL). This explained the higher molecular weight of the FG super-b-strands of different truncations on GFP protein scaffold exhibited the molecular weight of the tetramer. In contrast, as shown in Panel A, the various FG and the truncated constructs exhibited a corresponding 35 KDa band for each species under denatured conditions (Panel B, FIG. 7B).

Replacement mutants with the crucial human or mouse IgE receptor-binding four to six amino acids (i.e., receptor contact critical residues delineated by X-ray) were performed by site-specific mutagenesis (SDM). His-purified recombinant products were assessed by immunoblotting on polyclonal anti-human IgE (Bethyl), and rabbit and goat anti-murine 26.82 IgE in the lab.

Summary of Discovery and Embodiment of Super b-Strands Flanking the Antigenic Loop Sequences Through the above numerous designs, recombinant expression, batch purification and extensive testing according to native and denaturing conditions, the embodiment of the super-b-strands of as the minimal, truncated FG microdomain enables vaccine candidates for all four IgE high affinities receptor-contacting core C2-3, BC, DE, and FG loops as neutralizing IgE B-cell epitopes. During initial selection among the four microdomain candidates, we determine and discover that native b-strands flanking the FG loop are the most robust b-strands, hence the 'super'-b strands, compared to the other three microdomains that support each of the respective antigenic core loop sequences. FG microdomain contains the robust 5' flanking b-strand, followed by HP rigid proline kink, the native FG core loop sequence, and the robust 3' flanking b-strand.

The embodiment of super b-strands for enabling native expression of native antigenic loops is materialized by the step-wise experimental discovery. (i) Importantly, the full length FG microdomain cloned at the N- or C-terminus of GFP enabled positive albeit weak expression of native FG core loop epitopes, while other microdomains did not yield native IgE neutralizing epitopes. (ii) Critically the removal of the N-terminal five amino acids revealed high antigenicity of the FG loop, and (iii) truncation of N-terminal ten amino acids of the 5' FG b-strand secondary structure enabled a stronger antigenic structure, indicating the importance of the optimal truncation and exhibition of the flanking super b-strands. (iv) The proline kink immediately following the 5' b-strands provides additional flanking support for the core FG loop B-cell epitope, as the truncation of N-terminal 15 amino acids also maintained the native FG loop antigenicity. (v) Additional primary sequences, C-terminal to the 3' flanking b-strand flanking are necessary to support the native FG loop, indicating the essential C-terminal amino acids for the super b-strands.

Thus in the embodiment of this invention, the super-b-strands comprise and are not limited to the N-5, N-10 and N-15 truncation from the 5' end of FG microdomain, the 5' super b-stand, proline kink, 3' super b-strand, and the further distal 3' non-truncated primary sequences. The flanking b-strands of the truncated FG microdomain serve as the universal scaffolding clamp for FceRI-contacting core loop sequences of the C2-3L, BC and DE microdomains, or other B-cell epitopes recombinantly cloned into the highly thermostable GFP protein scaffold.

To test long-term safety of the vaccine in rodents, it is necessary to construct a corresponding set of surrogate rodent vaccines. Thus the corresponding homologous rodent sequences: C2-3L (EPRGVI) (SEQ ID: 129), BC (DLAE) (SEQ ID: 130), DE (NNATL) (SEQ ID: 131), and FG (DFPK) (SEQ ID: 132) loops for this purpose can be swapped into the human super-b-strands that flank the native human FG Loop with the native human HLPR sequence replaced as shown in FIG. 8. The recombinant products can be detected under native gel running and detection condition by rabbit anti-26.82 rodent IgE or commercially available neutralizing anti-rodent IgE.

Protein Scaffold

Choice of a thermostable protein scaffold serves as an embodiment of this invention. GFP is known the most thermostable protein with $T_m$ at 82.6° C. among all known calyx-shaped, β-barrel bearing proteins, including lipocalins. At this temperature, the decimal reduction time is as long as 64 min for quenching 90% of the native fluorescence signal. In contrast, the melting temperature of lipocalins ranges from 44 to 54° C. with natural phosphotidylethanolamine-binding lipocalin (PEBP, $T_m$=54° C.), fluorescein-binding lipocalin ($T_m$=44° C.). The engineering step apparently lowers the Tm by 10° C. via distortion of native conformation due to insertion or replacement of sequences. Although the topological similarity of β-can is shared among the lipocalins and GFP, GFP is far more thermostable than lipocalins by as much as 38° C. (Skerra, 2000, BBA, 1482:337; Skerra, 2000, J. Mol. Reg. 13: 167). Therefore, GFP poses an advantage in contrast to lipocalins since the substitution native loops with random aptameric sequences may render the protein scaffold of GFP more heat-labile.

Collectively, the robust protein folding is a prerequisite for constraining the inserted B-cell loop epitopes in the super b-strands. Deletion of the native loop sequence without replacement with other loop sequences can cause collapse of the GFP protein scaffold with the loss of fluorescence detection. Robust folding of the protein scaffold plays a critical role in retention of the native B-cell epitopes of the inserted loops. Thus in the embodiment of this invention, fluorescence intensity, and positive immune reactivities to GFP under native conditions serve as predictor and correlate with the native immunoreactivity of the swapped B-cell epitopes in the super b-strands recombinantly expressed onto GFP.

GFP is also favorably compared to another thermostable protein scaffold, fibronectin FN3 ($T_m$=78° C.). The VEGF-binding, engineered FN3 moieties showed the depressed Tm ranging from 50 to 65° C., reflecting lower stability by a magnitude as much as 28° C. due to engineering. Thus the choice of GFP of a Tm of GFP<82.6° C. may poise as a more robust protein scaffold in contrast to FN3 in addition to being a biosensor. In this context, even with a 20° C. drop in Tm compared to the native GFP, aptameric GFP may still be favorably compared with single domain, camelid VHH exhibiting a $T_m$ around 64° C. (Skerra, 2000, BBA, 1482:337; Skerra, 2000, J. Mol. Reg. 13: 167).

Thus one aspect of the embodiment of the invention resides in inclusion different protein scaffolds, comprising and are not limited to GFP, immunoglobulin, camelid VHH, fibronectin, and lipocalin. Protein scaffolds with different melting temperature in thermostability can be compared and employed to accommodate the amino acid sequences of the insert.

Immunogenicity of FG Loop with Indigenous b-Strands Integrated and Co-Fold with GFP Protein Scaffold Immunogenicity of FG loop with endogenous b-strands co-folding with GFP: C57BL/6 mice were immunized with 10 μg FG (N-10)-GFP, and the swapped C2-3L, BC, DE (N-10)-GFP constrained in the super b-strands of the FG loop on GFP scaffold in alum sc, boosted twice. Immunoreactivities of antisera with native form of human IgE were ascertained by its reactivities with the native IgE at 1,000 to 100,000 fold dilutions by ELISA (plate coated with IgE, followed by antisera of different dilutions, and rat-anti-mouse kappa). And the immune sera frequently exhibited (OD reading 2 fold above background) diluted at 8,000 to 32,000.

Concomitantly, an IgE neutralizing assay is performed: Recombinant FceRIa D2/D1 subunit devoid of signal and membrane anchored sequences of the FceRI holoreceptor ($\alpha\beta\gamma_2$) was prepared, expressed with His-tag and affinity purified via IMAC column. IgE standard can be measured by IgE capture with his-tagged receptors adsorbed to Ni-treated 96-well plates. FIG. 9A showed IgE BED was captured by the plate-bound receptors. FIG. 4B showed that sera from FG-10-GFP, immunized mice abrogated IgE binding to receptors at 1:5,000 dilutions. (cpd, 50 ng/ml control at 1.2 OD), indicating that the neutralizing antibodies is present at 25 μg/ml, and is capable of abrogating serum circulating IgE about 1000 IU/ml.

Example 2

FG Loop can be Further Constrained in a Shorter and Redesigned Cystine Knots (CK) Miniprotein, Min-19 Construct

*Ecballium elaterium* trypsin inhibitor II (EETI-II) (SEQ ID: 47, SEQ ID: 48) with 28 amino acids from the squash family was the first discovered CK knot miniprotein (37). EETI-II has a triple anti-parallel β-sheet of consisting of three b-strands, knotted within with three cystine disulfide knots (forming the respective cysteine 1/4, 2/5, and 3/6 pair) (Gracy, 2008, N. A. R., 36: suppl 1:314). The folding requirement for all three cystine pairs to form in the oxidized environment poses stringent conditions for the native triple stranded b-sheets to additionally constrain/conform the molecularly grafted foreign B-cell epitopes or those flanked by the super b-strands.

An embodiment of this invention is to reduce the complexity by eliminating one cystine bridge. An evolutionarily conserved cystine knot motif, distributed throughout mammalian proteins, includes only two disulfide bridges constraining the β-hairpin loop structures. Min-23, deleted of one cystine pair, exhibits a well-defined conformation, similar to the structure of the native parent inhibitor EETI II in folding. Min-23 (SEQ ID: 45, SEQ ID: 46) is thermostable, folded with the cystine bridges supported by the C2-05 (residue 9/21) and the C3-C6 (residue 15/27) (Heitz, 1999, Biochem, 38: 10615).

The integrity of endogenous triple b-stranded, b-sheets of Min-23 is deemed to play a constraining role on the peptide conformation of the loop. Loop 1, 2, 3 and Loop 5 can be considered for replacement of IgE B-cell epitopes, and loop 5 in cystine-knotted peptides is endowed with longer amino acid sequences, and can be considered for accommodating longer peptide sequences.

Insertion of foreign sequence directly between the native loop 5' sequence has been performed between proline (P) and asparagine (N) (Souriau, 2005, Biochem, 44: 7143). The direct insertion of foreign sequences with native undeleted sequences combined can lead to distortion of the inserted sequences without the necessary beta-sheet in the grafted sequence. On the other hand, the insertion of foreign sequences into the complete loop 5 deleted sequences can also affect the formation of the necessary beta sheet of the inserted sequences.

To strengthen the constraining the capacity of loop 5, Min-23 is modified into Min-19 (SEQ ID: 43, SEQ ID: 44) or Min-18 (SEQ ID: 41, SEQ ID: 42): An embodiment of this invention resides in preserving the b-sheet structure of the foreign inserted sequence in the modified deleted loop 5 with retained hydrophobic phenylalanine, while the inserted structure also possess its own super b-strands. Min-19 and Min-18 are equipped with the indigenous and acquired b-strands supported by the double cystine bridges that offer the additional rigidity and constraining capacity for inserted foreign peptides with cystine-stabilized b-sheet (CSB).

In the overall embodiment of this invention, we choose to insert the endogenous b-strands scaffolded FG loop with the accompanying super b-strands into the C-FC (Cys-PheCys) position of Min-23 without perturbing the indigenous b-strands in the stable two disulfide bonded cystine knots.

Min-23 retains also high thermal stability, with a mean $T_m$ of 100° C., folded with the cystine bridges supported by the C2-05 (residues 9/21) and the C3-C6 (residues 15/27). The molecular construct proceeds as follows: (i) Site-directed mutagenesis (SDM) was conducted to eliminate the first five residues of trypsin inhibitor sequences, including the first cysteine (at position 2) from the EETI-II-GFP construct (16, 18), while maintaining the first b-strand starting at residue Met (at position 7). (ii) The subsequent SDMs were performed to render cysteine 19 serine 19 in order to deplete the cystine 1→4 bridge, and also to retain the residue 21, phenylalanine (F). (iii) Foreign loop sequences were inserted by SDM by primer extension.

Figure 10:
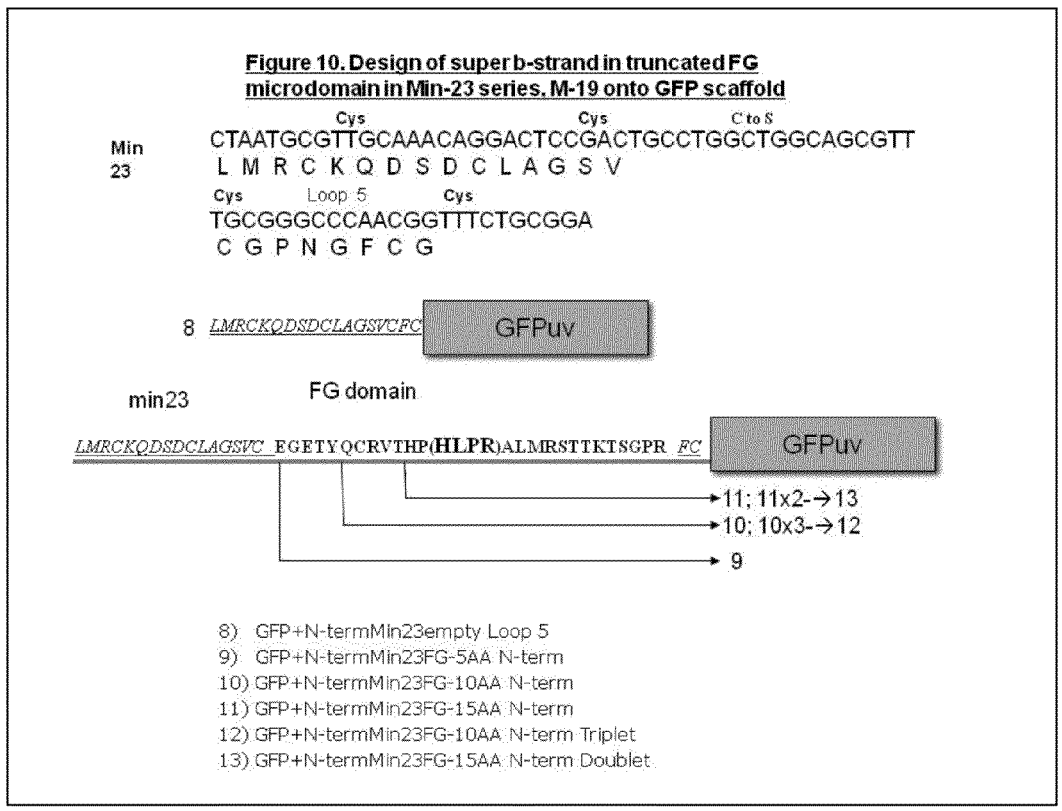
FIG. 10 depicts design of super b-strands in truncated FG microdomain in Min-23 series, M-19 onto GFP scaffold. The Diagram depicts the sequence of Min-23, and Min-18 prepared from EETI-II GFP template, and the design of the various truncated FG super b-strands and bidentate, tridentate constructs with amino acid residue designation of the truncated length. 1) Min23 (SEQ ID: 45, SEQ ID: 46); 2) Min19 (SEQ ID: 43, SEQ ID: 44); 3) Min18+gly (SEQ ID: 43, SEQ ID: 44) +glygly; 4) Min19+glygly; 5) Min23 FG (SEQ ID: 244, SEQ ID: 247); 6) glyglygly linker; 7) FG (SEQ ID: 9, SEQ ID: 10); 8) Min23empty Loop 5' (Min 19) (SEQ ID: 43, SEQ ID: 44); 9) GFP+Min23 FG-5AA N-term (SEQ ID: 250, SEQ ID: 251); 10) GFP+N-termMin23 FG-10AA N-term (SEQ ID: 245, SEQ ID: 248); 11) GFP+N-termMin23 FG-15AA N-term (SEQ ID: 246, SEQ ID: 249); 12) Min23 FG-10AA N-term (SEQ ID: 245, SEQ ID: 248) Triplet; 13) Min23FG-15AA N-term (SEQ ID: 246, SEQ ID: 249) Doublet.
Figure 11:
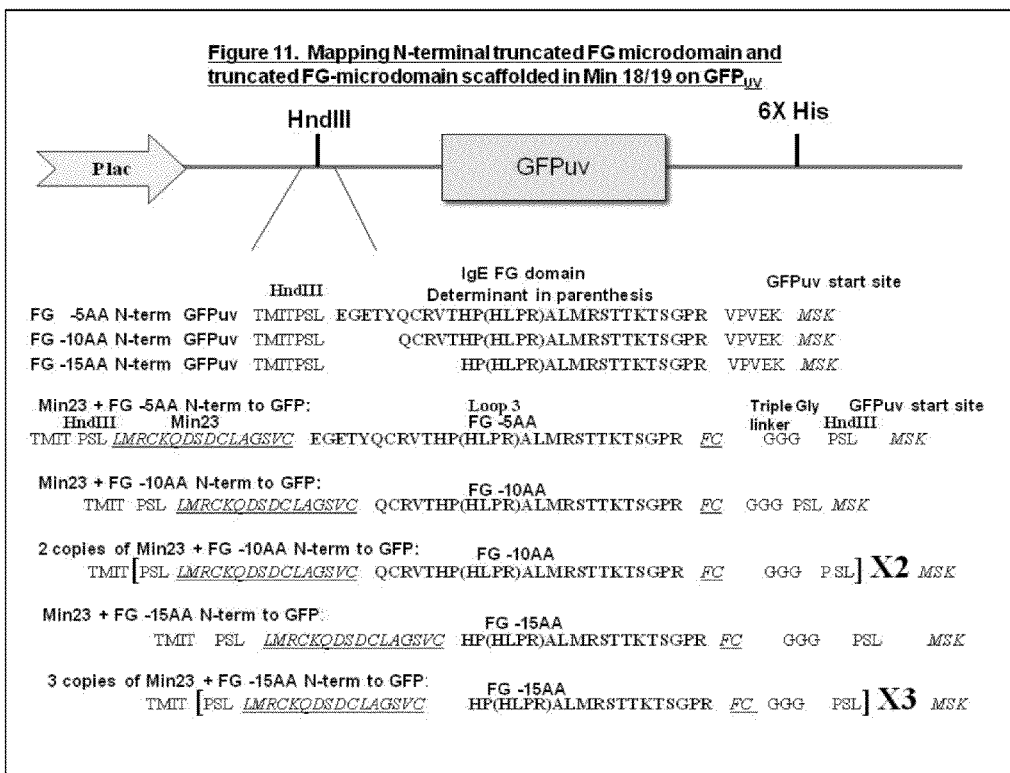
FIG. 11 depicts mapping N-terminal truncated FG microdomain and truncated FG-microdomain scaffolded in Min 18/19 on GFP$_{UV}$. N-terminal FG with different N-terminal truncations was prepared from the full length FG microdomain-GFP by deletion primer extension via SDM. FG-Min-23 series, i.e., Min-19 (onto GFP, counting the first glycine from the (gly)3 linker as the nineteen residue of the Min-23 series), was prepared by addition primer extension via SDM with the aforementioned FG-5, FG-10, and FG-15 into the Min-19 construct. PCR fragment of Min-23 (and other Min-23 series) was prepared from the EETI-II-GFP. Forward and reverse primers in were added in a PCR reaction with GFPuv-His EET1 wt as the template, inserted onto the HindIII site of the GFP$_{UV}$. Min-19 of the Min-23 series is further prepared with truncation of loop 5 into C-FC and ligated to the (gly)3 linker onto GFP. SDM was employed with primer extension to introduce the full length of FG microdomain into the Min-19. N-5, N-10 and N-15 primers were introduced by SDM and primer extension for truncating the FG domain mutants in Min-19. Bidentate and tridentate N-10 FG in Min-19 mutants were prepared by addition of PCR fragment of HindIII-digested FG-10 in Min-19 to HindIII digested GFP$_{UV}$. 1) Min18/19 FG-5AA (N-5 FG) (SEQ ID: 250, SEQ ID: 251); 2) Min18/19 FG-10 AA (N-10 FG) (SEQ ID: 245, SEQ ID: 248); 3) Min18/19 FG-15AA (N-15 FG) (SEQ ID: 246, SEQ ID: 249).

FIG. 10 showed the sequence of regular Min-23, and the Min-23 onto C-FC construct, and also the Min-19 construct with F left in loop 5 (CC) on GFP and the containment of truncated FG in single, duplicate and triplet repeats. FIG. 11 showed that HindIII site and the inclusive sequences of GFP vector, and the insertion of the FG microdomain in the Min-19.

As shown in FIG. 11, various truncated FG loops with the flanking b-strands, as well as cancatemers: FG (N-10x2; N-15 FGx3) were inserted between C-FC of Min-19 (SEQ ID: 43; SEQ ID 44), ranging from 19 to 57 amino acids, and these constructs with the terminal residues, FC of Min-23 were separated by (gly)3 spacer (the 5' glycine also can be regarded as the last and natural amino acid sequence from Min-23 (SEQ ID: 45; SEQ ID: 46), hence the construct of Min-19) onto the Hind III site of the GFP at the N-terminus with its His-tag added at the C-terminus of the GFP protein scaffold.

Figure 12:
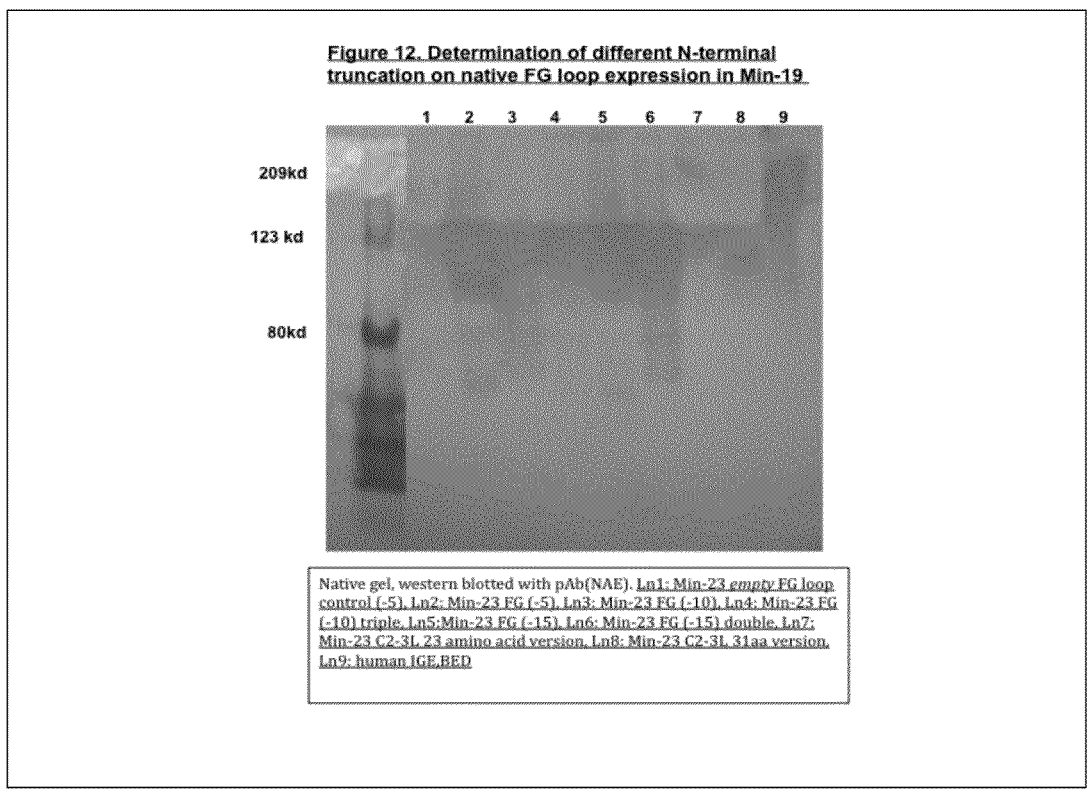
FIG. 12 depicts determination of different N-terminal truncation on native FG loop expression in Min-19. Selective recombinant products of the Min-23 series: Min-19 with inserted loop of various lengths with terminal His-6 tag were purified by IMAC beads, and examined on the native gel, and blot detected under non-denaturing conditions. 1) min23 empty FG loop (SEQ ID: 247); 2) Min 23N-5 FG (SEQ ID: 251); 3) min 23 N-10 FG (SEQ ID: 248); 4) min 23 N-10 FG (SEQ ID: 248) X3; 5) min 23 N-15 FG (SEQ ID: 249); 6) min 23 N-15 FG (SEQ ID: 249) X2; 7) min 23 C2-3 23C (SEQ ID: 267); 8) min 23 C2-3 31C (SEQ ID: 268); 9) human IgE (SEQ ID: 1).

As shown in FIG. 12, these constructs were expressed following IPTG induction, and purified by the IMAC column. FIG. 12 showed not only a single FG can be constrained in Min-23 empty loop 5 with glyglygly linker, i.e., Min19 (SEQ ID: 44) (lane 2, 3, 5 for N-5 FG, N-10 FG, and N-15 FG) but also a duplicate (bidentate, N-15 FG, lane 6), and a triplicate (tridentate, N-10 FG, lane 4) FG loops with variously trimmed flanking b-strands, can be accommodated with the Min-23 cystine knots, detected under native conditions by pAb anti-IgE as ~120 KDa tetramer. In contrast, the construct with the deleted FG core loop sequence was not detected by pAb (lane 1).

Figure 13A:
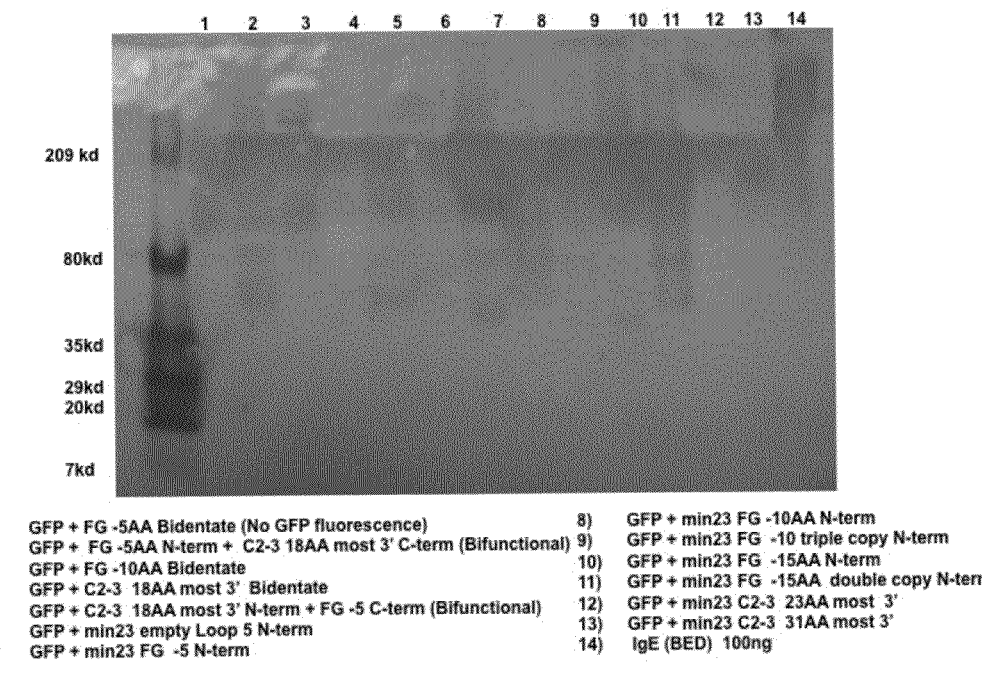
FIG. 13 depicts comparative native expression of homo- and hetero-(bifunctional) truncated FG and C2-3 construct. Panel A. Under native detecting conditions, affinity pure single FG with N-5, N-10 and N-15, and bidentate FG N-5, N-10 and N-15, tridentate FG N-15 versus truncated C2-3, and heterodentate, bifunctional truncated FG and C2-3 on N- and C-terminal of GFP were compared for native expression of IgE B-cell epitope by neutralizing anti-IgE. Panel B. The intensity of expression was scored from below detecting levels (0.0-0.2) up to a nominal assignment of four, i.e., that equivalent to native human IgE standard). 1) N-5 FG (SEQ ID: 12) X2; 2) N-5 FG (SEQ ID: 12) +C2-3 18C (SEQ ID: 269); 3) N-10 FG (SEQ ID: 14) X2; 4) C2-3 18C (SEQ ID: 269) X2; 5) C2-3 18C (SEQ ID: 269) +N-5 FG (SEQ ID: 12); 6) Min 23 empty Loop 5, i.e., min 19 (SEQ ID: 44); 7) min 23 N-5 FG (SEQ ID: 251); 8) min 23 FG-10 FG (SEQ ID: 248); 9) min 23 N-10 FG (SEQ ID: 248) X3; 10) min 23 N-15 FG (SEQ ID: 249); 11) min 23 N-15 FG (SEQ ID: 249) X2; 12) min 23 C2-3 23C (SEQ ID: 267); 13) min 23 C2-3 31C (SEQ ID: 268); 14) human IgE (SEQ ID: 1).

In contrast, FIG. 13A/13B showed diverse varieties of homo-bidentate versions, and hetero-bidentate, i.e., bifunctional versions of truncated FG and C2-3 microdomains in Min-19. Although FG N-5 single version of Min-19 preserved the native immunoreactivity (lane 7), the homo-bidentate lacked native immune reactivity, indicating a distortion of the native conformation via its duplicate presence of FG-N-5 in the Min-19 (lane 1). Since truncated C2-3 did not exhibit the native determinant (lane 12, 13 for the single and lane 4 for bidentate), the immune reactivity of bifunctional of C2-3 18AA, 3' and FG N-5 is due to the reactivity with FG N-5, and thus affirming the loss of reactivity in the bidentate FG N-5 was likely due to crowding and the distortion of native B-cell epitope.

Therefore, the retention of native immune reactivities of homo-bidentate N-10 FG (lane 3), and N-15 FG (lane 11) and the homo-tridentate N-10 FG (lane 9) indicated the robustness and the advantage of shorten version of the FG microdomain with regard to their insertion into the Min-19 in GFP protein scaffold.

In contrast to the robust FG loop presentation in the Min-19 construct, different versions of C2-3 exhibited weak expression of native immune reactivity to anti-neutralizing IgE as shown in FIG. 13, i.e., C2-3 18 from 3' bidentate (lane 4), or bifunctional from N- or C-terminal to FG N-5 (lane 2 and lane 5) and as single 23 from 3' (lane 12), and 31 from 3' (lane 13).

This detailed mapping indicates that (i) Min-19 version can cause presentation of IgE loop epitope already properly scaffolded by the super b-strands of FG microdomain, and (ii) the Min-19 accommodation leads to only moderate expression of the B-cell epitopes, C2-3 with no intrinsic scaffolding secondary structures; (iii) the retention of C2-3 core loop B-cell epitope can be materialized in swapping with the native FG loop core sequence in the super b-strands of FG microdomain in Min-19, supported by the observation in FIG. 7A.

FIG. 13 B summaries the observation in the histogram, which also indicates the critically important supporting role of the 3' amino acid sequence for the consolidating the super b-strands. The deletion of the seven amino acids strongly diminished the capacity of FG microdomain to preserve the native FG loop B-cell epitopes.

Therefore, the embodiment of the invention resides in integrating the super b-strands into loop 5 properly selected for endogenous loop deletion. It is important to note that M-19 can consistently maintain the conformation of the three variety of trimmed FG super b-stranded loop epitope to the same intensity of expression. Thus Min-19 GFP construct at the N-terminal of GFP reproduced the same pattern of conformation constraint without compromising the native epitope scaffolded by the preexisting scaffold.

Importance of Pre-existing Secondary Structure Constraint for the Loop Sequences The inventive process consists of empirically testing the feasibility of various configurations of EETI-II and Min-23 series in constraining loop B-cell epitope. Several modalities loop 5 insertion are included in the embodiment of this invention: (i) depending on the nature of B-cell epitope and the extent of truncation of the super b-strands, entire replacement of the native loop 5 with the new B-cell epitope may be implemented; (ii) the B-cell epitope can be inserted following the rigid proline (P) with N and G deleted, and neighboring the P, in utilizing the proline kink as a pivot for the foreign epitope.

(iii) The B-cell epitope can be inserted immediately prior to the hydrophobic phenylanaline residue in the truncated loop 5. The feasibility of each conformation relies on the nature of amino acid composition of the foreign sequences to be inserted. (iv) Min-23 was employed for accommodating sequences between P and N without the definition of secondary structures.

(v) Direct loop to loop swapping in that the B-cell loop sequence (without the flanking secondary structure) may be swapped with the indigenous sequence in the native loop of Min-19; (vi) in addition to accommodating the B-cell epitope in N-terminal end folding with GFP protein produced in the bacterial cytosol, folding and production in the oxidative periplasmic space constitutes another embodiment of this invention.

In the modality direct loop to loop swapping, and recombinant proteins expressed the presence of oxidative folding environment (v and vi), we herein demonstrated the critical role of super b-strands for the core IgE neutralizing epitopes: BC (VDLAPS) (SEQ ID: 110) and DE (QRNGTL) (SEQ ID: 123) loops as shown in loop swap into the super b-stands of FG microdomain (FIGS. 6 and 7). FIG. 14 showed the design and execution diagram of the direct loop swap between BC and DE loop sequences with loop sequences of the loop 1, 2, 3, 5 of the EETI-II in pMal that can be produced in the favorable oxidative periplasmic space.

Next, we evaluate whether the series of insertion mutants were recombined at the C-terminus of the maltose-binding protein (MBP) vector, and expressed in the more oxidative periplasmic microenvironment may improve the folding, and restore the native loop conformation of the grafted BC and DE core loop epitopes.

Figure 15:
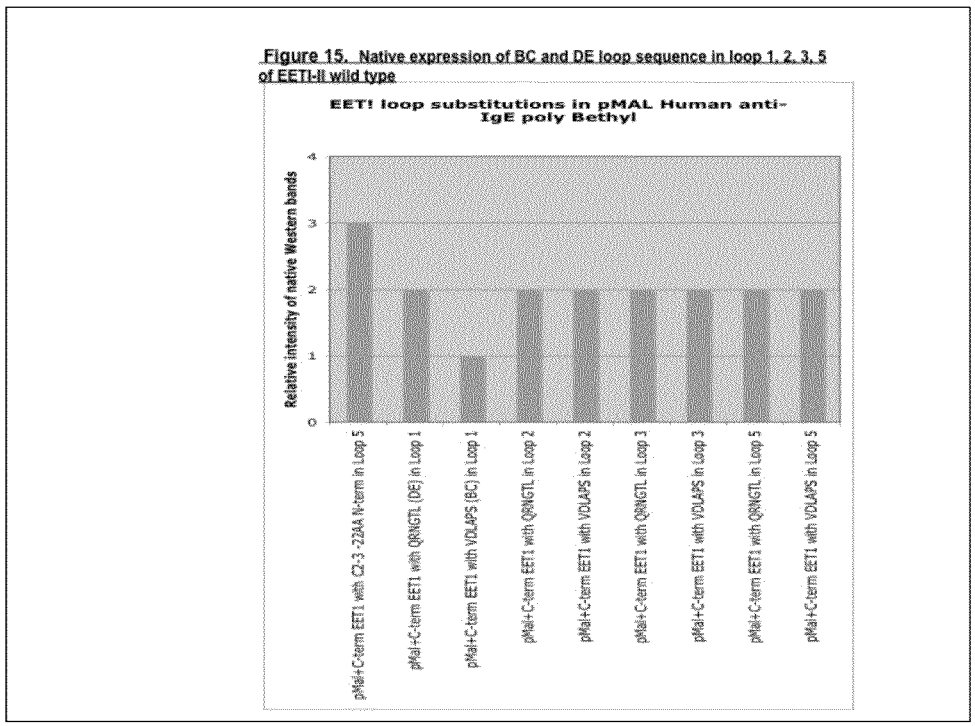
FIG. 15 depicts native expression of BC and DE loop sequence in loop 1, 2, 3, 5 of EETI-II wild type. To facilitate oxidative folding for the formation of triple cystine bridge, EETI-II with loop substitution was amplified by PCR with forward and reverse primers with GFPuv-His EET1 wt as the template. Forward primer started with gcggccgc of the Not 1 site and reverse primer with gaattc of the EcoRI site. PCR product was digested with Not1/EcoR1, and ligated to pMal 5pE that was digested with Not1 and EcoR1 on the C terminus of the maltose gene with the removal of the Gly-Gly-linker from pMal, and the fused PCR fragment was then cloned into Not1/EcoR1 pMal5pE. The series of recombinant EETI-II wild type loop substitute-pMal products were expressed in periplasmic space and purified by maltose column, and immune reactivities evaluated with neutralizing anti-IgE under native, non-denaturing conditions.

The yield of MBP protein was elevated; however as shown in FIG. 15, EETI-II with inserted BC and DE loops were weakly reactive with neutralizing anti-IgE under native conditions. Therefore, the embodiment of this invention attests to the sequence-dependent, direct loop to loop swap, i.e., native loop 1, 2, 3, 5 of the EETI-II with foreign loop sequences, and further indicates the requirement of loop sequences integrated into super b-strands prior to its replacement of the native loop of EETI-II The lack of direct loop swapping between the BC and DE loops and the native loop sequences of the EETI-II, substantiates the need for the main embodiment of the invention in (i) employing a truncated EETI-II with two cystine bridges to reduce the errors of knots formation of the existing cysteines; (ii) scaffolding the foreign loops preferably in super b-strands when further constrained in the double cystine knots. Hence, the embodiment of the invention resides in the two-step process of scaffolding the loop sequence within preexisting super b-strands, and of integrating the constrained loop into the optimized Min-23 series.

Figure 16:
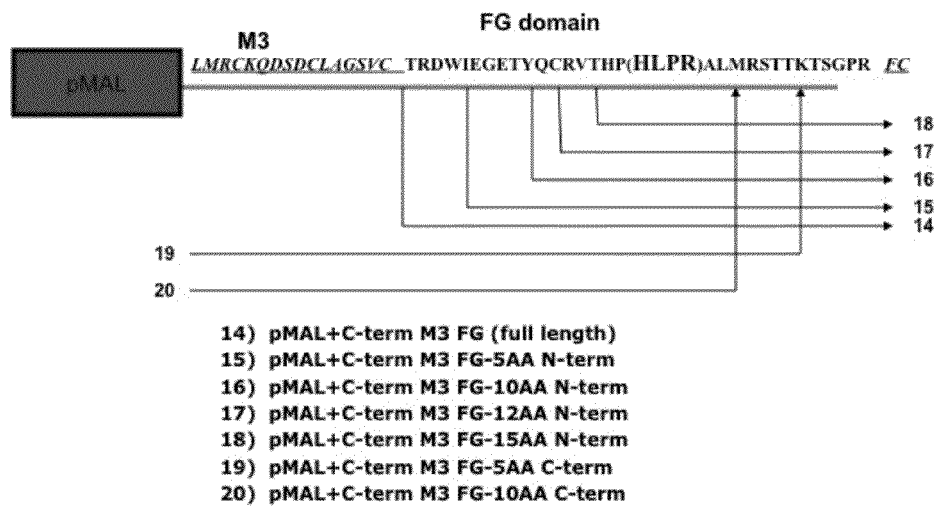
FIG. 16 depicts native expression of FG core loop in truncated FG microdomain scaffolded in Min-18 subject to oxidative folding. Min-18 of the Min-23 series was prepared as follows: Forward and reverse primers were added in a PCR reaction with GFPuv-His EET1 wt as the template with the synthesized product as: Gcggccgc (Not 1) CTAATGCGTTG-CAAACAGGACTCCGACTGCCTGGCTG-GCTGCGTTTGCGGGCCCA ACGGTTTCTGCGGA (Min-23) gaattc (EcoRI) (SEQ ID: 135). PCR product was digested with Not1/EcoR1, and ligated to pMAL 5pE (NEN), that was digested with Not1 and EcoR1 on the C terminus of the maltose gene with the removal of the Gly-Gly-linker from pMal, and the fused PCR fragment was then cloned into Not1/EcoR1 pMal5pE. Min-18 of the Min-23 series (M3) was then prepared by SDM with deletion primer of loop five of Min-23, retaining only the phenylalanine (F). Next to obtain the differentially truncated N- or C-mutants, overlapping primers with omission of different N-terminal sequence of FG microdomain were in SDM reaction Min-18-pMal, and the clone with the correct constructs were ascertained by DNA sequencing. M3 (Min-18) series: 14) pMal (SEQ ID: 49, SEQ ID: 50)+ C-term M3 FG full length (SEQ ID: 244, SEQ ID: 247); 15) M3 N-5 FG (SEQ ID: 250, SEQ ID: 251); 16) M3 N-10 FG (SEQ ID: 245, SEQ ID: 248); 17) M3 N-12 FG (SEQ ID: 271); 18) M3 N-15 FG (SEQ ID: 246, SEQ ID: 249); 19) M3 C-5 FG (SEQ ID: 272); 20) M3 C-10 FG (SEQ ID: 273).
Figure 17:
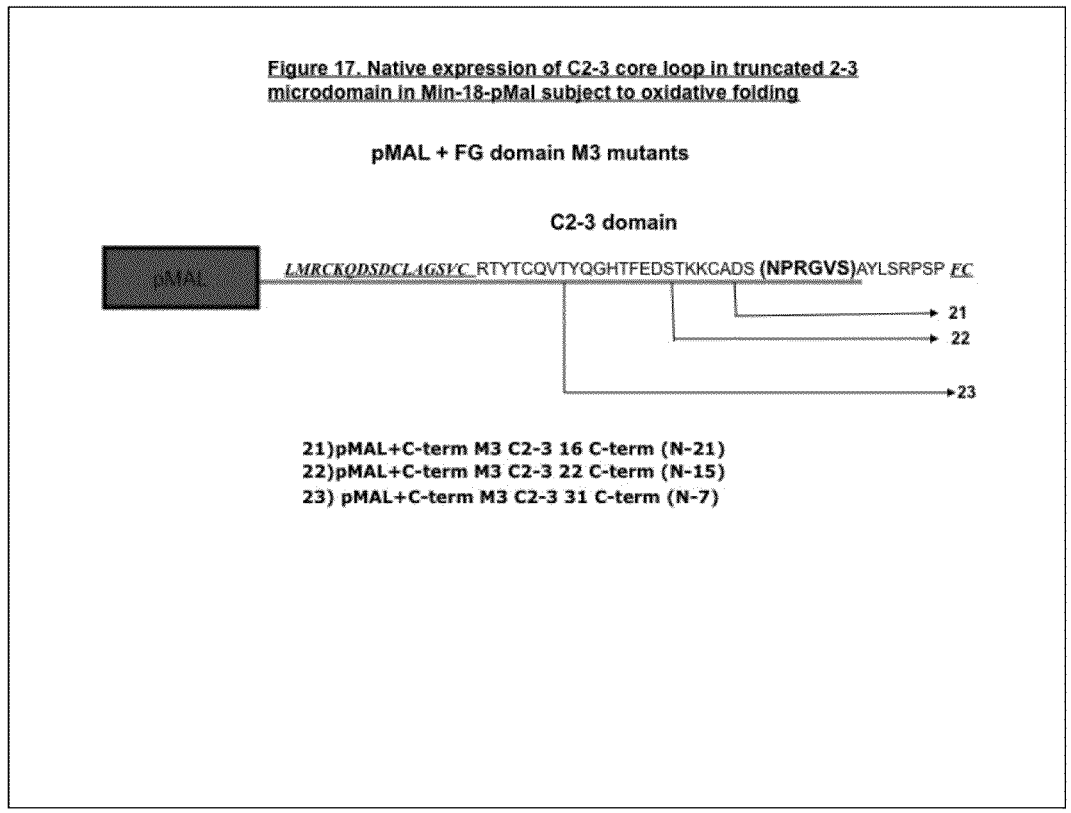
FIG. 17 depicts native expression of C2-3 core loop in truncated 2-3 microdomain in Min-18-pMal subject to oxidative folding. The procedure is similar to that described in legend of FIG. 16 with the SDM conducted with primer that prime that initialize with Min-18 sequence with omission of 5' sequence of C2-3 microdomain. 21) pMal (SEQ ID: 49, SEQ ID: 50)+ M3 16C (N-21) (SEQ ID: 259); 22) M3 C2-3 22C (N-15) (SEQ ID: 260); 23) M3 31C (N-7) (SEQ ID: 261).

Enablement of Strongly Augmented Expression of Super b-Stranded IgE B-Cell Epitope in Min-18 in pMbp in Oxidative Periplasmic Space Next we determine the role the oxidative microenvironment in augmenting yield and intensity of the native epitope pre-scaffolded by super b-strands in the Min-18 construct (when the terminal glycine is counted into the glyglygly linker, thus it is equivalent to Min-19 as Min-18/Min-19) in pMal in the optimal oxidative folding milieu. Min-18 with various N- and C-terminal FG deletions were presented in FIG. 16 executed Diagram and Min-18 with different lengths of C2-3 is presented in FIG. 17 executed Diagram.

Figure 18:
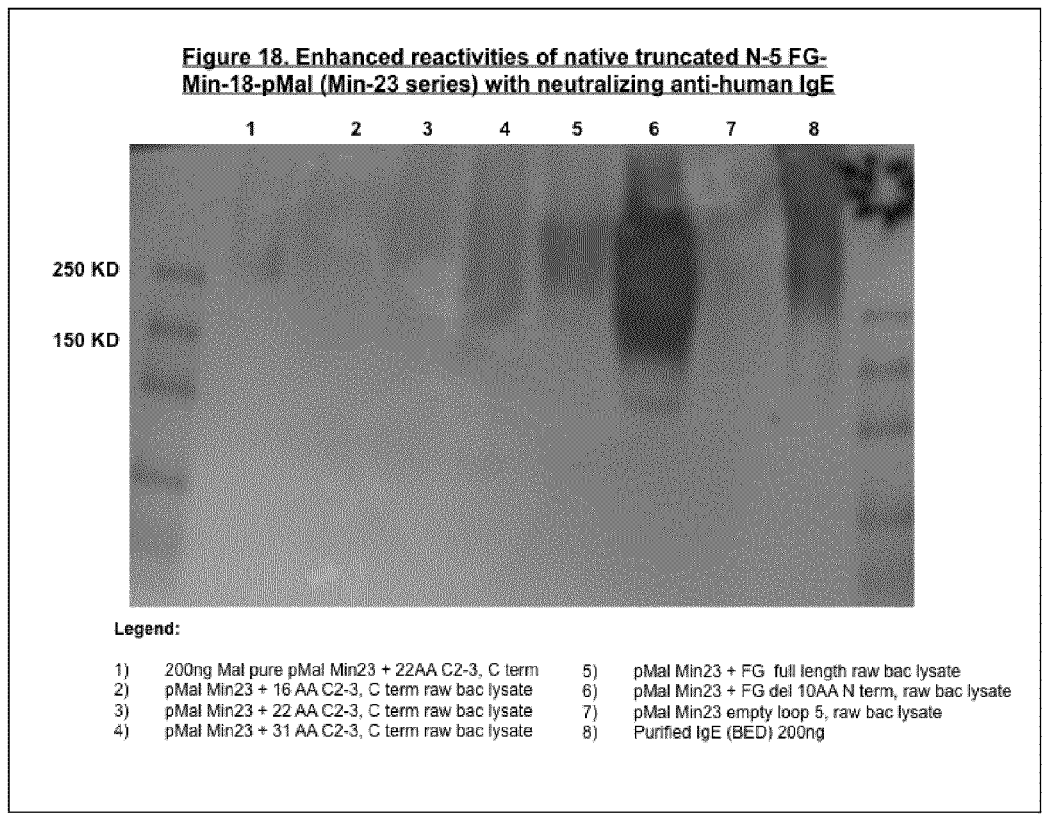
FIG. 18 depicts enhanced reactivities of native truncated N-5 FG-Min-18-pMal (Min-23 series) with neutralizing anti-human IgE. Truncated FG-N-5-Min-18-pMal was purified form periplasmic space via maltose column. 150 ng of the recombinant constructs of various deletions from the N- or C-terminus, including HLPR deleted constructed were detected under native conditions with neutralizing anti-IgE. The intensity of the expression was compared with an equivalent dose of human myeloma IgE (BED). Notably, the full length FG microdomain failed to express native FG loop, while the intensity of native loop HLPR (SEQ ID: 23) of one single B-cell epitope expressed in FG N-5 construct in the oxidative periplasmic space, exceeded that of myeloma human IgE containing all four IgE neutralizing B-cell epitopes. 1) pMal (SEQ ID: 50) Min23 (empty loop 5 without glyglygly linker, i.e., Min18) (SEQ ID: 42)+ 22 C22 C2-3 (SEQ ID: 260); 2) pMal M23 (empty loop 5)+ C16 C2-3 (SEQ ID: 259); 3) pMal M23 (empty loop 5)+ C22 C2-3

As shown in FIG. 18, Min-23 did serve this further augmentation for the FG epitope which was already stabilized by the super b-strands, and the IgE B-cell epitopes were strongly augmented in the oxidative periplasmic milieu, as observed in lane 2 of FG with 5 amino acid deletion at the N-terminus, and loss the reactivity for 15 amino acid deletion and 18 amino acid deletion from the N-terminus. The intensity of expression of the equivalent concentrations of maltose column affinity purified product exceeds that of even 150 ng of human IgE, exhibiting all IgE B-cell epitopes, including also four receptor-docking IgE B-cell epitope.

Figure 13B:
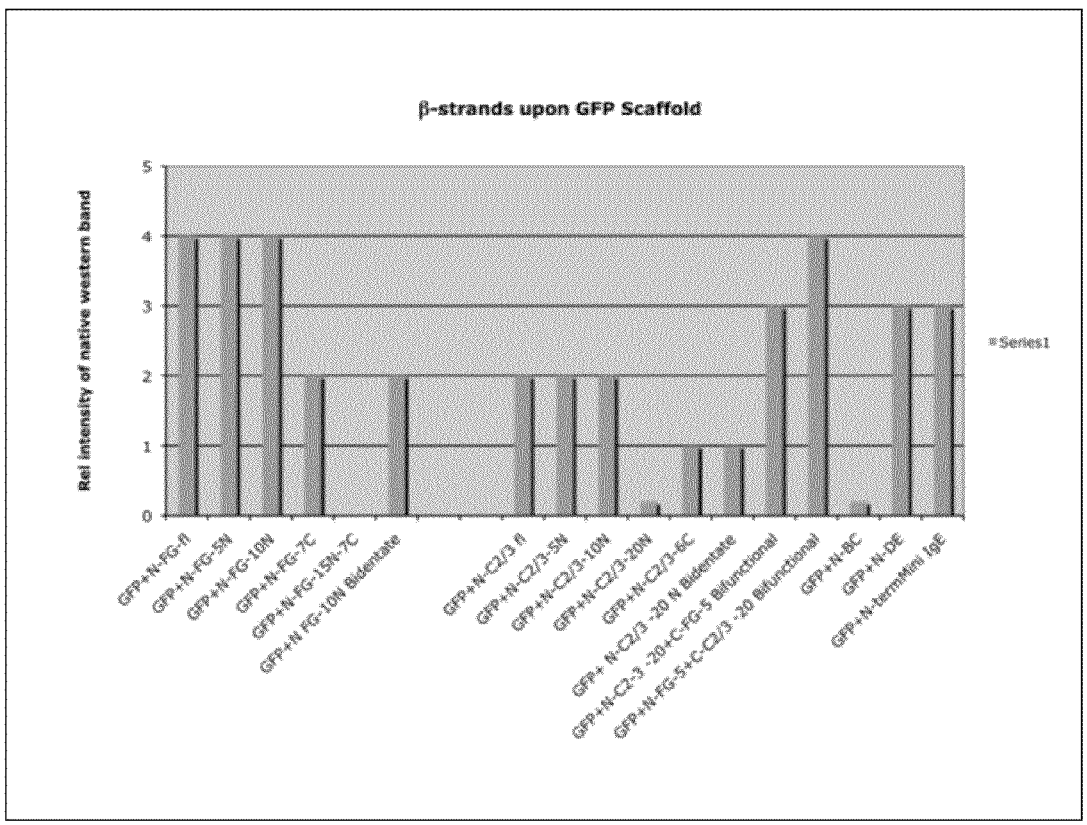

Further the FG segment with as few as three or five amino acid deletion from the C-terminus, 3, 5, 10 (lane 5, 6, and 7) materialized a detrimental effect on the native conformation of the FG epitopes. This further confirms that integrity of C-terminus of FG microdomain is indispensable as noted in also the FG-microdomain-pGFP construct (cpd. FIG. 13B).

As shown in FIG. 19, noticeably, in addition to the N-5 FG, Min-18 (without glyglygly linker) plays a robust role in further constraining and augmenting expression of the N-10 FG pMal construct in the periplasmic oxidative environment. The intensity of expression of even the recombinant products from the crude bacterial product also far exceeded that of even 200 ng of human IgE, which exhibited all IgE B-cell epitopes, including four receptor-docking IgE B-cell epitopes and other non-receptor-related B-cell epitopes from CHe1 to CHe4 domains. Thus the B-cell monospecific vaccine candidate dictates that a native single epitope in the embodiment of the invention be equivalent to or exceeds that of high concentrations of native molecules.

Hence, the steps materialize IgE B-cell N-minus ten amino acid truncated FG epitope can be a good IgE vaccine candidate. Thus the summary statement of one aspect of the embodiment of this invention is that intense robust expression of a super b-stranded scaffolded epitope can be augmented by Min-23 series, Min-18 as a second step of cystine-knotted scaffolding/framing and three dimensional protein folding, consummated in the Min23-pMal oxidative chemical folding milieu.

As shown in FIG. 20, the further constraint exerted by the double cystine bridges can enhance the scaffolding of even the weak secondary structure for the C-terminal 22 amino acids of the C2-3 microdomain. As shown in FIG. 20, denatured and native conformation, the effect of constraining C2-3 with cystine knots is effective.

One main embodiment of this invention was described as swapping the B-cell loop epitopes with native FG loop sequences of the super b-strands of the FG microdomain (FIGS. 6 and 7). Therefore in another embodiment of this invention, IgE B-cell vaccines can be materialized in a two-step process into Min-18 in pMal for augmented expression. In step 1, C2-3 core loop epitope, or BC core loop epitope, or DE core loop epitope can be swapped and replace the native loop sequences of super b-strands of the truncated FG microdomain. And in step 2, the antigenic loops scaffolded by the super b-strands can be further constrained by Min-18, expressed onto the protein scaffold that permits expression and oxidative folding.

In addition to IgE B-cell epitopes, another embodiment of this invention includes swapping the viral neutralizing epitopes of gp41, gp120 of human immunodeficiency virus (HIV) and hemagglutinin of influenza virus into the super b-strands of the truncated FG microdomain. Thus the embodiment of this invention for preparing general neutralizing vaccines for HIV, Flu virus are: (i) the discrete loop structure for viral amino acids delineated through its attachment to the host receptors will be cloned into the flanking super b-strands; (ii) the viral neutralizing epitope in the flanking super b-strands is inserted into the Min-23 loop 5 fused with pMal; (iii) the viral epitope within super b-strands pMal construct is expressed in the oxidative periplasmic space folding environment.

In summary, the embodiment of the invention for enabling specific IgE vaccine application is an integration of the four steps: (i) the step of validating the super b-strands is taken for conducting truncation of the N- and C-terminal amino acids;

this leads to the conclusion of critical N (N-5, and N-10) and C-terminus (C-0) in flanking the FG loop regions; (ii) the insertion of other critical IgE receptor contacting amino acid residues will be constructed, substituting the native FG loop; (iii) the Min-23 loop 5 insertion further strengthens and stabilizes the super b-strands constructs; (iv) the oxidative folding environment of MBP in the periplasmic space will provide the folding environment.

Example 3

Methods and Protocols for Super b-Strands, Min-23 and GFP Scaffold Constructs

Reagents employed are: Phusion® Flash High-Fidelity PCR Master Mix, restriction enzymes, and pMAL-p5E vector were purchased from New England Biolabs. Antibodies were from Abcam (goat anti-GFP antibodies, goat anti-human IgE antibodies, and HRP conjugated donkey polyclonal to Goat IgG), Clontech (Full-length GFP polyclonal antibodies), and Cell Signaling Technology (HRP conjugated anti-mouse IgG antibodies and HRP-conjugated anti-rabbit IgE antibodies). TMB Membrane Peroxidase Substrate System was ordered from KPL. Rapid DNA ligation kit was from Roche. DNA purification kits were purchased from QIAGEN. Ready Gels were from Bio-Rad. Immobilon-P Transfer Membrane was from Millipore. Vector pGFPuv was from Clontech.

PCR reaction: DNA template (1-10 ng) and primers (0.25 µM) are added to distilled water to a final volume of 25 µl. Equal volume of Phusion Flash PCR Master Mix is added and mixed. The PCR conditions are: denature at 98° C. for 1 second, annealing at 55° C. for 5 seconds, and extension at 72° C. for 15 second/1 kb. Run 25-30 cycles. After the cycles, the samples are extended for another 1 minute, and hold at 4° C.

Expression of recombinant proteins in E. coli: Selective colonies of IgE-GFP constructs were picked up and inoculated in 1 ml LB medium with appropriate antibiotics (ampicillin, chloramphenicol, or spectinomycin at 100 µg/ml, 25 µg/ml and 80 µg/ml, respectively). The cultures were grown at 37° C. for overnight. Next day, add 3 ml fresh LB medium with inducer (Isopropyl β-D-1-thiogalactopyranoside (IPTG) to 1 mM or chlorotetracycline (CTC) to 100 ng/ml) to the overnight culture, and grew the culture for another 1-4 hours to induce protein expression. Cells were harvested and washed with 1×PBS twice. Cell walls were degraded with lysozyme (1 mg/ml) in 1×PBS buffer for 15 minutes at room temperature. Then, the cells were sonicated on ice for three rounds, 10 seconds each at 50% power with 30 seconds intervals. After spin at 12,000 rpm for 10 minutes, the supernatant was transferred to a new tube for further analysis.

Protein electrophoresis, native or denaturing conditions: For native gel electrophoresis, cell lysates were mixed with equal volume 2× native sample buffer (0.125 M Tris-HCl, 5% glycerol, pH6.8) just prior to loading samples onto native gel. Proteins were separated with native running buffer (3.03 g Tris Base, 14.4 g Glycine, in 1000 ml distilled water). For denaturing conditions, samples were mixed with sodium dodecyl sulfate (SDS) Reducing buffer (final SDS and β-mercaptoethanol concentrations are 1%), and heated at 95° C. for 5 minutes before loading onto gels. The running buffer contains 1% SDS. After separation, proteins were transferred to PVDF membranes for immunoblotting.

Immunoblotting assay. PVDF membrane with transferred proteins was blocked with 5% dry milk in PBS for 1 hour. After washing three times with PBST (1×PBS with 0.05% Tween-20), the membrane was incubated with primary antibodies (1:1000 to 1:10,000 dilution according to vendor's instructions) for 1-16 hours. Wash the membrane three times with PBST and incubate with HRP conjugated second antibodies for 1 hour. After washing the membrane three times with PBST, TMB Membrane Peroxidase Substrate (enhancer: TMB peroxidase substrate: peroxidase substrate solution B=1:5:5) was added to cover the membrane. To stop the colorimetrical reaction, distilled water was added at the desired color.

Generation of EETI-II-IgE (8AA) Constructs

As EETI-II cDNA is only 84 nucleotides (28 amino acids), the EETI-II-IgE (8AA, "DSNPRGVS") constructs were generated by PCR of two synthesized primers. Restriction enzyme site (Hind III) and linker (between EETI-II and GFPuv) were added in the primers.

```
The primers for pEETI-L1-8AA (replacing EETI-II loop 1 with 8 C2-3 linker residues):
EETI-L1-8AA-F:
5'cgccaagcttggggtgcgattccaacccgagaggggtgagctgcaaacaggactccgactgcctggctggc-3' (SEQ ID: 141)

EETI-L1-8AA-R:
5'-tcataagcttcggatctcttaatccgcagaaaccgtttgggcccgcaaacgcagccagccaggcagtcggag-3' (SEQ ID: 142)

The primers for pEETI-L2-8AA (replacing EETI-II loop 2 with 8 C2-3 linker residues):
EETI-L2-8AA-F:
5'-cgccaagcttggggtgcccgcgaatcctaatgcgttgcgattccaacccgagaggggtgagctgcctggctgg-3' (SEQ ID: 143)

EETI-L2-8AA-R:
5'-tcataagcttcggatctcttaatccgcagaaaccgttgggcccgcaaacgcagccagccaggcagctcaccc-3' (SEQ ID: 144)

The primers for pEETI-L3-8AA (replacing EETI-II loop 3 with 8 C2-3 linker residues):
EETI-L3-8AA-F:
5'-cgccaagcttggggtgcccgcgaatcctaatgcgttgcaaacaggactccgactgcgattccaacccgagagggg-3' (SEQ ID: 145)

EETI-L3-8AA-R:
5'-tcataagcttcggatctcttaatccgcagaaaccgttgggcccgcaaacgcagctcacccctctcgggttggaatc-3' (SEQ ID: 146)

The primers for pEETI-L5-8AA (replacing EETI-II loop 5 with 8 C2-3 linker residues):
EETI-L5-8AA-F:
5'-cgccaagcttggggtgcccgcgaatcctaatgcgttgcaaacaggactccgactgcctggctggctgcgtttg-3' (SEQ ID: 147)

EETI-L5-8AA-R:
5'-tcataagcttcggatctcttaatccgcagctcacccctctcgggttggaatcgcaaacgcagccagccaggcag-3'. (SEQ ID: 148)
```

-continued

```
Primers used to substitute EETI-II loop 1:
EETI1 add QRNGTL sense:
caagcttggggtgcCAAAGAAACGGTACTCTTtgcaaacaggactc (SEQ ID: 149)

EETI1 add QRNGTL antisense:
gagtcctgtttgcaAAGAGTACCGTTTCTTTGgcaccccaagcttg (SEQ ID: 150)

EETI1 add VDLAPS sense:
caagcttggggtgcGTTGATCTTGCTCCATCTtgcaaacaggactc (SEQ ID: 151)

EETI1 add VDLAPS antisense:
gagtcctgtttgcaAGATGGAGCAAGATCAACgcaccccaagcttg (SEQ ID: 152)

Primers used to substitute EETI-II loop 2:
EETI-L2 add QRNGTL sense:
cctaatgcgttgcCAAAGAAACGGTACTCTTtgcctggctggctg (SEQ ID: 153)

EETI-L2 add QRNGTL antisense:
cagccagccaggcaAAGAGTACCGTTTCTTTGgcaacgcattagg (SEQ ID: 154)

EETI-L2 add VDLAPS sense:
cctaatgcgttgcGTTGATCTTGCTCCATCTtgcctggctggctg (SEQ ID: 155)

EETI-L2 add VDLAPS antisense:
cagccagccaggcaAGATGGAGCAAGATCAACgcaacgcattagg (SEQ ID: 156)

Primers used to substitute EETI-II loop 3:
EETI-L3 add QRNGTL sense:
ggactccgactgcCAAAGAAACGGTACTCTTtgcgtttgcgggc (SEQ ID: 157)

EETI-L3 add QRNGTL antisense:
gcccgcaaacgcaAAGAGTACCGTTTCTTTGgcagtcggagtcc (SEQ ID: 158)

EETI-L3 add VDLAPS sense:
ggactccgactgcGTTGATCTTGCTCCATCTtgcgtttgcgggc (SEQ ID: 159)

EETI-L3 add VDLAPS antisense:
gcccgcaaacgcaAGATGGAGCAAGATCAACgcagtcggagtcc (SEQ ID: 160)

Primers used to substitute EETI-II loop 5:
EETI-L5 add QRNGTL sense:
ctggctgcgtttgcCAAAGAAACGGTACTCTTtgcggaggaggacc (SEQ ID: 161)

EETI-L5 add QRNGTL antisense:
ggtcctcctccgcaAAGAGTACCGTTTCTTTGgcaaacgcagccag (SEQ ID: 162)

EETI-L5 add VDLAPS sense:
ctggctgcgtttgcGTTGATCTTGCTCCATCTtgcggaggaggacc (SEQ ID: 163)

EETI-L5 add VDLAPS antisense:
ggtcctcctccgcaAGATGGAGCAAGATCAACgcaaacgcagccag (SEQ ID: 164)
```

Site-Directed Mutagenesis (SDM):

Nucleotide can be substituted, added or deleted by site-directed mutagenesis. Synthesis primers contain the modified nucleotide(s). 1 µl of the forward primer at 125 ng/µl, and 1 µl of reverse primer at 125 ng/µl to 1 ul template at 50 ng/µl to 25 µl PCR master mix and 22 µl dd water in a total of 50 µl reaction. Take reaction and cycle as follows: 1) 98° C. for 10 sec; 2) 98° C. for 5 sec and 68° C. for 1 minute 15 sec/kb vector, repeat 18 cycles. After the cycles, the samples are extended at 68° C. for 10 min, and hold at 4° C. Dpn I (1 µl) is added to each PCR reaction, and incubated at 37° C. for one hour. Take 1 µl for transformation.

Construct of EETI-IgE peptide [QRNGTL (SEQ ID: 123), and VDLAPS (SEQ ID: 114)] into loop 1, 2, 3, 5 and fused to c-terminus of MBP: PCR products from EETI in GFPuv-His were used as template with modification by adding Not1 (5') and EcoR1 (3') ends with removal of Gly-Gly linker, and ligated into c-terminus of pMal5pE.

1) This forward primer (EETI-WT) works for all empty cassettes and all substitutions EXCEPT loop 1 delete and loop 1 substitutions: GATCgcggccgc (Not1)GGGtgc (L1 cys) CCGCGAATCCTA (SEQ ID: 165).

2) This reverse primer works for all empty cassettes and all substitutions EXCEPT loop 5 delete and loop 5 substitutions: GATCgaattc (EcoR1)tccgca (L5 cys) GAAACCGTTGGG (SEQ ID: 166).

3) This forward primer GATCgcggccgc (Not1)GGGtgc (L1 cys)CAAAGAAACGGT (SEQ ID: 167), will produce a product consisting of an EET1, Loop 1 substitute QRNGTL with Not1/EcoR1 ends.

4) This forward primer will amplify the product from the GFPuv-His EET1 Loop 1 substitute VDLAPS: GATCgcggccgc (Not1)GGGtgc (L1 cys)GTTGATCTTGCT (SEQ ID: 168).

5) This forward primer EETI: GATCgcggccgc (Not1)GGGtgctgc (L1 deletion)AAACAGGAC (SEQ ID: 169), will produce a product consisting of EET1 wt with a Loop 1 deletion and Not1/EcoR1 ends (Loop 1 EET1 empty cassette).

6) This reverse primer: GATCgaattc (EcoR1)tccgca (L5 cys) AAGAGTACCGTT (SEQ ID: 170), will produce a product consisting of EET1 with a Loop 5 substitution of QRNGTL with Not1/EcoR1 ends.

7) This reverse primer GATCgaattc (EcoR1)tccgca (L5cys) AGATGGAGCA (SEQ ID: 171), will produce a product consisting of EET1 with a Loop 5 substitution of VDLAPS with Not1'EcoR1 ends.

8) This reverse primer GATCgaattc (EcoR1)tccgca (L5cys) AGATGGAGCA (SEQ ID: 172), will produce a product consisting of EET1 with a Loop 5 deletion and Not1/EcoR1 ends.

Ligation reactions are as follow:
a). Primers 1 and 2+templates as follows: GFPuv-His wt; GFPuv-His deletion Loop 2; GFPuv-His deletion Loop 3; GFPuv-His substitution Loop 2 QRNGTL (SEQ ID: 123); GFPuv-His substitution Loop 2 VDLAPS (SEQ ID: 114); GFPuv-His substitution Loop 3 QRNGTL (SEQ ID: 123); GFPuv-His substitution Loop 3 VDLAPS (SEQ ID: 114).
b). Primers 2 and 5+template GFPuv-His Loop 1 deletion.
c). Primers 2 and 3+template GFPuv-His Loop 1 substitution of QRNGTL (SEQ ID: 123).
d) Primers 2 and 4+template GFPuv-His Loop 1 substitution of VDLAPS (SEQ ID: 114).
e) Primers 1 and 8+template GFPuv-His Loop 5 deletion.
f) Primers 1 and 6+template GFPuv-His Loop 5 substitution of QRNGTL (SEQ ID: 123)
g) Primers 1 and 7+template GFPuv-His Loop 5 substitution of VDLAPS (SEQ ID: 114).

Final constructs from the ligation reactions are:
1). pMal-p5e+EET1 wt;
2). pMal-p5e+EET1 del L1;
3). pMal-p5e+EET1 del L2;
4). pMal-p5e+EET1 del L3;
5). pMal-p5e+EET1 del L5;
6). pMal-p5e+EET1 sub QRNGTL (SEQ ID: 114) Loop 1;
7). pMal-p5e+EET1 sub QRNGTL (SEQ ID: 114) Loop 2;
8). pMal-p5e+EET1 sub QRNGTL (SEQ ID: 114) Loop 3;
9). pMal-p5e+EET1 sub QRNGTL (SEQ ID: 114) Loop 5;
10). pMal-p5e+EET1 sub VDLAPS (SEQ ID: 123) Loop 1;
11). pMal-p5e+EET1 sub VDLAPS (SEQ ID: 123) Loop 2;
12). pMal-p5e+EET1 sub VDLAPS (SEQ ID: 123) Loop 3;
13). pMal-p5e+EET1 sub VDLAPS (SEQ ID: 123) Loop 5

Construct of Min-23

Min23 is constructed by PCR reaction with template: GFPuv-His EET1 wt with deleted loop 5, and forward primer: GATCgcggccgc (Not1)TTGCAAACAGGAC (SEQ ID: 173); and the reverse primer: GATCgaattc (EcoR1)TCCgcagca (delete loop 5) AACGCAGCCAGCC (SEQ ID: 174). The PCR fragment was then digested with Not1 and EcoR1 and ligated into c terminus of pMalp5E vector cut with Not1/EcoR1 with the following sequence:

```
CTAATGCGTTGCAAACAGGACTCCGACTGCCTGGCTGGCTGCG TT
tgctgcGGA (SEQ ID: 175)
```

Construct of MBP fused Min-23 (with deleted loop 5) or Min-18 construct: EETI-GFPuv-His with deleted loop 5 was used as template for PCR. The two primers are: forward primer-Not I (5'-GATCgcggccgcCTAATGCGTTGCAAA-CAGGAC-3') (SEQ ID: 176) and reverse primer-EcoRI (5'-GATCgaattcTCCgcagcaAACGCAGCCAGCC-3') (SEQ ID: 177). The PCR product was digested with NotI and EcoRI and cloned into pMAL-p5E vector between NotI and EcoRI sites. MBP and EETI-II will be expressed as a fusion protein.

Construct of 16 amino acids of FG IgE peptide addition to loop 5 of Min23 with three constituents: Overall strategy is to use forward and reverse primer in a site directed mutagenesis reaction with pMal-p5e EET1-Min23 delete Loop 5 as a template. Thus Min23 template with deleted loop 5 and with the Not1 and EcoR1 at the two flanking sites is as follows: Gcggccgc (Not1)CTAATGCGTTGCAAACAGGACTCCGACTGCCTGGCTGGCT GCGTTtgc (with loop 5 deleted, between two cys tgc) tgcGGAgaattc (EcoR1) (SEQ ID: 178).

Forward 23 min 16AA SDM primer:

ggctgcgtttgcGATTCCAACCCGAGAGGGGTGAGCGCCTACCTAAGCCGG CCCAGCCCG tgcGGAgaattc (SEQ ID: 179), which is designed according to the three constituents: (i) 5' flanking region to EETI Loop 5: ggctgcgtttgc (SEQ ID: 277); (ii) 16 AA IgE domain insert into L-5:

```
 D   S   N   P   R   G   V   S   A   Y   L   S
GAT TCC AAC CCG AGA GGG GTG AGC GCC TAC CTA AGC

R   P   S   P       C (SEQ ID: 180)
CGG CCC AGC CCG; (iii) tgcGGAgaattc (EcoR1) (SEQ ID: 181).
```

Reverse 23 min 16AA SDM primer is as follows: gaattctccgcaCGGGCTGGGCCGGCTTAGGTAGGCGCTCACCCCTCTCGGGTT GGAATCgcaAACGCAGCC (SEQ ID: 182), designed according to three constituents (i) EcoR1 3'most EET1, Gaattctccgca (cysteine); (ii)16 AA IgE domain (Rev) insert into L-5:

```
 P   S   P   R   S   L   Y   A   S   V   G   R
CGG GCT GGG CCG GCT TAG GTA GGC GCT CAC CCC TCT

P   N   S   D       C (SEQ ID: 183)
CGG GTT GGA ATC; (iii) gca (cysteine) AACGCAGCC (SEQ ID: 184)
```

Construct of truncated FG in pGFP or Min-23-pGFP: Alternatively, forward and reverse primers with HindIII at the 5' and 3' with end with various triplet deletions were added to mini-IgE pGFP, and micro-IgE domain (pFG-GFPuv) for PCR reactions, and the products were digested with HindIII and ligated with HindIII digested GFPuv with C-terminal six histamine for IMAC column purification. To have further secondary cystine bridge constraint built in, N-5, N-10, and N-15 oligos Forward primers are designed with starting 5' deletion or N-deletion of five, ten or fifteen triplets (N-5, N-10, N-15), or with reverse primers of 3' deletion or C-deletion of 7 triplets (C-7). To place the various truncated FG versions into Min-19 cystine knot, site-directed mutagenesis forward primers with 5' flanking region to EETI Loop 5: ggctgcgtttgc (SEQ ID: 185), followed by triplets of N-5, N-10, and N-15 were added to Min-23-pGFP, and reverse primer, starting gca (cysteine) AACGCAGCC (SEQ ID: 186).

To prepare bidentate or tridentate structure of the truncated FG/Min-23-pGFP, PCR fragments were prepared from the 5' to 3' HindIII sites of the first generation of monomeric truncated FG-Min 23-pGFP construct, the PCR fragment was purified and digested with HindIII and ligated to the first generation of monomeric truncated FG-Min 23-GFP vectors. DNA sequences were performed and the length of the concatemer evaluated, and bidentate or tridentate configuration was then determined.

Construct Mini- and Micro-IgE: The mini-IgE fragments were amplified from human IgE heave chain cDNA constructed in the laboratory. The primers used for PCR are: IgE C2-3-F(Hind III) (5'-GATCAAGCTTGcgcacctacacctgc-caggtc-3') (SEQ ID: 187) and IgE FG-loop-R (AgeI) (5'-GATCACCGGTACacgcgggccgctggtcttgg-3') (SEQ ID: 188). PCR product was digested with Hind III and AgeI and cloned into pGFPuv between Hind III and AgeI. The micro-IgE constructs were generated by site-directed mutagenesis. The primers used were:

```
Delete BC, DE, and FG loops (pC2-3-GFPuv):
del(BCDEFG): 5'-ccggcccagcccggtaccggtagaaa-3' (SEQ ID: 189);

del(BCDEFG)-antisense: 5'-tttctaccggtaccgggctgggccgg-3' (SEQ ID: 190);

Delete C2-3 linker (pBCDEFG-GFPuv):
del(C2-3 linker): 5'-tgattacgccaagcttgttcgacctgttcatccg-3' (SEQ ID: 191);

del(C2-3 linker)-antisense: 5'-cggatgaacaggtcgaacaagcttggcgtaatca-3'; (SEQ ID: 192)

Delete C2-3 linker and BC loop (pDEFG-GFPuv):
del(C2-3 + BC): 5'-gattacgccaagcttggtgaaccactccacca-3' (SEQ ID: 193);

del(C2-3 + BC)-antisense: 5'-tggtggagtggttcaccaagcttggcgtaatc-3' (SEQ ID: 194)

Delete C2-3 linker, BC loop and DE loop (pFG-GFPuv):
del(C2-3BCDE): 5'-gattacgccaagcttgacccgagactggatcg-3' (SEQ ID: 195);

del(C2-3BCDE)-antisense: 5'-cgatccagtctcgggtcaagcttggcgtaatc-3' (SEQ ID: 196).
```

Example 4

Illustrative Word Diagram

Part I:
SDM/Primer Extension for Deletion of EETI Cystine Knot Loops 1, 2, 3, and 5

Take pGFPuv-HIS EETI wt (N-terminal) construct and make primers for site directed mutagenesis (SDM, primer extension):

1. Loop 1 deletion using site directed mutagenesis:

```
End Lac
Start           HindIII EET1 WT    loop 1
ATGACCATGATTACGCCAAGCTTGGGGtgcCCGCGAATCCTAATGCGTtgc loop 2          loop 3              loop 5
AAACAGGACTCCGACtgcCTGGCTGGCtgcGTTtgcGGGCCCAACGGTTTCtgc Gly Gly   HindIII GFPuv
GGAGGAGGACCAAGCTTGATGAGTAAAGGAGAA (SEQ ID: 197)

Delete Loop 1 of EETI
End Lac
Start           HindIII EETI C     delete Loop 1 C
ATGACCATGATTACGCCAAGCTTGGGGtgcCCGCGAATCCTAATGCGTtgcAAACAGGACTCC

GACTGCCTGGCTGGCTGCGTTTGCGGGCCCAACGGTTTCTG

Gly Gly   HindIII GFPuv
CGGAGGAGGACCAAGCTTGATGAGTAAAGGAGAA (SEQ ID: 198)

Primers to delete Loop 1:              C C
Del-loop1-sense    5'-ccaagcttggggtgctgcaaacaggactcc-3' (SEQ ID: 199)

Del-loop1-antisense 5'-ggagtcctgtttgcagcaccccaagcttgg-3' (SEQ ID: 200)
```

2. Loop 2 deletion using site directed mutagenesis:

```
Delete Loop 2
End Lac
Start           HindIII EETI WT
ATGACCATGATTACGCCAAGCTTGGGGTGCCCGCGAATCCTAATGCGTtgc
```

-continued

```
Delete Loop 2
AAACAGGACTCCGACtgcCTGGCTGGCTGCGTTTGCGGGCCCAACG

Gly Gly  HindIII GFPuv
GTTTCTGCGGAGGAGGACCAAGCTTGATGAGTAAAGGAGAA (SEQ ID: 201)

Primers to delete Loop 2:       C  C
Del-loop2-sense     5'-atcctaatgcgttgctgcctggctgg ctgc-3' (SEQ ID: 202)

Del-loop2-antisense 5'-gcagccagccaggcagcaacgcatta ggat-3' (SEQ ID: 203)
```

3. Loop 3 deletion using site directed mutagenesis:

```
Delete loop 3
End Lac
Start            HindIII EET1 WT
ATGACCATGATTACGCCAAGCTTGGGGTGCCCGCGAATCCTAATGCGTT Delete Loop 3
GCAAACAGGACTCCGACtgcCTGGCTGGCtgcGTTTGCGGGCCCAACGG Gly Gly  HindIII GFPuv
TTTCTGCGGAGGAGGACCAAGCTTGATGAGTAAAGGAGAA (SEQ ID: 204)

Primers to delete Loop 3:       C  C
Del-loop3-sense     5'-ggactccgactgctgcgtttgcggg c-3' (SEQ ID: 205)

Del-loop3-antisense 5'-gcccgcaaacgcagcagtcggagtc c-3' (SEQ ID: 206)
```

4. Loop 5 deletion using site directed mutagenesis:

```
Delete Loop 5 of EETI
End Lac
Start            HindIII EET1 WT
ATGACCATGATTACGCCAAGCTTGGGGTGCCCGCGAATCCTAATGCGTT Delete
GCAAACAGGACTCCGACTGCCTGGCTGGCTGCGTTtgcGGGCCCAACG Loop 5   Gly Gly HindIII GFPuv
GTTTCtgcGGAGGAGGACCAAGCTTGATGAGTAAAGGAGAA (SEQ ID: 207)

Primers to delete Loop 5:       C  C
Del-loop5-sense     5'-ggctggctgcgttgctgcggaggag gaccaag-3' (SEQ ID: 208)

Del-loop5-antisense 5'-cttggtcctcctccgcagcaaacgca gccagcc-3' (SEQ ID: 209)
```

Part II:
SDM/Primer Extension for Addition of IgE Core Loop C2-3. BC, DE Sequences into EETI Cystine Knot Loops 1, 2, 3, and 5 Deleted Mutants
1. Add QRNGTL (SEQ ID: 123) and VDLAPS (SEQ ID: 114) to GFPuv-His EETI (N term) Loop 1 deletion using site directed mutagenesis:

```
Primers needed to add QRNGTL (SEQ ID: 123) substitution in loop 1:
ETTI L1 add QRNGTL (SEQ ID: 123) sense
caagcttggggtgcCAAAGAAACGGTACTCTTtgcaaacaggactc (SEQ ID: 210)

ETTI L1 add QRNGTL (SEQ ID: 123) antisense
gagtcctgtttgcaAAGAGTACCGTTTCTTTGgcaccccaagcttg (SEQ ID: 211)
```

-continued

```
                                      deleted Loop 1
End Lac                             CCGCGAATCCTAATGCGT
Start           HindIII EETI add: Q  R  N  G  T  L
ATGACCATGATTACG CCAAGCTTGGGGtgc CAAAGAAACGGTACTCTT tgcAAACAGGACTC CGACTGCCTGGCTGGCTGCGTTTGCGGGCCCAACGGT Gly Gly  HindIII  GFPuv
TTCTGCGGAGGAGGACCAAGCTTGATGAGTAAAGGAGAA (SEQ ID: 212)
```

Primers needed to add VDLAPS (SEQ ID: 123) substitution in loop 1:

ETTI L1 add VDLAPS (SEQ ID: 123) sense
caagcttggggtgcGCTCCATCTAGATGGAGCtgcaaacaggactc (SEQ ID: 213)

ETTI L1 add VDLAPS (SEQ ID: 123) antisense
gagtcctgtttgcaAGATGGAGCAAGATCAACgcaccccaagcttg (SEQ ID: 214)

```
                                        deleted Loop 1
End Lac                               CCGCGAATCCTAATGCGT
Start          HindIII EETI add: V  D  L  A  P  S
ATGACCATGATTACGC CAAGCTTGGGGtgc GTTGATCTTGCTCCATCT tgcAAACAGGACTC CGACTGCCTGGCTGGCTGCGTTTGCGGGCCCAACGGT Gly Gly    HindIII GFPuv
TTCTGCGGAGGAGGACCAAGCTTGATGAGTAAAGGAGAA (SEQ ID: 215)
```

2. Add QRNGTL (SEQ ID: 123) and VDLAPS (SEQ ID: 114) to GFPuv-His (c term) construct with EETI Loop 2 deletion using site directed mutagenesis:

Primers needed to add QRNGTL (SEQ ID: 123) substitution in loop 2:
ETTI-L2 add QRNGTL (SEQ ID: 123) sense
cctaatgcgttgcCAAAGAAACGGTACTCTTtgcctggctggctg (SEQ ID: 216)

ETTI-L2 add QRNGTL (SEQ ID: 123) antisense
cagccagccaggcaAAGAGTACCGTTTCTTTGgcaacgcattagg (SEQ ID: 217)

```
End Lac
Start           HindIII EETI WT
ATGACCATGATTACGCCAAGCTTGGGGTGCCCGCGAAT CCTAATGCGT Delete Loop 2
     AAACAGGACTCCGAC add: Q  R  N  G  T  L (SEQ ID: 123)
tgcCAAAGAAACGGTACTCTTtgcCTGGCTGGCTG CGTTTGCGGGCCCAACGGTTTCTG Gly Gly HindIII GFPuv
CGGAGGAGGACCAAGCTTGATGAGTAAAGGAGAA (SEQ ID: 218)
```

Primers needed to add VDLAPS (SEQ ID: 123) substitution in loop 2:
ETTI-L2 add VDLAPS (SEQ ID: 123) sense
acctaatgcgttgcGTTGATCTTGCTCCATCTtgcctggctggctg (SEQ ID: 219)

ETTI-L2 add VDLAPS (SEQ ID: 123) antisense
cagccagccaggcaAGATGGAGCAAGATCAACgcaacgcattagg (SEQ ID: 220)

```
End Lac
Start           HindIII EETI WT
ATGACCATGATTACGCCAAGCTTGGGGTGCCCGCGAAT CCTAATGCGT Delete Loop 2
    AAACAGGACTCCGAC add: V D  L  A  P  S
tgcGTTGATCTTGCTCCATCTtgcCTGGCTGGCTG CGTTTGCGGGCCCAACGGTTTCTG Gly Gly HindIII GFPuv
CGGAGGAGGACCAAGCTTGATGAGTAAAGGAGAA (SEQ ID: 221)
```

3. Add QRNGTL (SEQ ID: 123) and VDLAPS (SEQ ID: 114) to GFPuv-His construct with EETI (N term) Loop 3 deletion using site directed mutagenesis:

End Lac
Start HindIII EET1 WT
ATGACCATGATTACGCCAAGCTTGGGGTGCCCGCGAATCCTAATGCGTTGCA

Delete Loop 3
CTGGCTGGC add: Q R N G T L
AACA**GGACTCCGACtgc*CAAAGAAACGGTACTCTT*tgcGTTTGCGGGC**CCA

Gly Gly HindIII GFPuv
ACGGTTTCTGCGGAGGAGGACCAAGCTTGATGAGTAAAGGAGAA (SEQ ID: 222)

Primers needed to add QRNGTL (SEQ ID: 123) substitution in loop 3:
ETTI-L3 add QRNGTL (SEQ ID: 123) sense
ggactccgac**tgc*CAAAGAAACGGTACTCTT*tgc**gtttgcgggc (SEQ ID: 223)

ETTI-L3 add QRNGTL (SEQ ID: 123) antisense
gcccgcaaac**gca*AAGAGTACCGTTTCTTTG*gca**gtcggagtcc (SEQ ID: 224)

End Lac
Start HindIII EET1 WT
ATGACCATGATTACGCCAAGCTTGGGGTGCCCGCGAATCCTAATGCGTTGCA

Delete Loop 3
CTGGCTGGC add: V D L A P S (SEQ ID: 114)
AACA**GGACTCCGACtgc*GTTGATCTTGCTCCATCT*tgcGTTTGCGGGC**CCAA

Gly Gly HindIII GFPuv
CGGTTTCTG CGGAGGAGGACCAAGCTTGATGAGTAAAGGAGAA (SEQ ID: 225)

Primers needed to add VDLAPS (SEQ ID: 114) substitution in loop 3:
ETTI-L3 add VDLAPS (SEQ ID: 114) sense
ggactccgac**tgc*GTTGATCTTGCTCCATCT*tgc**gtttgcgggc (SEQ ID: 226)

ETTI-L3 add VDLAPS (SEQ ID: 114) antisense
gcccgcaaac**gca*AGATGGAGCAAGATCAAC*gca**gtcggagtcc (SEQ ID: 227)

4. Add QRNGTL (SEQ ID: 123) and VDLAPS (SEQ ID: 114) to GFPuv-His construct with EETI (N term) Loop 5 deletion using site directed mutagenesis:

End Lac
Start HindIII EET1 WT
ATGACCATGATTACGCCAAGCTTGGGGTGCCCGCGAATCCTAATGCGTTG

Delete Loop 5
GGGCCCAACGGTTTC add: Q R N G T L (SEQ ID: 123)
CAAACAGGACTCCGACTGC**CTGGCTGGCTGCGTTtgc*CAAAGAAACGGTACTCTT***

Gly Gly HindIII GFPuv
tgcGGAGGAGGACCAAGCTTGATGAGTAAAGGAGAA (SEQ ID: 228)

Primers needed to add QRNGTL (SEQ ID: 123) substitution in loop 5:
ETTI-L5 add QRNGTL (SEQ ID: 123) sense
ctggctgcgtttgcCAAAGAAACGGTACTCTTtgcggaggaggacc (SEQ ID: 229)

ETTI-L5 add QRNGTL (SEQ ID: 123) antisense
ggtcctcctccgcaAAGAGTACCGTTTCTTTGgcaaacgcagccag (SEQ ID: 230)

End Lac
Start HindIII EET1 WT
ATGACCATGATTACGCCAAGCTTGGGGTGCCCGCGAATCCTAATGCGTTGCAAAC

Delete Loop 5
GGGCCCAACGGTTTC add: V D L A P S
AGGACTCCGACTGC**CTGGCTGGCTGCGTTtgc*GTTGATCTTGCTCCATCT***

```
                        Gly Gly HindIII GFPuv
tgcGGAGGAGGACCAAGCTTGATGAGTAAAGGAGAA (SEQ ID: 231)

Primers needed to add VDLAPS (SEQ ID: 228) substitution in loop 5:
ETTI-L5 add VDLAPS (SEQ ID: 114) sense
ctggctgcgtttgcGTTGATCTTGCTCCATCTtgcggaggaggacc (SEQ ID: 232)

ETTI-L5 add VDLAPS (SEQ ID: 114) antisense
ggtcctcctccgcaAGATGGAGCAAGATCAACgcaaacgcagccag (SEQ ID: 233)
```

PCR conditions for the above reactions: 25 ul 2× Phusion flash master mix; 1 ul forward primer of a 1:4 dilution of 100 uM solution; 1 ul reverse primer of a 1:4 dilution of 100 uM solution; 1 ul template of a 100 ng/ul solution; 22 ul ddH$_2$O in a total of 50 ul. The cycling conditions are: 1) 98° C. for 10 sec; 2) 98° C. for 1 sec, 55° C. for 15 sec, 72° C. for 15 sec, and repeat 31 cycles; 3) 72° C. for 1 min. PCR products were cleaned with QiaQuick PCR purification kit, digested, and run on 2% agarose gel, and bands were cut out band and purified with QiaQuick gel extraction kit cut vectors were ligated with the PCR product with rapid DNA ligation kit from Roche, and transform 2 ul of reaction into 50 ul DH5 competent cells and plate on Amp LB plates.

Site-directed mutagenesis for loop deletion conditions: Phusion Flash (NEB) 25 ul PCR master mix; 1 ul forward primer at 125 ng/ul; 1 ul Reverse primer at 125 ng/ul; 1 ul template at 50 ng/ul. 25 ul PCR master mix; 22 ul ddH$_2$O in a total 50 ul. Take reaction and cycle as follows: 1) 98° C. for 10 sec; 2) 98° C. for 5 sec and 68° C. for 1 minute at the rate of 15 sec/kb vector for a total 18 cycles; 3) 68° C. for 10 min Part III:

1). Min-23 with deleted loop 5, i.e., Min-18 construct; 2). Delete loop 5 except P, i.e., Min-19 construct; 3). Min-23 construct on pMal:

1) and 2): For Min-18 and Min 19 constructs

```
Sequence to be obtained:
CTAATGCGTTGCAAACAGGACTCCGACTGCCTGGCTGGCTGCGTT tgc(C) tgc (C)GGA, or tgc(C) TTC(P) tgc(C) GGA (SEQ ID: 234)

With the Forward primer:
GATCgcggccgc (Not 1) CTAATGCGTTGCAAACAGGAC (SEQ ID: 235);

Reverse primer:
GATCgaattc (EcoRI) TCCgcagca (C-C, deleted loop 5) AACGCAGCCAGCC (SEQ ID: 236).

Alternatively:
GATCgaattc (EcoRI) TCCgcaTTCgca (C-C, deleted loop 5 except TTC, phenylanaline) AACGCAGCCAGCC (SEQ ID: 237).
```

For the PCR reaction, use the forward and reverse primer and GFPuv-His EET1 wt with the above deleted loop 5 EETI wild type as the template.
Digest PCR fragments with Not1 and EcoR1 and ligate into c terminus of pMalp5E vector cut with Not1/EcoR1.

3). For Min-23:

```
(i) Wild type and truncated sequences:
wt EET1       start of Min-23
gggtgcccgcgaatcCTAATGCGTTGCAAACAGGACTCCGACTGCCTGGCTGGCTGCGT

TTGCGGGCCCAACGGTTTCTGCGGA 10      20      30      40      50
gggtgcccgcgaatc (EETI 5' deleted) cccacgggcgcttag (SEQ ID: 238)

(Min-23 start)
CTAATGCGTTGCAAACAGGACTCCGACTGCCTGGCTGGCTGCGTTTGCGG

GATTACGCAACGTTTGTCCTGAGGCTGACGGACCGACCGACGCAAACGCC

L M R C K Q D S D C L A G C V C G

60
GCCCAACGGTTTCTGCGGA (SEQ ID: 239)

CGGGTTGCCAAAGACGCCT (SEQ ID: 240)

P N G F C G (SEQ ID: 243)
```

-continued (ii) Primer design:
Min23 For PCR primer with Not1 ends:
  Not1
GATC*gcggccgc*CTAATGCGTTGCAAACAGGAC (SEQ ID: 241) forward primer Min23 Rev PCR primer with EcoR1 ends:
GATC*gaattc* (EcoRI)TCCGCAGAAACCGTTGGGCCC (SEQ ID: 242) reverse primer Procedures for constructs: Forward and reverse primers in 10 were added in a PCR reaction with GFPuv-His EET1 wt as the template: Gcggccgc (Not 1) (Min-23: CTAATGCGTTG-CAAACAGGACTCCGACTGCCTGGCTGGCTGCG-TTTGCGGGCCCA ACGGTTTCTGCGGAgaattc (EcoRI) (SEQ ID: 278). PCR product was digested with Not1/EcoR1, and ligated to pMAL 5pE that was digested with Not1 and EcoR1 on the C terminus of the maltose gene with the removal of the Gly-Gly-linker from pMal, and the fused PCR fragment was then cloned into Not1/EcoR1 pMal5pE.

We claim:

1. An IgE allergy vaccine comprising an IgE epitope peptide fused to an immunogenic protein scaffold, wherein the IgE epitope consists of SEQ ID: 8, SEQ ID: 10, SEQ ID: 12, SEQ ID: 14, or SEQ ID: 16.

2. A method of treating or inhibiting the development of IgE-mediated allergic disease comprising administering the IgE allergy vaccine of claim 1 admixed with an adjuvant to a subject in need thereof.

3. A polypeptide comprising in amino to carboxyl orientation the super beta-strand peptide QCRVTHP (SEQ ID: 36), a B cell epitope peptide, the super beta-strand peptide ALMRST (SEQ ID: 40) and the peptide TKTSGPR (SEQ ID: 126), wherein said polypeptide is fused to a protein scaffold.

4. A method of inducing an antibody response in a subject comprising administering the composition of claim 3 admixed with an adjuvant to a subject in need thereof.

5. A polypeptide comprising SEQ ID: 270 or a truncation thereof which lacks one (N-1) or two (N-2) or three (N-3) or four (N-4) or five (N-5) or six (N-6) or seven (N-7) or eight (N-8) or nine (N-9) or ten (N-10) amino acids at the N-terminus, said polypeptide or truncation thereof further comprising a B-cell epitope peptide inserted prior to ALMRST (SEQ ID: 40) of said polypeptide or truncation thereof and wherein said polypeptide or truncation thereof is fused to a protein scaffold.

6. A method of inducing an antibody response in a subject comprising administering the composition of claim 5 admixed with an adjuvant to a subject in need thereof.

7. The polypeptide of claim 3, wherein the B cell epitope peptide is selected from the group consisting of SEQ ID: 23, SEQ ID: 110, SEQ ID:112, SEQ ID: 114, SEQ ID: 118, SEQ ID: 119, SEQ ID: 120, SEQ ID: 121, SEQ ID: 122, SEQ ID: 123, SEQ ID: 124, SEQ ID: 279, and SEQ ID: 280 of the human origin; or from the group consisting of IgE peptides involved in binding to FcεRI of the avian, bovine, canine, caprine, equine, feline, leporine, murine, ovine, porcine, or primate origin.

8. The polypeptide of claim 5, wherein the B cell epitope peptide is selected from the group consisting of SEQ ID: 23, SEQ ID: 110, SEQ ID:112, SEQ ID: 114, SEQ ID: 118, SEQ ID: 119, SEQ ID: 120, SEQ ID: 121, SEQ ID: 122, SEQ ID: 123, SEQ ID: 124, SEQ ID: 279, and SEQ ID: 280 of the human origin; or from the group consisting of IgE peptides involved in binding to FcϵRI of the avian, bovine, canine, caprine, equine, feline, leporine, murine, ovine, porcine, or primate origin.

9. A method of treating or inhibiting the development of IgE-mediated allergic disease comprising administering the composition of claim 3 admixed with an adjuvant to a subject in need thereof.

10. A method of treating or inhibiting the development of IgE-mediated allergic disease comprising administering the composition of claim 5 admixed with an adjuvant to a subject in need thereof.

11. The polypeptide of claim 3 inserted in an EETI-II derived cystine-knot polypeptide selected from the group consisting of SEQ ID: 42, SEQ ID: 44, SEQ ID: 46, and SEQ ID: 48, and wherein the polypeptide further comprises a protein scaffold admixed with an adjuvant, whereby the polypeptidic protein scaffold induces antibodies in a subject in need thereof.

12. The polypeptide of claim 5 inserted in an EETI-II derived cystine-knot polypeptide selected from the group consisting of SEQ ID: 42, SEQ ID: 44, SEQ ID: 46, and SEQ ID: 48, and wherein the polypeptide further comprises a protein scaffold admixed with an adjuvant, whereby the polypeptidic protein scaffold induces antibodies in a subject in need thereof.

13. A polypeptide of claim 3, wherein the B cell epitope peptide is selected from the group consisting of SEQ ID: 23, SEQ ID: 110, SEQ ID:112, SEQ ID: 114, SEQ ID: 118, SEQ ID: 119, SEQ ID: 120, SEQ ID: 121, SEQ ID: 122, SEQ ID: 123, SEQ ID: 124, SEQ ID: 279, and SEQ ID: 280 of the human origin; or from the group consisting of IgE peptides involved in binding to FcεRI of the avian, bovine, canine, caprine, equine, feline, leporine, murine, ovine, porcine, or primate origin, wherein the polypeptide is fused to a protein scaffold admixed with an adjuvant as IgE vaccine, whereby a subject in need thereof produces antibodies inhibiting the development of IgE-mediated allergic disease.

14. A polypeptide of claim 5, wherein the B cell epitope peptide is selected from the group consisting of SEQ ID: 23, SEQ ID: 110, SEQ ID:112, SEQ ID: 114, SEQ ID: 118, SEQ ID: 119, SEQ ID: 120, SEQ ID: 121, SEQ ID: 122, SEQ ID: 123, SEQ ID: 124, SEQ ID: 279, and SEQ ID: 280 of the human origin; or from the group consisting of IgE peptides involved in binding to FcεRI of the avian, bovine, canine, caprine, equine, feline, leporine, murine, ovine, porcine, or primate origin, wherein the polypeptide is fused to a protein scaffold admixed with an adjuvant as IgE vaccine, whereby a subject in need thereof produces antibodies inhibiting the development of IgE-mediated allergic disease.

15. The polypeptide of claim 3, wherein the B cell epitope peptide is a sequence from an infectious microbe, wherein said polypeptide further comprises an immunogenic protein scaffold admixed with an adjuvant, whereby said polypeptidic protein scaffold induces protective antibodies in a subject infected with an infectious microbe.

16. The polypeptide of claim 5, wherein the B cell epitope peptide is a sequence from an infectious microbe, wherein said polypeptide further comprises an immunogenic protein scaffold admixed with an adjuvant, whereby said polypeptidic protein scaffold induces protective antibodies in a subject infected with an infectious microbe.

17. A polypeptide comprising in amino to carboxyl orientation the super beta strand peptide ALMRST (SEQ ID NO:40), a B cell epitope peptide, and the super beta strand peptide QCRVTHP (SEQ ID NO:36), wherein the polypeptide is fused to a protein scaffold as a polypeptidic protein scaffold vaccine, admixed with an adjuvant.

18. The polypeptide of claim 17 inserted into an EETI-II derived cystine-knot polypeptide selected from the group consisting of SEQ ID: 42, SEQ ID: 44, SEQ ID: 46, and SEQ ID: 48, wherein the polypeptide is fused to a protein scaffold as a polypeptidic protein scaffold vaccine, admixed with an adjuvant.

19. The polypeptide of claim 17, wherein the B cell epitope peptide is selected from the group consisting of SEQ ID: 23, SEQ ID: 110, SEQ ID:112, SEQ ID: 114, SEQ ID: 118, SEQ ID: 119, SEQ ID: 120, SEQ ID: 121, SEQ ID: 122, SEQ ID: 123, SEQ ID: 124, SEQ ID: 279, and SEQ ID: 280 of the human origin; or from the group consisting of IgE peptides involved in binding to FcεRI of the avian, bovine, canine, caprine, equine, feline, leporine, murine, ovine, porcine, or primate origin, wherein the polypeptide is fused to a protein scaffold as a polypeptidic protein scaffold IgE vaccine, whereby a subject in need thereof produces antibodies inhibiting the development of IgE-mediated allergic disease.

20. The polypeptide of claim 18, wherein the B cell epitope peptide is selected from the group consisting of SEQ ID: 23, SEQ ID: 110, SEQ ID:112, SEQ ID: 114, SEQ ID: 118, SEQ ID: 119, SEQ ID: 120, SEQ ID: 121, SEQ ID: 122, SEQ ID: 123, SEQ ID: 124, SEQ ID: 279, and SEQ ID: 280 of the human origin; or from the group consisting of IgE peptides involved in binding to FcεRI of the avian, bovine, canine, caprine, equine, feline, leporine, murine, ovine, porcine, or primate origin, wherein the polypeptide is fused to a protein scaffold as a polypeptidic protein scaffold IgE vaccine, whereby a subject in need thereof produces antibodies inhibiting the development of IgE-mediated allergic disease.

\* \* \* \* \*